US008017630B2

(12) United States Patent
Hinze et al.

(10) Patent No.: US 8,017,630 B2
(45) Date of Patent: *Sep. 13, 2011

(54) CYCLOHEXYLACETIC ACID COMPOUNDS

(75) Inventors: Claudia Hinze, Aachen (DE); Bernd Sundermann, Aachen (DE); Hans Schick, Berlin (DE); Birgitta Henkel, Berlin (DE)

(73) Assignee: Gruenenthal GmbH, Aachen (DE)

( * ) Notice: Subject to any disclaimer, the term of this patent is extended or adjusted under 35 U.S.C. 154(b) by 768 days.

This patent is subject to a terminal disclaimer.

(21) Appl. No.: 11/594,945

(22) Filed: Nov. 9, 2006

(65) Prior Publication Data

US 2007/0129347 A1 Jun. 7, 2007

Related U.S. Application Data

(63) Continuation of application No. PCT/EP2005/004909, filed on May 6, 2005.

(30) Foreign Application Priority Data

May 10, 2004 (DE) .......................... 10 2004 023 507

(51) Int. Cl.
 A61K 31/4402 (2006.01)
 A61K 31/4045 (2006.01)
 A61K 31/165 (2006.01)
 C07D 213/38 (2006.01)
 C07D 213/56 (2006.01)
 C07D 401/12 (2006.01)
 C07D 209/14 (2006.01)
 C07C 233/11 (2006.01)

(52) U.S. Cl. ........ 514/339; 514/357; 514/415; 514/619; 546/277.4; 546/337; 548/504; 564/168

(58) Field of Classification Search .................. None
See application file for complete search history.

(56) References Cited

U.S. PATENT DOCUMENTS

| 4,115,589 | A | 9/1978 | Lednicer |
| 4,212,878 | A | 7/1980 | Lednicer et al. |
| 4,346,101 | A | 8/1982 | Lednicer |
| 4,366,172 | A | 12/1982 | Lednicer |
| 5,109,020 | A | 4/1992 | Negele et al. |
| 5,239,110 | A | 8/1993 | Mallamo et al. |
| 5,304,479 | A | 4/1994 | Lin |
| 2003/0008859 | A1 | 1/2003 | Sundermann et al. |
| 2003/0229119 | A1 | 12/2003 | Kym et al. |
| 2003/0236250 | A1 | 12/2003 | Castro Pineiro et al. |

FOREIGN PATENT DOCUMENTS

| DE | 2839891 | 4/1979 |
| DE | 19963175 | 7/2001 |
| EP | 0410191 | 1/1991 |
| EP | 1 323 710 A1 | 7/2003 |
| JP | 2004-002368 | * 1/2004 |
| WO | WO 01/12195 | 2/2001 |
| WO | WO 02/090317 A1 | 11/2002 |
| WO | WO 03/082847 | * 10/2003 |
| WO | WO 2004/022535 A1 | 3/2004 |
| WO | WO 2004/043949 A1 | 5/2004 |
| WO | WO 2006/040646 | * 4/2006 |

OTHER PUBLICATIONS

"Correspond." The American Heritage® Dictionary of the English Language. Boston: Houghton Mifflin, 2007. Credo Reference. Web. Sep. 15, 2009.*
Prasmickiene et al. Izuch. Funkts. Kletki (1981) pp. 35-41.*
International Search Report dated Sep. 9, 2005 with a partial translation of the relevant portion (Four (4) pages).
International Preliminary Report on Patentability dated Nov. 14, 2006 with a partial translation (Six (6) pages).
German Office Action dated Oct. 10, 2004 (Two (2) pages).
Daniel Lednicer et al., "4-(p-Bromophenyl)-4-(dimethylamino)-1-phenethylcyclohexanol, an Extremely Potent Representative of a New Analgesic Series", Journal of Medicinal Chemistry, Oct. 1979, pp. 1157-1158, vol. 22, No. 10, American Chemical Society.
Hiroshi Kawamoto et al., "Synthesis of J-113397, the First Potent and Selective ORL1 Antagonist," Tetrahedron, 2001, pp. 981-986, 57, Elsevier Science Ltd.
Phillip F. Vonvoigtlander et al., "4-Aryl-4-aminocyclohexanone Derivatives: A Chemically Novel Series of Analgesics Including Opioid Antagonists and Extremely Potent Agonists," pp. 17-21, Meeting date 1979, Pergamon, Elmsford, NY.
Swahn, B.M. et al., "Synthesis of some cyclohexanol derivatives", 1987: 423027 CAPLUS, Doc. No. 107:23027, Foersvarets Forskningsanst., Umea, Swed., Report (1985).
Faud A. Abdulla et al., "Axotomy Reduces the Effect of Analgesic Opioids Yet Increases the Effect of Nociceptin on Dorsal Root Ganglion Neurons," The Journal of Neuroscience, Dec. 1, 1998, pp. 9685-9694, 18, 23, Society for Neuroscience.

(Continued)

*Primary Examiner* — Rebecca Anderson
*Assistant Examiner* — Alicia L Otton
(74) *Attorney, Agent, or Firm* — Crowell & Moring LLP

(57) ABSTRACT

Novel cyclohexylacetic acid compounds corresponding to formula I:

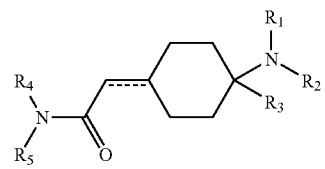

processes for the production thereof, pharmaceutical compositions containing these compounds, methods of producing pharmaceutical compositions including these compounds and related methods of treating or inhibiting certain diseases or conditions.

16 Claims, No Drawings

OTHER PUBLICATIONS

Girolamo Calo et al., "Pharmacology of Nociceptin and its Receptor: A Novel Therapeutic Target," British Journal of Pharmacology, 2000, pp. 1261-1283, 129, Macmillan Publishers Ltd.

Mark Connor et al., Special Report, "The Effect of Nocliceptin on $Ca^{2+}$ Channel Current and Intracellular $Ca^{2+}$ in the SH-SY5Y Human Neuroblastoma Cell Line", British Journal of Pharmacology, 1996, pp. 205-207, 118, Stockton Press.

E.S.L. Faber et al., Special Report, "Depression of Glutamatergic Transmission by Nociceptin in the Neonatal Rat Hemisected Spinal Cord Preparation In Vitro", Jul. 19, 1996, pp. 1-2.

"Opioid and Opiate Receptors: Peptides and Knock-Out," Society for Neuroscience, 1998, p. 1358, vol. 24.

Francois Jenck et al., "Orphanin FQ Acts as an Anxiolytic to Attenuate Behavioral Responses to Stress," Proc. Natl. Acad. Sci., Dec. 1997, pp. 14854-14858, vol. 94, USA.

Michael A. King et al., "Spinal Analgesic Activity of Orphanin FQ/Nociceptin and its Fragments", Neuroscience Letters, 1997, pp. 113-116, 223, Elsevier Science Ireland Ltd.

Toshiya Manabe et al., "Facilitation of Long-Term Potentiation and Memory in Mice Lacking Nociceptin Receptors", Letters to Nature, Aug. 6, 1998, pp. 577-581, vol. 394, Macmillan Publishers Ltd.

Jean-Claude Meunier et al., "Isolation and Structure of the Endogenous Agonist of Opiod Receptor-Like $ORL_1$ Receptor," Letters to Nature, Oct. 12, 1995, pp. 532-535, vol. 377.

J.S. Mogil et al., "Orphanin FQ is a Functional Anti-Opioid Peptide", Neuroscience, 1996, pp. 333-337, vol. 75, No. 2, Elsevier Science Ltd., Great Britain.

Miyuki Nishi et al., "Unrestrained Nociceptive Response and Disregulation of Hearing Ability in Mice Lacking the Nociceptin/OrphaninFQ Receptor," The EMBO Journal, 1997, pp. 1858-1864, vol. 16, No. 8, Oxford University Press.

Rainer K. Reinscheid et al., "Orphanin FQ: A Neuropeptide That Activates an Opioldlike G Protein-Coupled Receptor," Science, Nov. 3, 1995, pp. 792-794, vol. 270.

Christopher W. Vaughan et al., Special Report, "Increase by the $ORL_1$ Receptor (Opioid Receptor-like$_1$) Ligand, Nociceptin, of Inwardly Rectifying K Conductance in Dorsal Raphe Nucleus Neurones," Special Report, pp. 1609-1611, 1996.

Tatsuo Yamamoto et al., "Effects of Intrathecally Administered Nociceptin, an Opioid Receptor-likes Receptor Agonist, and N-methyl-D-aspartate Receptor Antagonist on the Thermal Hyperalgesia Induced By Partial Sciatic Nerve Injury in the Rat," Anesthesiology, 1997, pp. 1145-1152, vol. 87, No. 5, Lippincott-Raven Publishers.

Ali Ardati et al., "Interaction of [$^3$H]Orphanin FQ and $^{125}$I-Tyr14-Orphanin FQ with the Orphanin FQ Receptor: Kinetics and Modulation by Cations and Guanine Nucleotides," Molecular Pharmacology, 1997, pp. 816-824, 51, The American Society for Pharmacology and Experimental Therapeutics.

Hunter C. Champion et al., "[Tyr$^1$]-Nociceptin, a Novel Nociceptin Analog, Decreases Systemic Arterial Pressure by a Naloxone-Insensitive Mechanism in the Rat," Biochemical and Biophysical Research Communications, 1997, pp. 309-312, 234, Academic Press, Article No. RC976629.

Tristan Darland et al., "Orphanin FQ/nociceptin: a Role in Pain and Analgesia, But So Much More," TINS, 1998, pp. 215-221, vol. 21, No. 5, Elsevier Science Ltd.

Bulent Gumusel et al., "Nociceptin: An Endogenous Agonist for Central Opioid Like$_1$ ($ORL_1$) Receptors Possesses Systemic Vasorelaxant Properties," Life Sciences, 1997, pp. PL 141-PL 145, vol. 60, No. 8, Elsevier Science Inc., USA.

Naoki Hara et al., "Characterization of Nociceptin Hyperalgesia and Allodynia in Conscious Mice," British Journal of Pharmacology, 1997, pp. 401-408, 121, Stockton Press.

Daniel R. Kapusta et al., "Diuretic and Antinatriuretic Responses Produced by the Endogenous Opioid-Like Peptide, Nociceptin (Orphanin FQ)," Life Sciences, 1997, pp. PL 15-PL 21, vol. 60, No. 1, Elsevier Science Inc., USA.

Frederic Knoflach et al., "Modulation of Voltage-Gated Calcium Channels by Orphanin FQ in Freshly Dissociated Hippocampal Neurons," The Journal of Neuroscience, Nov. 1, 1996, pp. 6657-6664, 16, 21, Society for Neuroscience.

Hans Matthes et al., "Functional Selectivity of Orphanin FQ for Its Receptor Coexpressed with Potassium Channel Subunits in *Xenopus laevis* Oocytes," Molecular Pharmacology, 1996, pp. 447-450, 50, The American Society for Pharmacology and Experimental Therapeutics.

Jeffrey S. Mogil et al., "Functional Antagonism of µ-, δ- and κ-opioid Antinociception by Orphanin FQ," Neuroscience Letters, 1996, pp. 131-134, 214, Elsevier Science Ireland Ltd.

Catherine Mollereau et al., "ORL1, A Novel Member of the Opioid Receptor Family Cloning, Functional Expression and Localization," FEBS Letters, 341, pp. 33-38, (1994) Federation of European Biochemical Societies.

James D. Pomonis et al., "Orphanin FQ, Agonist of Orphan Opioid Receptor $ORL_1$, Stimulates Feeding in Rats," NeuroReport, Dec. 20, 1996, pp. 369-371, vol. 8, No. 1, Rapid Science Publishers.

Y.-S. Shu et al., "Orphanin FQ/Nociceptin Modulates Glutamate- and Kainic Acid-Induced Currents in Acutely Isolated Rat Spinal Dorsal Horn Neurons," Neuropeptides, 1998, pp. 567-571, 32, Harcourt Brace & Co., Ltd.

Xiao-Jun Xu et al., "Nociceptin or Antinociceptin: Potent Spinal Antinociceptive Effect of Orphanin FQ/ Nociceptin in the Rat," NeuroReport, Sep. 2, 1996, vol. 7, No. 13, Rapid Science Publishers.

T. Yamamoto et al., "Analgesic Effect of Intrathecally Administered Nociceptin, an Opioid Receptor-Like$_1$ Receptor Agonist, in the Rat Formalin Test," Neuroscience, 1997, pp. 249-254, vol. 81, Elsevier Science Ltd.

M.N.A. Rao et al., "Quantitative Correlation Between Hydrophobicity and AnalgesiC Activity of 4-Amino 4-Arylcyclohexanols," Indian Drugs, 1985, pp. 252-257, 22, 5.

Jean-Marc Kamenka et al., "Orientation Structurale et Conformationnelle de la Fixation de la Phencyclidine dans le SNC," Eur. J. Med. Chem. 1984, pp. 255-260, No. 3, 1984-19.

Daniel Lednicer et al., "4-Amino-4-arylcyclohexanones and Their Derivatives, a Novel Class of Analgestics", J. Med. Chem., 1980, pp. 424-430, 23.

* cited by examiner

CYCLOHEXYLACETIC ACID COMPOUNDS

CROSS-REFERENCE TO RELATED APPLICATIONS

This application is a continuation of International patent application Serial No. PCT/EP2005/004909 filed May 6, 2005 which claims benefit to German patent application Serial No. 10 2004 023 507.4 filed May 10, 2004, the entire disclosures of which are hereby incorporated in their entirety.

FIELD OF THE INVENTION

The present invention relates to substituted cyclohexylacetic acid derivatives, processes for the production thereof, pharmaceutical compositions containing these compounds, methods of producing pharmaceutical compositions including these compounds and related methods of treating or inhibiting certain diseases or conditions.

BACKGROUND OF THE INVENTION

The treatment of chronic and non-chronic states of pain is of great importance in medicine. There is a worldwide need for pain therapies which are highly effective. The urgent need for action for targeted treatment of chronic and non-chronic states of pain appropriate for the patient, by which is to be understood successful and satisfactory pain treatment for the patient, is documented in the large number of scientific works which have been published recently in the field of applied analgesics and of basic research into nociception.

Conventional μ-opioids, such as morphine, have a good action in the therapy of severe to very severe pain and are of very great importance for pain therapy. However, it may be of advantage if, in addition to the μ-opioid receptor, other opioid receptors, in particular the ORL1 receptor, are influenced since pure μ-opioids also have undesirable side effects, such as constipation and respiratory depression, and can also lead to dependency. The δ, κ and ORL1 opioid receptors are also involved in the pain event (Opioids: Introduction, p. 127-150, Further Opioid Receptors, 455-476 in: Analgesics—From Chemistry and Pharmacology to Clinical Application, Wiley VCH, 2002).

It is moreover known that influencing of the reuptake of serotonin and/or noradrenaline can have a favourable effect on the action spectrum and spectrum of side effects of opioids (example: tramadol, cf. Opioids with Clinical Relevance: Tramadol, 228-230 in: Analgesics—From Chemistry and Pharmacology to Clinical Application, Wiley VCH 2002).

The ORL1 receptor is moreover also involved in regulation of further physiological and pathophysiological processes. These include, inter alia, learning and memory development (Manabe et al., Nature, 394, 1997, p. 577-581), audition (Nishi et al., EMBO J., 16, 1997, p. 1858-1864) and numerous further processes. A review article by Calo et al. (Br. J. Pharmacol., 129, 2000, 1261-1283) gives an overview of the indications or biological processes in which the ORL1 receptor plays a role or with high probability could play a role. There are mentioned, inter alia: analgesia, stimulation and regulation of food intake, influence on μ-agonists, such as morphine, treatment of withdrawal symptoms, reduction in the addiction potential of opioids, anxiolysis, modulation of movement activity, memory impairments, epilepsy; modulation of neurotransmitter secretion, in particular of glutamate, serotonin and dopamine, and therefore neurodegenerative diseases; influencing of the cardiovascular system, initiation of an erection, diuresis, antinatriuresis, electrolyte balance, arterial blood pressure, water retention diseases, intestinal motility (diarrhea), relaxing effects on the respiratory tract, micturition reflex (urinary incontinence). The use of agonists and antagonists as anoretics, analgesics (also in co-administration with opioids) or nootropics is also discussed.

Structurally related compounds which have an affinity for the ORL1 receptor are known from the prior art (WO 02090317). No influence on the reuptake of noradrenaline and serotonin has hitherto been described for this structure class.

SUMMARY OF THE INVENTION

The object of the present invention was to provide medicaments which act on the opioid receptor system and are therefore suitable for medicaments, in particular for treatment of the various diseases associated with this system according to the prior art, and for use in the indications mentioned there. The compounds should furthermore influence the reuptake of noradrenaline and serotonin.

The invention therefore provides substituted cyclohexylacetic acid derivatives of the general formula I

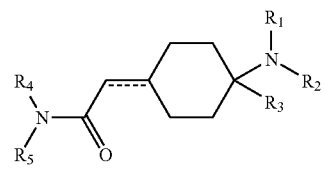

wherein represents a C—C single bond or double bond, $R^1$ and $R^2$ independently of one another represent H; CHO; $C_{1-5}$-alkyl, in each case saturated or unsaturated, branched or unbranched, mono- or polysubstituted or unsubstituted; $C_{3-8}$-cycloalkyl, in each case saturated or unsaturated, mono- or polysubstituted or unsubstituted; or aryl, $C_{3-8}$-cycloalkyl or heteroaryl bonded via $C_{1-3}$-alkyl and in each case mono- or polysubstituted or unsubstituted;

or the radicals $R^1$ and $R^2$ together represent $CH_2CH_2OCH_2CH_2$, $CH_2CH_2NR^{10}CH_2CH_2$ or $(CH_2)_{3-6}$, wherein $R^{10}$ denotes H; $C_{1-5}$-alkyl, in each case saturated or unsaturated, branched or unbranched, mono- or polysubstituted or unsubstituted; $C_{3-8}$-cycloalkyl, in each case saturated or unsaturated, mono- or polysubstituted or unsubstituted; aryl or heteroaryl, in each case mono- or polysubstituted or unsubstituted; or aryl, $C_{3-8}$-cycloalkyl or heteroaryl bonded via $C_{1-3}$-alkyl and in each case mono- or polysubstituted or unsubstituted;

$R^3$ represents $C_{1-5}$-alkyl, in each case saturated or unsaturated, branched or unbranched, mono- or polysubstituted or unsubstituted; $C_{3-8}$-cycloalkyl, in each case saturated or unsaturated, mono- or polysubstituted or unsubstituted; aryl, heteroaryl or $C_{3-8}$-cycloalkyl bonded via $C_{1-3}$-alkyl and in each case unsubstituted or mono- or polysubstituted; naphthyl, anthracenyl, thiophenyl, benzothiophenyl, furyl, benzofuranyl, benzodioxolanyl, indolyl, indanyl, benzodioxanyl, pyrrolyl, pyridyl, pyrimidyl or pyrazinyl, in each case unsubstituted or mono- or polysubstituted; phenyl, 2-fluorophenyl, 3-fluorophenyl, 4-fluorophenyl, 2-chlorophenyl, 4-chlorophenyl, 3-chlorophenyl, 2-bromophenyl, 3-bromophenyl, 4-bromophenyl, 2-cyanophenyl, 3-cyanophenyl, 4-cyanophenyl, 2-methylphenyl, 3-methylphenyl, 4-methylphenyl, 2-methoxyphenyl, 3-methoxyphenyl, 4-methoxyphenyl, 2-trifluoromethylphenyl, 3-trifluoromethylphenyl, 4-trifluoromethylphenyl, 2-ethylphenyl, 3-ethylphenyl, 4-ethylphenyl, 2-ethoxyphenyl, 3-ethoxyphenyl, 4-ethoxyphenyl, 2-hydroxyphenyl, 3-hydroxyphenyl, 4-hydroxyphenyl, 2,3-dichlorophenyl, 3,4-dichlorophenyl, 3,5-dichlorophenyl, 2,4-dichlorophenyl, 2,3-difluorophenyl, 3,4-difluorophenyl, 3,5-difluorophenyl, 2,4-difluorophenyl, 2-fluoro-3-chlorophenyl, 2-chloro-3-fluorophenyl, 2-chloro-4-fluorophenyl, 2-fluoro-4-chlorophenyl, 4-fluoro-3-chlorophenyl, 4-fluoro-3-methylphenyl, 4-tert-butylphenyl, 4-fluoro-3-chlorophenyl, 4-bromo-3-fluorophenyl, 3,5-bis(trifluoromethyl)phenyl, 4-chloro-2-trifluoromethylphenyl, 2-methoxy-5-methylphenyl, 5-chloro-2-methoxyphenyl, 4-phenoxyphenyl, 2-methylthiophenyl, 3-methylthiophenyl, 4-methylthiophenyl, 5-fluoro-2-methoxyphenyl, 4-chloro-3-trifluoromethyl or 4-bromo-2-methylphenyl;

$R^4$ represents $—(CR^6R^7)_nR^8$, wherein n denotes 0, 1, 2, 3, 4, 5 or 6, $R^6$ denotes H or $C_{1-5}$-alkyl, saturated or unsaturated, branched or unbranched, unsubstituted or mono- or polysubstituted, $R^7$ denotes H, $C_{1-5}$-alkyl, saturated or unsaturated, branched or unbranched, unsubstituted or mono- or polysubstituted, or $COOR^9$, or $R^6$ and $R^7$ form a $(CH_2)_k CHR^8 (CH_2)_m$ ring, where k=1, 2 or 3 and m=1 or 2;

$R^8$ denotes $C_{3-8}$-cycloalkyl, aryl or heteroaryl, in each case unsubstituted or mono- or polysubstituted, $R^9$ denotes H or $C_{1-5}$-alkyl, saturated or unsaturated, branched or unbranched, unsubstituted or mono- or polysubstituted;

$R^5$ represents H or $—(CH_2)_l R^8$, wherein l represents 1, 2 or 3, or together with $R^4$ represents $CH_2CH_2OCH_2CH_2$, $CH_2CH_2NR^{11}CH_2CH_2$ or $(CH_2)_{3-6}$, wherein $R^{11}$ denotes H; $C_{1-5}$-alkyl, in each case saturated or unsaturated, branched or unbranched, mono- or polysubstituted or unsubstituted; $C_{3-8}$-cycloalkyl, in each case saturated or unsaturated, mono- or polysubstituted or unsubstituted; aryl or heteroaryl, in each case mono- or polysubstituted or unsubstituted; or aryl, $C_{3-8}$-cycloalkyl or heteroaryl bonded via $C_{1-3}$-alkyl and in each case mono- or polysubstituted or unsubstituted;

in the form of the racemate; the enantiomers, diastereomers, mixtures of the enantiomers or diastereomers or an individual enantiomer or diastereomer; the bases and/or salts of physiologically acceptable acids or cations.

The compounds according to the invention show good binding to the p receptor and the ORL1 receptor, and also to other opioid receptors. It has been found, surprisingly, that the compounds are also good inhibitors of the reuptake of noradrenaline and serotonin. They are therefore also suitable for treatment of depressions and/or bulimia and/or anorexia and/or catalepsy and/or for anxiolysis and/or for increasing vigilance and/or libido.

The terms "$C_{1-5}$-alkyl" and "$C_{1-3}$-alkyl" in the context of this invention include acyclic saturated or unsaturated hydrocarbon radicals, which can be branched-chain or straight-chain and unsubstituted or mono- or polysubstituted, having 1, 2, 3, 4 or 5 C atoms or, respectively, 1, 2 or 3 C atoms, i.e. $C_{1-5}$-alkanyls, $C_{2-5}$-alkenyls and $C_{2-5}$-alkynyls or, respectively, $C_{1-3}$-alkanyls, $C_{2-3}$-alkenyls and $C_{2-3}$-alkynyls. In this context, alkenyls have at least one C—C double bond and alkynyls have at least one C—C triple bond. Alkyl is advantageously chosen from the group which includes methyl, ethyl, n-propyl, 2-propyl, n-butyl, iso-butyl, sec-butyl, tert-butyl, n-pentyl, iso-pentyl, neo-pentyl, n-hexyl, 2-hexyl; ethylenyl (vinyl), ethynyl, propenyl ($—CH_2CH=CH_2$, $—CH=CH—CH_3$, $—C(=CH_2)—CH_3$), propynyl ($—CH—C\equiv CH$, $—C\equiv C—CH_3$), 1,1-dimethylethyl, 1,1-dimethylpropyl, butenyl, butynyl, pentenyl and pentynyl.

The term "cycloalkyl" or "$C_{3-8}$-cycloalkyl" for the purpose of this invention denotes cyclic hydrocarbons having 3, 4, 5, 6, 7 or 8 carbon atoms, it being possible for the hydrocarbons to be saturated or unsaturated (but not aromatic), unsubstituted or mono- or polysubstituted. In respect of cycloalkyl, the expression also includes saturated or unsaturated (but not aromatic) cycloalkyls in which one or two carbon atoms are replaced by a heteroatom S, N or O. $C_{3-8}$-Cycloalkyl is advantageously chosen from the group which contains cyclopropyl, cyclobutyl, cyclopentyl, cyclohexyl, cycloheptyl, cyclooctyl, cyclopentenyl, cyclohexenyl, cycloheptenyl and cyclooctenyl, and also tetrahydropyranyl, dioxanyl, dioxolanyl, morpholinyl, piperidinyl, piperazinyl, pyrazolinonyl and pyrrolidinyl.

The expression $(CH_2)_{3-6}$ is to be understood as meaning $—CH_2—CH_2—CH_2—$, $—CH_2—CH_2—CH_2—CH_2—$, $—CH_2—CH_2—CH_2—CH_2—CH_2—$ and $—CH_2—CH_2—CH_2—CH_2—CH_2—CH_2—$.

The term "aryl" in the context of this invention denotes carbocyclic ring systems having at least one aromatic ring but without heteroatoms in only one of the rings, inter alia phenyls, naphthyls and phenanthrenyls, fluoranthenyls, fluorenyls, indanyls and tetralinyls. The aryl radicals can also be fused with further saturated, (partly) unsaturated or aromatic ring systems. Each aryl radical can be unsubstituted or mono- or polysubstituted, it being possible for the substituents on the aryl to be identical or different and in any desired and possible position of the aryl. Phenyl or naphthyl radicals are particularly advantageous.

The term "heteroaryl" represents a 5-, 6- or 7-membered cyclic aromatic radical which contains at least 1, optionally also 2, 3, 4 or 5 heteroatoms, the heteroatoms being identical or different and it being possible for the heterocyclic radical to be unsubstituted or mono- or polysubstituted; in the case of substitution on the heterocyclic radical, the substituents can be identical or different and can be in any desired and possible position of the heteroaryl. The heterocyclic radical can also be part of a bi- or polycyclic system. Preferred heteroatoms are nitrogen, oxygen and sulfur. It is preferable for the heteroaryl radical to be chosen from the group which contains pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, phthalazinyl, pyrazolyl, imidazolyl, thiazolyl, oxazolyl, isoxazolyl, pyridinyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl or oxadiazolyl, it being possible for the bond to the compounds of the general structure I to be via any desired and possible ring member of the heteroaryl radical.

In connection with "alkyl", the expression "substituted" in the context of this invention is understood as meaning replacement of one or more hydrogen radicals by F, Cl, Br, I, $=O$, $—CN$, $NH_2$, NH-alkyl, NH-aryl, NH-heteroaryl, NH-cycloalkyl, NH-alkyl-aryl, NH-alkyl-heteroaryl, NH-alkyl-OH, $N(alkyl)_2$, $N(alkyl-aryl)_2$, $N(alkyl-heteroaryl)_2$, $N(cycloalkyl)_2$, $N(alkyl-OH)_2$, $NO_2$, SH, S-alkyl, S-aryl, S-heteroaryl, S-alkyl-aryl, S-alkyl-heteroaryl, S-cycloalkyl, S-alkyl-OH, S-alkyl-SH, OH, O-alkyl, O-aryl, O-heteroaryl, O-alkyl-aryl, O-alkyl-heteroaryl, O-cycloalkyl, O-alkyl-OH, CHO, $C(=O)C_{1-6}$-alkyl, $C(=S)C_{1-6}$-alkyl, $C(=O)$aryl, $C(=S)$aryl, $C(=O)C_{1-6}$-alkyl-aryl, C(=S)C$_{1-6}$-alkyl-aryl, C(=O)-heteroaryl, C(=S)-heteroaryl, C(=O)-cycloalkyl, C(=S)-cycloalkyl, CO$_2$H, CO$_2$-alkyl, CO$_2$-alkyl-aryl, C(=O)NH$_2$, C(=O)NH-alkyl, C(=O)NHaryl, C(=O)NH-cycloalkyl, C(=O)N(alkyl)$_2$, C(=O)N(alkyl-aryl)$_2$, C(=O)N(alkyl-heteroaryl)$_2$, C(=O)N(cycloalkyl)$_2$, SO-alkyl, SO$_2$-alkyl, SO$_2$NH$_2$, SO$_3$H, PO(O—C$_{1-6}$-alkyl)$_2$, Si(C$_{1-6}$-alkyl)$_3$, Si(C$_{3-8}$-cycloalkyl)$_3$, Si(CH$_2$—C$_{3-8}$-cycloalkyl)$_3$, Si(phenyl)$_3$, cycloalkyl, aryl or heteroaryl, polysubstituted radicals being understood as meaning those radicals which are substituted several times, e.g. two or three times, either on different or on the same atoms, for example three times on the same C atom, as in the case of CF$_3$ or —CH$_2$CF$_3$, or at different places, as in the case of —CH(OH)—CH=CH—CHCl$_2$. Polysubstitution can be with the same or with different substituents. A substituent can also optionally be substituted in its turn; thus -Oalkyl, inter alia, also includes —O—CH$_2$—CH$_2$—O—CH$_2$—CH$_2$—OH.

In respect of "aryl", "heteroaryl" and "cycloalkyl", in the context of this invention "mono- or polysubstituted" is understood as meaning replacement, once or several times, e.g. two, three, four or five times, of one or more hydrogen atoms of the ring system by F, Cl, Br, I, CN, NH$_2$, NH-alkyl, NH-aryl, NH-heteroaryl, NH-alkyl-aryl, NH-alkyl-heteroaryl, NH-cycloalkyl, NH-alkyl-OH, N(alkyl)$_2$, N(alkyl-aryl)$_2$, N(alkyl-heteroaryl)$_2$, N(cycloalkyl)$_2$, N(alkyl-OH)$_2$, NO$_2$, SH, S-alkyl, S-cycloalkyl, S-aryl, S-heteroaryl, S-alkyl-aryl, S-alkyl-heteroaryl, S-cycloalkyl, S-alkyl-OH, S-alkyl-SH, OH, O-alkyl, O-cycloalkyl, O-aryl, O-heteroaryl, O-alkyl-aryl, O-alkyl-heteroaryl, O-cycloalkyl, O-alkyl-OH, CHO, C(=O)C$_{1-6}$-alkyl, C(=S)C$_{1-6}$-alkyl, C(=O)aryl, C(=S)aryl, C(=O)—C$_{1-6}$-alkyl-aryl, C(=S)C$_{1-6}$-alkyl-aryl, C(=O)-heteroaryl, C(=S)-heteroaryl, C(=O)-cycloalkyl, C(=S)-cycloalkyl, CO$_2$H, CO$_2$-alkyl, CO$_2$-alkyl-aryl, C(=O)NH$_2$, C(=O)NH-alkyl, C(=O)NHaryl, C(=O)NH-cycloalkyl, C(=O)N(alkyl)$_2$, C(=O)N(alkyl-aryl)$_2$, C(=O)N(alkyl-heteroaryl)$_2$, C(=O)N(cycloalkyl)$_2$, S(O)-alkyl, S(O)-aryl, SO$_2$-alkyl, SO$_2$-aryl, SO$_2$NH$_2$, SO$_3$H, CF$_3$, =O, =S; alkyl, cycloalkyl, aryl and/or heteroaryl; on one or optionally different atoms (it being possible for a substituent optionally to be substituted in its turn). Polysubstitution here is with the same or with different substituents.

The expression salt is to be understood as meaning any form of the active compound according to the invention in which this assumes an ionic form or is charged and is coupled with a counter-ion (a cation or anion) or is in solution. This is also to be understood as meaning complexes of the active compound with other molecules and ions, in particular complexes which are complexed via ionic interactions. In particular, by these there are understood (and this is also a preferred embodiment of this invention) physiologically acceptable salts, in particular physiologically acceptable salts with cations or bases and physiologically acceptable salts with anions or acids or also a salt formed with a physiologically acceptable acid or a physiologically acceptable cation.

In the context of this invention, the expression of physiologically acceptable salt with anions or acids is understood as meaning at least one of the compounds according to the invention—usually protonated, for example on the nitrogen—as the cation with at least one anion, which are physiologically acceptable—especially when used in humans and/or mammals. In particular, in the context of this invention by this there is understood the salt formed with a physiologically acceptable acid, namely salts of the particular active compound with inorganic or organic acids which are physiologically acceptable—especially when used in humans and/or mammals. Examples of physiologically acceptable salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid, citric acid, glutamic acid, saccharic acid, monomethylsebacic acid, 5-oxo-proline, hexane-1-sulfonic acid, nicotinic acid, 2-, 3- or 4-aminobenzoic acid, 2,4,6-trimethyl-benzoic acid, α-liponic acid, acetylglycine, phosphoric acid, maleic acid, malonic acid, hippuric acid and/or aspartic acid. The hydrochloride salt, the citrate and the hemicitrate are particularly preferred.

In the context of this invention, the expression of salt formed with a physiologically acceptable acid is understood as meaning salts of the particular active compound with inorganic or organic acids which are physiologically acceptable—especially when used in humans and/or mammals. The hydrochloride and the citrate are particularly preferred. Examples of physiologically acceptable acids are: hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, saccharic acid, monomethylsebacic acid, 5-oxo-proline, hexane-1-sulfonic acid, nicotinic acid, 2-, 3- or 4-aminobenzoic acid, 2,4,6-trimethyl-benzoic acid, α-liponic acid, acetylglycine, hippuric acid and/or aspartic acid.

In the context of this invention, the expression of physiologically acceptable salt with cations or bases is understood as meaning salts of at least one of the compounds according to the invention—usually of a (deprotonated) acid—as the anion with at least one preferably inorganic cation which are physiologically acceptable—especially when used in humans and/or mammals. The salts of the alkali metals and alkaline earth metals and also ammonium salts are particularly preferred, but especially (mono-) or (di-)sodium, (mono-) or (di-)potassium, magnesium or calcium salts.

In the context of this invention, the expression of salt formed with a physiologically acceptable cation is understood as meaning salts of at least one of the particular compounds as the anion with at least one inorganic cation which is physiologically acceptable—especially when used in humans and/or mammals. The salts of the alkali metals and alkaline earth metals and also ammonium salts are particularly preferred, but especially (mono-) or (di-)sodium, (mono-) or (di-)potassium, magnesium or calcium salts.

For a preferred embodiment of the substituted cyclohexylacetic acid derivatives according to the invention, $R^1$ and $R^2$ independently of one another represent H; C$_{1-5}$-alkyl, saturated or unsaturated, branched or unbranched, mono- or polysubstituted or unsubstituted;

or the radicals $R^1$ and $R^2$ together form a ring and denote CH$_2$CH$_2$OCH$_2$CH$_2$, CH$_2$CH$_2$NR$^{10}$CH$_2$CH$_2$ or (CH$_2$)$_{3-6}$, wherein $R^{10}$ denotes H; C$_{1-5}$-alkyl, saturated or unsaturated, branched or unbranched, mono- or polysubstituted or unsubstituted.

Particularly preferred substituted cyclohexylacetic acid derivatives are those wherein $R^1$ and $R^2$ independently of one another represent CH$_3$ or H, wherein $R^1$ and $R^2$ do not simultaneously denote H.

Substituted cyclohexylacetic acid derivatives which are furthermore preferred are those wherein $R^3$ represents cyclopentyl, cyclohexyl, naphthyl, thiophenyl, benzothiophenyl, furyl, benzofuranyl, benzodioxolanyl, indolyl, indanyl, benzodioxanyl or pyridyl, in each case unsubstituted or mono- or polysubstituted; C$_{5-6}$-cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl bonded via a saturated, unbranched $C_{1-2}$-alkyl group and in each case unsubstituted or mono- or polysubstituted; phenyl, 2-fluorophenyl, 3-fluorophenyl, 4-fluorophenyl, 2-chlorophenyl, 4-chlorophenyl, 3-chlorophenyl, 2-bromophenyl, 3-bromophenyl, 4-bromophenyl, 2-cyanophenyl, 3-cyanophenyl, 4-cyanophenyl, 2-methylphenyl, 3-methylphenyl, 4-methylphenyl, 2-methoxyphenyl, 3-methoxyphenyl, 4-methoxyphenyl, 2-trifluoromethylphenyl, 3-trifluoromethylphenyl, 4-trifluoromethylphenyl, 2-ethylphenyl, 3-ethylphenyl, 4-ethylphenyl, 2-ethoxyphenyl, 3-ethoxyphenyl, 4-ethoxyphenyl, 2-hydroxyphenyl, 3-hydroxyphenyl, 4-hydroxyphenyl, 2,3-dichlorophenyl, 3,4-dichlorophenyl, 3,5-dichlorophenyl, 2,4-dichlorophenyl, 2,3-difluorophenyl, 3,4-difluorophenyl, 3,5-difluorophenyl, 2,4-difluorophenyl, 2-fluoro-3-chlorophenyl, 2-chloro-3-fluorophenyl, 2-chloro-4-fluorophenyl, 2-fluoro-4-chlorophenyl, 4-fluoro-3-chlorophenyl, 4-fluoro-3-methylphenyl, 4-tert-butylphenyl, 4-fluoro-3-chlorophenyl, 4-bromo-3-fluorophenyl, 3,5-bis(trifluoromethyl)phenyl, 4-chloro-2-trifluoromethylphenyl, 2-methoxy-5-methylphenyl, 5-chloro-2-methoxyphenyl, 4-phenoxyphenyl, 2-methylthiophenyl, 3-methylthiophenyl, 4-methylthiophenyl, 5-fluoro-2-methoxyphenyl, 4-chloro-3-trifluoromethyl or 4-bromo-2-methylphenyl;

in particular $R^3$ represents naphthyl, thiophenyl or pyridyl, in each case unsubstituted or mono- or polysubstituted; $C_{5-6}$-cycloalkyl, phenyl, naphthyl, thiophenyl or pyridyl bonded via a saturated, unbranched $C_{1-2}$-alkyl group and in each case unsubstituted or mono- or polysubstituted; phenyl, 2-fluorophenyl, 3-fluorophenyl, 4-fluorophenyl, 2-chlorophenyl, 4-chlorophenyl, 3-chlorophenyl, 2-cyanophenyl, 3-cyanophenyl, 4-cyanophenyl, 2-methylphenyl, 3-methylphenyl, 4-methylphenyl, 2-methoxyphenyl, 3-methoxyphenyl, 4-methoxyphenyl, 2-trifluoromethylphenyl, 3-trifluoromethylphenyl, 4-trifluoromethylphenyl, 2-ethylphenyl, 3-ethylphenyl, 4-ethylphenyl, 2-ethoxyphenyl, 3-ethoxyphenyl, 4-ethoxyphenyl, 2,3-dichlorophenyl, 3,4-dichlorophenyl, 3,5-dichlorophenyl, 2,4-dichlorophenyl, 2,3-difluorophenyl, 3,4-difluorophenyl, 3,5-difluorophenyl, 2,4-difluorophenyl, 2-fluoro-3-chlorophenyl, 2-chloro-3-fluorophenyl, 2-chloro-4-fluorophenyl, 2-fluoro-4-chlorophenyl, 4-fluoro-3-chlorophenyl, 4-fluoro-3-methylphenyl, 4-tert-butylphenyl, 4-fluoro-3-chlorophenyl, 3,5-bis(tri-fluoromethyl)phenyl, 4-chloro-2-trifluoromethylphenyl, 2-methoxy-5-methylphenyl, 5-chloro-2-methoxyphenyl, 4-phenoxyphenyl, 2-methylthiophenyl, 3-methylthiophenyl, 4-methylthiophenyl or 4-chloro-3-trifluoromethyl.

Particularly preferred substituted cyclohexylacetic acid derivatives are those wherein $R^3$ represents pyridyl, substituted or unsubstituted, or phenyl, 2-fluorophenyl, 3-fluorophenyl or 4-fluorophenyl.

Preferred substituted cyclohexylacetic acid derivatives are also those in which $R^6$ denotes H and $R^7$ denotes H, $CH_3$ or $COOR^9$ or $R^6$ and $R^7$ form a $(CH_2)_k CHR^8 (CH_2)_m$ ring, where $k=1$, 2 or 3 and $m=1$ or 2.

Substituted cyclohexylacetic acid derivatives which are moreover preferred are those in which $R^5$ denotes H.

Substituted cyclohexylacetic acid derivatives which are furthermore preferred are those in which $R^8$ denotes cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzotriazolyl or benzo[1,2,5]thiazolyl or 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl, in each case unsubstituted or mono- or polysubstituted, in particular $R^8$ denotes cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, in each case unsubstituted or mono- or polysubstituted.

Particularly preferred substituted cyclohexylacetic acid derivatives are those in which $R^8$ denotes phenyl or indolyl, in each case mono- or polysubstituted.

Substituted cyclohexylacetic acid derivatives which are very particularly preferred are those from the group consisting of 2-(4-dimethylamino-4-phenyl-cyclohexylidene)-N-[2-(1H-indol-3-yl)-ethyl]-acetamide; hydrochloride 2-[2-(4-dimethylamino-4-phenyl-cyclohexylidene)-acetylamino]-3-(1H-indol-3-yl)-propanoic acid methyl ester; hydrochloride 2-(4-dimethylamino-4-phenyl-cyclohexylidene)-N-(3-phenyl-propyl)-acetamide; hydrochloride N-benzyl-2-(4-dimethylamino-4-phenyl-cyclohexylidene)-acetamide; hydrochloride 2-[2-(4-dimethylamino-4-phenyl-cyclohexylidene)-acetylamino]-3-(1H-indol-3-yl)-propanoic acid methyl ester; hydrochloride 2-(4-dimethylamino-4-phenyl-cyclohexylidene)-N-phenethyl-acetamide; hydrochloride 2-(4-dimethylamino-4-phenyl-cyclohexylidene)-N-[2-(4-fluoro-phenyl)-ethyl]-acetamide; hydrochloride 2-(4-dimethylamino-4-phenyl-cyclohexylidene)-N-(4-fluoro-benzyl)-acetamide; hydrochloride 2-(4-dimethylamino-4-phenyl-cyclohexylidene)-N-(2-trifluoromethyl-benzyl)-acetamide; hydrochloride 2-(4-dimethylamino-4-phenyl-cyclohexylidene)-N-(4-fluoro-phenyl)-acetamide; hydrochloride 2-(4-dimethylamino-4-phenyl-cyclohexylidene)-N-[2-(1H-indol-3-yl)-1-methyl-ethyl]-acetamide; hydrochloride 2-(4-Dimethylamino-4-phenyl-cyclohexylidene)-N-(4-phenyl-butyl)-acetamide; hydrochloride 2-(4-dimethylamino-4-phenyl-cyclohexylidene)-N-(1H-indol-3-ylmethyl)-acetamide; hydrochloride 2-(4-dimethylamino-4-phenyl-cyclohexylidene)-N-[4-(1H-indol-3-yl)-butyl]-acetamide; hydrochloride 2-(4-dimethylamino-4-phenyl-cyclohexylidene)-N-[3-(1H-indol-3-yl)-propyl]-acetamide; hydrochloride 2-(4-dimethylamino-4-phenyl-cyclohexylidene)-N-[5-(1H-indol-3-yl)-pentyl]-acetamide; hydrochloride 2-(4-dimethylamino-4-phenyl-cyclohexylidene)-N-[6-(1H-indol-3-yl)-hexyl]-acetamide; hydrochloride 2-[4-dimethylamino-4-(4-fluoro-phenyl)-cyclohexylidene]-N-(3-phenyl-propyl)-acetamide; hydrochloride 2-[4-dimethylamino-4-(4-fluoro-phenyl)-cyclohexylidene]-N-[2-(1H-indol-3-yl)-ethyl]-acetamide; hydrochloride 2-[4-dimethylamino-4-(4-fluoro-phenyl)-cyclohexylidene]-N-[2-(1H-indol-3-yl)-1-methyl-ethyl]-acetamide; hydrochloride 2-(4-dimethylamino-4-pyridin-2-yl-cyclohexylidene)-N-[2-(1H-indol-3-yl)-ethyl]-acetamide; hydrochloride 2-(4-dimethylamino-4-pyridin-2-yl-cyclohexylidene)-N-(3-phenyl-propyl)-acetamide; hydrochloride 2-[4-dimethylamino-4-(3-fluoro-phenyl)-cyclohexylidene]-N-[2-(1H-indol-3-yl)-ethyl]-acetamide; hydrochloride 2-[4-dimethylamino-4-(3-fluoro-phenyl)-cyclohexylidene]-N-(3-phenyl-propyl)-acetamide; hydrochloride;

2-[4-dimethylamino-4-(3-fluoro-phenyl)-cyclohexylidene]-N-[2-(1H-indol-3-yl)-1-methyl-ethyl]-acetamide; hydrochloride
2-(4-dimethylamino-4-phenylcyclohexyl)-N-(2-trifluoromethyl-benzyl)-acetamide; hydrochloride
2-(4-dimethylamino-4-phenylcyclohexyl)-N-[2-(1H-indol-3-yl)-ethyl]-acetamide; hydrochloride
2-(4-dimethylamino-4-phenylcyclohexyl)-N-(3-phenylpropyl)-acetamide; hydrochloride
2-(4-dimethylamino-4-phenylcyclohexyl)-N-phenethylacetamide; hydrochloride
2-(4-dimethylamino-4-phenylcyclohexyl)-N-(4-phenylbutyl)-acetamide; hydrochloride
2-[2-(4-dimethylamino-4-phenylcyclohexyl)-acetylamino]-3-(1H-indol-3-yl)-propanoic acid methyl ester; hydrochloride
potassium 2-[2-(4-dimethylamino-4-phenylcyclohexyl)-acetylamino]-3-(1H-indol-3-yl)-propanoate
2-(4-dimethylamino-4-phenylcyclohexyl)-N-(1H-indol-3-ylmethyl)-acetamide; hydrochloride
2-(4-dimethylamino-4-phenylcyclohexyl)-N-[4-(1H-indol-3-yl)-butyl]-acetamide; hydrochloride
2-(4-dimethylamino-4-phenylcyclohexyl)-N-[3-(1H-indol-3-yl)-propyl]-acetamide; hydrochloride
2-(4-dimethylamino-4-phenylcyclohexyl)-N-[5-(1H-indol-3-yl)-pentyl]-acetamide; hydrochloride
2-(4-dimethylamino-4-phenylcyclohexyl)-N-[2-(1H-indol-3-yl)-1-methylethyl]-acetamide; hydrochloride
2-[4-dimethylamino-4-(4-fluorophenyl)-cyclohexyl]-N-(3-phenylpropyl)-acetamide; hydrochloride
2-(4-dimethylamino-4-phenylcyclohexyl)-N-[6-(1H-indol-3-yl)-hexyl]-acetamide; hydrochloride
2-[4-dimethylamino-4-(4-fluorophenyl)-cyclohexyl]-N-[2-(1H-indol-3-yl)-ethyl]-acetamide; hydrochloride
2-[4-dimethylamino-4-(4-fluorophenyl)-cyclohexyl]-N-[2-(1H-indol-3-yl)-1-methylethyl]-acetamide; hydrochloride
2-(4-dimethylamino-4-pyridin-2-yl-cyclohexyl)-N-(3-phenylpropyl)-acetamide; hydrochloride
2-(4-dimethylamino-4-pyridin-2-yl-cyclohexyl)-N-[2-(1H-indol-3-yl)-ethyl]-acetamide; hydrochloride
2-[4-dimethylamino-4-(3-fluorophenyl)-cyclohexyl]-N-[2-(1H-indol-3-yl)-ethyl]-acetamide; hydrochloride
2-[4-dimethylamino-4-(3-fluorophenyl)-cyclohexyl]-N-(3-phenylpropyl)-acetamide; hydrochloride
2-[4-dimethylamino-4-(3-fluorophenyl)-cyclohexyl]-N-[2-(1H-indol-3-yl)-1-methylethyl]-acetamide; hydrochloride
2-(4-Dimethylamino-4-phenyl-cyclohexyl)-N-phenyl-acetamide hydrochloride
2-(4-Dimethylamino-4-phenyl-cyclohexyl)-N-(4-fluorophenyl)-acetamide hydrochloride
2-(4-Dimethylamino-4-phenyl-cyclohexyl)-N-p-tolyl-acetamide hydrochloride
2-(4-Dimethylamino-4-phenyl-cyclohexyl)-N-(4-methoxyphenyl)-acetamide hydrochloride
in the form of the racemate; the enantiomers, diastereomers, mixtures of the enantiomers or diastereomers or an individual enantiomer or diastereomer; the bases and/or salts of physiologically acceptable acids or cations.

The substances according to the invention have an action, for example, on the ORL1 receptor, which is relevant in connection with various diseases, so that they are suitable as a pharmaceutical active compound in a medicament. The invention therefore also provides medicaments comprising at least one substituted cyclohexylcarboxylic acid derivative according to the invention and optionally suitable additives and/or auxiliary substances and/or optionally further active compounds.

In addition to at least one substituted cyclohexylacetic acid derivative according to the invention, the medicaments according to the invention optionally comprise suitable additives and/or auxiliary substances, thus also carrier materials, fillers, solvents, diluents, dyestuffs and/or binders, and can be administered as liquid medicament forms in the form of injection solutions, drops or juices, as semi-solid medicament forms in the form of granules, tablets, pellets, patches, capsules, plasters/spray plasters or aerosols. The choice of the auxiliary substances etc. and the amounts thereof to be employed depend on whether the medicament is to be administered orally, perorally, parenterally, intravenously, intraperitoneally, intradermally, intramuscularly, intranasally, buccally, rectally or locally, for example to the skin, the mucous membranes or into the eyes. Formulations in the form of tablets, coated tablets, capsules, granules, drops, juices and syrups are suitable for oral administration, and solutions, suspensions, easily reconstitutable dry formulations and sprays are suitable for parenteral, topical and inhalatory administration. Substituted cyclohexylacetic acid derivatives according to the invention in a depot, in dissolved form or in a plaster, optionally with the addition of agents which promote penetration through the skin, are suitable formulations for percutaneous administration. Formulation forms which can be used orally or percutaneously can release the substituted cyclohexylacetic acid derivatives according to the invention in a delayed manner. The substituted cyclohexylacetic acid derivatives according to the invention can also be used in parenteral long-term depot forms, such as e.g. implants or implanted pumps. Other further active compounds known to the expert can in principle be added to the medicaments according to the invention.

The amount of active compound to be administered to the patient varies according to the weight of the patient, the mode of administration, the indication and the severity of the disease. 0.00005 to 50 mg/kg, preferably 0.01 to 5 mg/kg of at least one substituted cyclohexylacetic acid derivative according to the invention are conventionally administered.

For all the above forms of the medicaments according to the invention, it is particularly preferable if the medicament also comprises, in addition to at least one substituted cyclohexylacetic acid derivative, a further active compound, in particular an opioid, preferably a potent opioid, in particular morphine, or an anaesthetic, preferably hexobarbital or halothane.

In a preferred form of the medicament, a substituted cyclohexylacetic acid derivative according to the invention contained therein is in the form of a pure diastereomer and/or enantiomer, a racemate or a non-equimolar or equimolar mixture of the diastereomers and/or enantiomers.

The ORL1 receptor, and also the other opioid receptors, have been identified in particular in the pain event. Substituted cyclohexylacetic acid derivatives according to the invention can accordingly be used for the preparation of a medicament for treatment of pain, in particular acute, neuropathic or chronic pain.

The invention therefore also provides the use of a substituted cyclohexylacetic acid derivative according to the invention for the preparation of a medicament for treatment of pain, in particular acute, visceral, neuropathic or chronic pain.

The invention also provides the use of a substituted cyclohexylacetic acid derivative according to the invention for the preparation of a medicament for treatment of anxiety states, of stress and stress-associated syndromes, depressions, epilepsy, Alzheimer's disease, senile dementia, catalepsy, general cognitive dysfunctions, learning and memory disorders (as a nootropic), withdrawal symptoms, alcohol and/or drug and/or medicament abuse and/or dependency, sexual dysfunctions, cardiovascular diseases, hypotension, hypertension, tinnitus, pruritus, migraine, impaired hearing, deficient intestinal motility, impaired food intake, anorexia, obesity, locomotor disorders, diarrhea, cachexia, urinary incontinence and as a muscle relaxant, anticonvulsive or anaesthetic and for co-administration with treatment with an opioid analgesic or with an anaesthetic, for diuresis or antinatriuresis, anxiolysis, for modulation of movement activity, for modulation of neurotransmitter secretion and treatment of neurodegenerative diseases associated therewith, for treatment of withdrawal symptoms and/or for reducing the addiction potential of opioids.

In this context, in one of the above uses it may be preferable for a substituted cyclohexylacetic acid derivative used to be in the form of a pure diastereomer and/or enantiomer, a racemate or a non-equimolar or equimolar mixture of the diastereomers and/or enantiomers.

The invention also provides a method for treatment, in particular in one of the abovementioned indications, of a non-human mammal or human which or who requires treatment of pain, in particular chronic pain, by administration of a therapeutically active dose of a substituted cyclohexylacetic acid derivative according to the invention or of a medicament according to the invention.

The invention provides processes for the preparation of substituted cyclohexylacetic acid derivatives.

General Synthesis Equation:

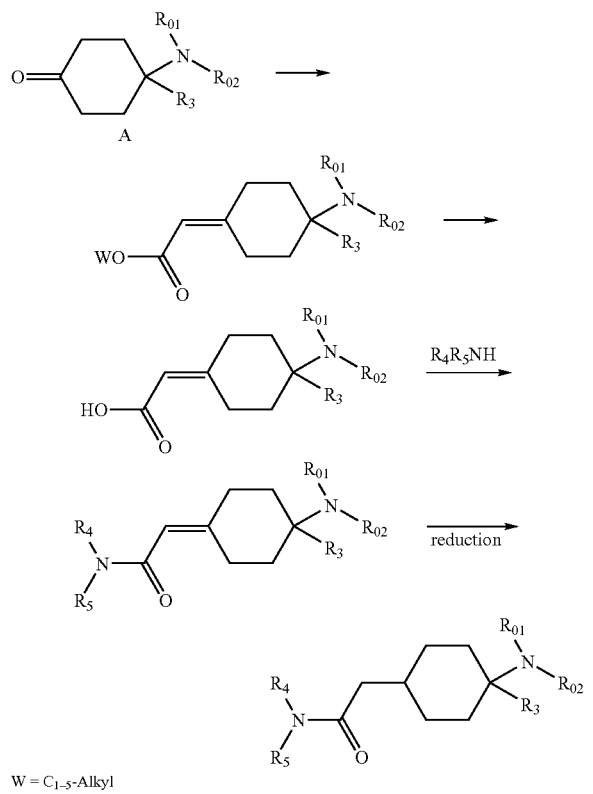

W = $C_{1-5}$-Alkyl $R^{01}$ and $R^{02}$ have the meaning of $R^1$ and $R^2$ and can additionally assume the meaning of a protective group.

The preparation of suitable 4-aminocyclohexanones according to formula A is known from the literature (Lednicer et al., J. Med. Chem., 23, 1980, 424-430; WO 0290317).

A phosphonoacetic acid ester, preferably phosphonoacetic acid trimethyl ester or phosphonoacetic acid triethyl ester, is first reacted with a strong base, preferably potassium tert-butylate, sodium hydride or butyllithium, and then with a 4-aminocyclohexanone according to formula A. In this reaction, for $R_3 \neq$ 2-pyridyl the α,β-unsaturated ester II is formed, and for $R_3$=2-pyridyl the β-hydroxycarboxylic acid ester III is formed.

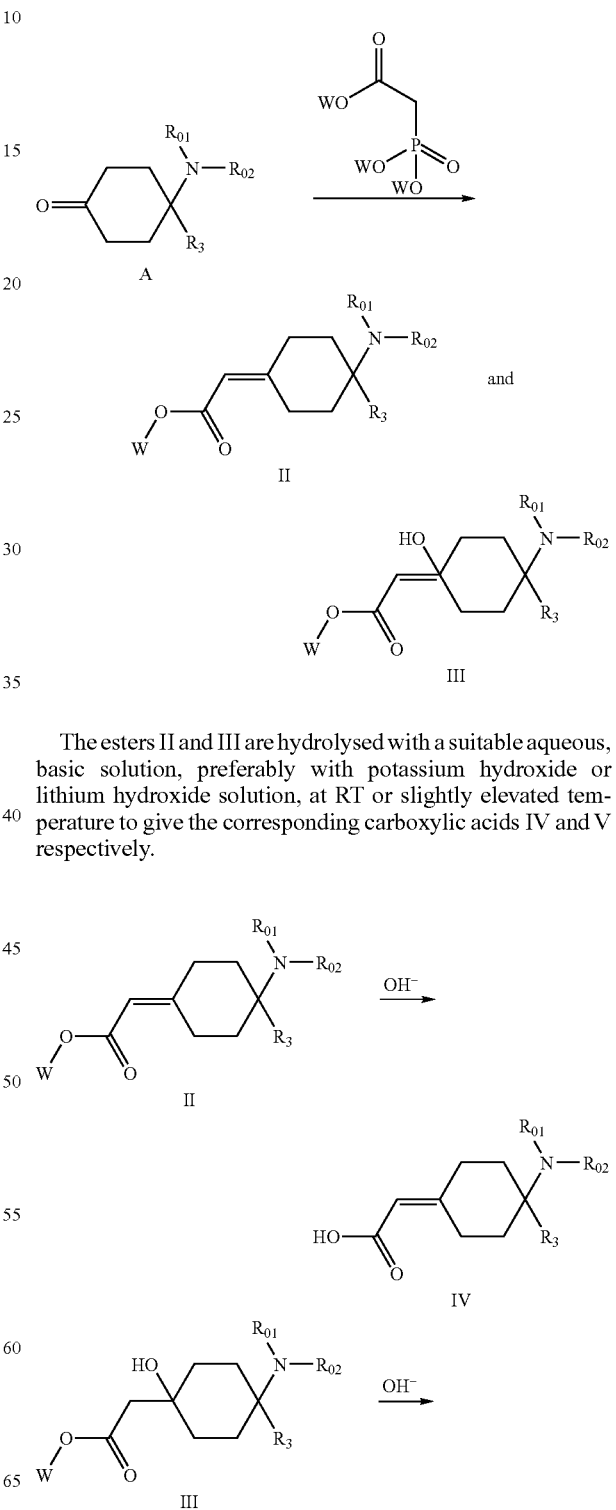

The esters II and III are hydrolysed with a suitable aqueous, basic solution, preferably with potassium hydroxide or lithium hydroxide solution, at RT or slightly elevated temperature to give the corresponding carboxylic acids IV and V respectively.

-continued

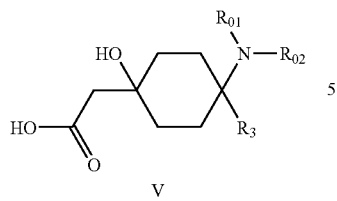

V

The carboxylic acids according to formula IV and V are reacted, as such or as their corresponding hydrochlorides, with a dehydrating reagent, preferably with a carbodiimide, particularly preferably with dicyclohexyl-carbodiimide, in the presence of an activating reagent, preferably with 1-hydroxybenzotriazole, with an amine of the formula $R^4R^5NH$ to give the corresponding amide according to the formula Ia.

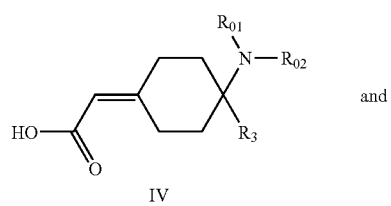

IV and

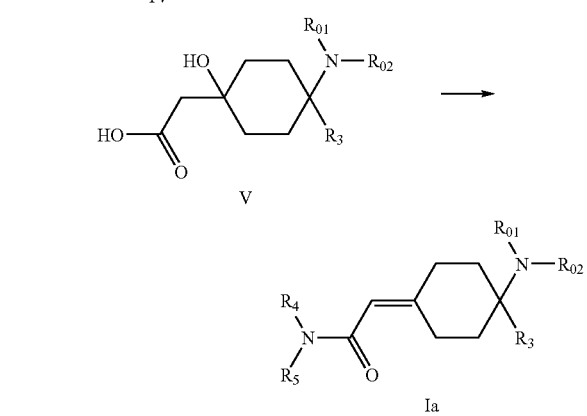

The CC double bond of a cyclohexylidene-acetamide derivative according to formula Ia is optionally reduced by methods known from the literature, preferably by heterogeneous, catalytic hydrogenation on palladium or platinum catalysts or by homogeneous catalysed hydrogen with rhodium catalysts, in each case at temperatures of between RT and 60° C. and under hydrogen pressures of between 1 bar and 6 bar, particularly preferably at RT under a hydrogen pressure of between 2 and 3 bar on palladium-on-charcoal, so that a cyclohexylacetamide derivative according to formula Ib is formed.

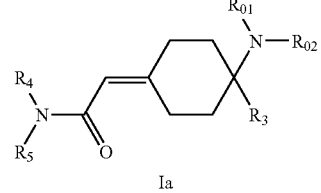

Ia reduction

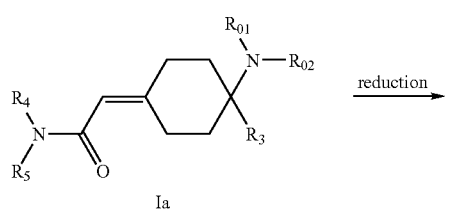

-continued

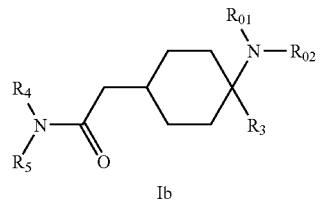

Ib

The double bond can also optionally be reduced at another point in time of the synthesis. In this case, after the first step, the reaction with the phosphonoacetic acid ester, the double bond is reduced by methods known from the literature, preferably by heterogeneous, catalytic hydrogenation on palladium or platinum catalysts or by homogeneous catalysed hydrogenation with rhodium catalysts, in each case at temperatures of between RT and 60° C. and under hydrogen pressures of between 1 bar and 6 bar, particularly preferably at RT under a hydrogen pressure of between 2 and 3 bar on palladium-on-charcoal. The process is then continued with the ester hydrolysis as described above.

In the case where $R^4$ denotes an aryl radical and $R^5$ denotes H, the ester can also be reacted directly in the presence of a strong base, preferably nBuLi, and an aniline to give the compounds according to formula Ic according to the invention.

If appropriate, the protective groups on $R^{01}$ and $R^{02}$ are then split off by methods known to the expert.

Alternative synthesis route:

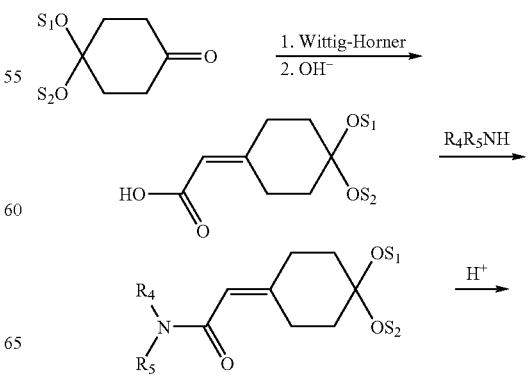

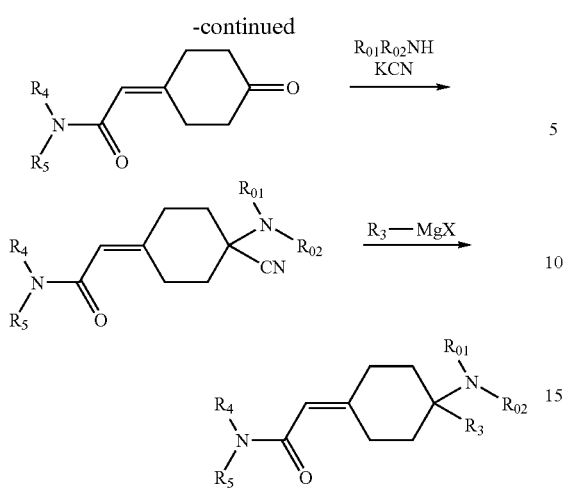

A cyclohexane-1,4-dione according to formula B protected with the groups $S^1$ and $S^2$, which represent protective groups—for example substituted or unsubstituted alkyl, in particular $(CH_2)_n$, where n=2-4—is reacted with a phosphonoacetic acid ester, preferably phosphonoacetic acid trimethyl ester or phosphonoacetic acid triethyl ester, in the presence of a strong base, preferably potassium tert-butylate, sodium hydride or butyllithium. In this reaction, the α,β-unsaturated ester VI is formed.

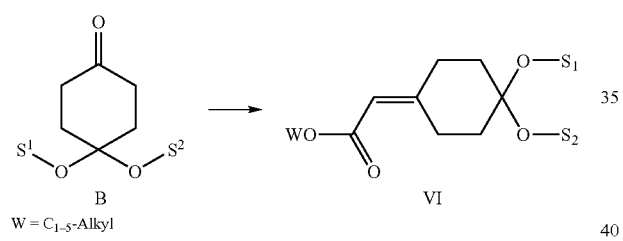

The ester VI is hydrolysed with a suitable aqueous, basic solution, preferably with potassium hydroxide or lithium hydroxide solution, at RT or slightly elevated temperature to give the corresponding carboxylic acid VII.

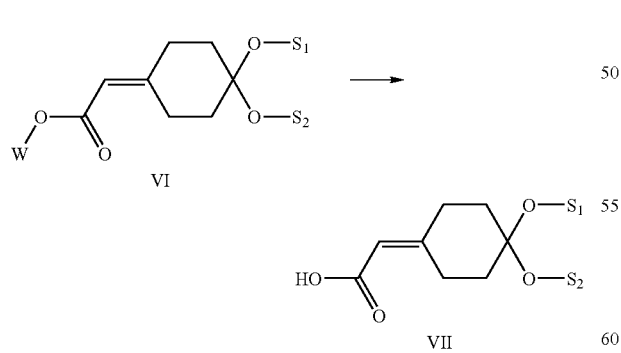

The carboxylic acid according to formula VII is reacted, as such or as its corresponding hydrochloride, with a dehydrating reagent, preferably with a carbodiimide, particularly preferably with dicyclohexyl-carbodiimide, in the presence of an activating reagent, preferably with 1-hydroxybenzotriazole, with an amine of the formula $R^4R^5NH$ to give the corresponding amide according to the formula VIII.

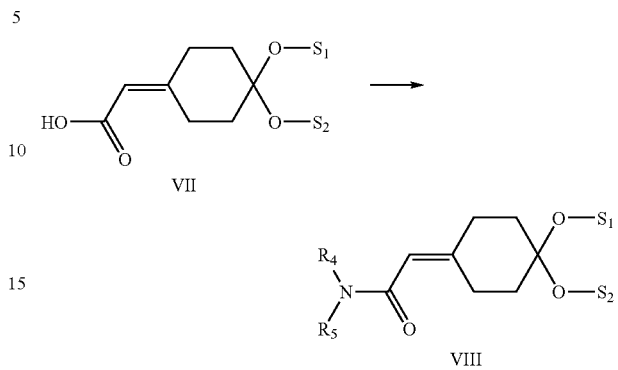

The protective groups $S^1$ and $S^2$ are split off from the compound according to formula VIII, so that a 4-substituted cyclohexanone derivative according to formula IX is formed.

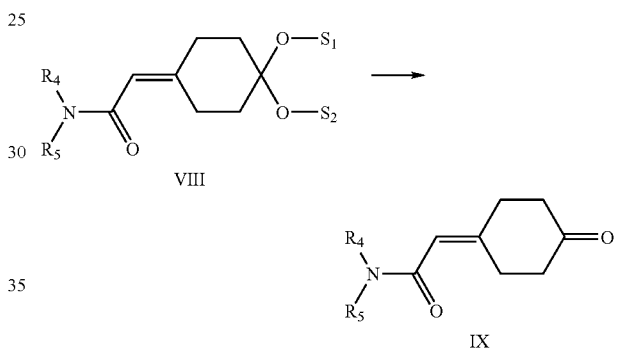

The compound according to formula IX is reacted with a cyanide, preferably potassium cyanide or TMSCN, in the presence of a compound of the formula $HNR^{O1}R^{O2}$ to give a 4-substituted 1-amino-1-cyano-cyclohexane derivative according to formula X.

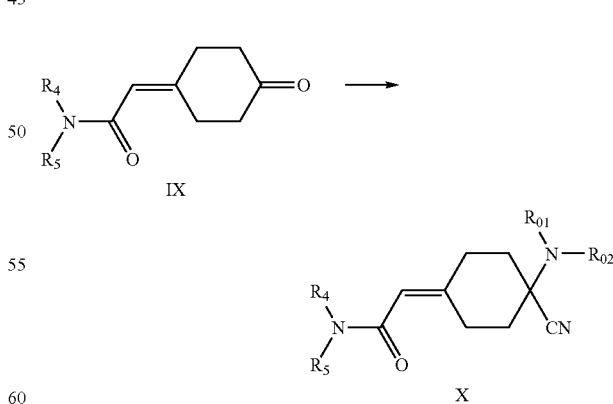

The aminonitrile according to formula X is reacted with organometallic reagents, preferably Grignard or organolithium reagents, of the formula metal-$R^3$ so that the compounds according to formula Ia according to the invention are formed.

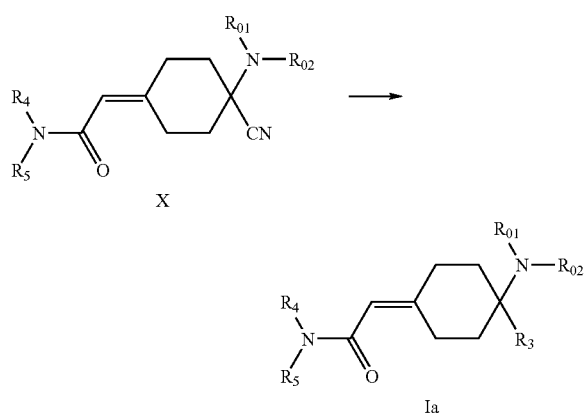

As described in the first synthesis process, compounds of the general formula Ia can then be reduced to compounds of the general formula Ib. Alternatively, in this process the double bond can also be reduced at an earlier point in time, namely compound VIII can be reduced by the methods described in the first synthesis process. The process described is then continued accordingly.

If appropriate, the protective groups on $R^{01}$ and $R^{02}$ are then split off by methods known to the expert.

EXAMPLES

Certain embodiments of the present invention may be further understood by reference to the following specific examples. These examples and the terminology used herein are for the purpose of describing particular embodiments only and are not intended to be limiting.

The yields of the compounds prepared are not optimized.

All the temperatures are uncorrected.

The term "ether" denotes diethyl ether, "EA" denotes ethyl acetate and "MC" denotes methylene chloride. The term "equivalent" means equivalent substance amount, "m.p." denotes melting point or melting range, "decomp." denotes decomposition, "RT" denotes room temperature, "abs." denotes absolute (anhydrous), "rac." denotes racemic, "conc." denotes concentrated, "min" denotes minutes, "h" denotes hours, "d" denotes days, "vol. %" denotes percent by volume, "wt. %" denotes percent by weight and "M" is the concentration stated in mol/l.

Silica gel 60 (0.040-0.063 mm) from E. Merck, Darmstadt was employed as the stationary phase for the column chromatography.

The thin layer chromatography analyses were carried out with HPTLC precoated plates, silica gel 60 F 254 from E. Merck, Darmstadt.

The mixture ratios of mobile phases for chromatographic analyses are always stated in volume/volume.

The compounds employed in the following either were commercially obtainable or their preparation is known from the prior art or has been deduced from the prior art in a manner obvious to the expert.

(4-Dimethylamino-4-phenylcyclohexylidene)acetic acid methyl ester

Phosphonoacetic acid trimethyl ester (1.99 ml, 13.8 mmol) was added to a solution of 4-dimethylamino-4-phenyl-cyclohexanone (2.0 g, 9.2 mmol) in anhydrous DMF (60 ml) under argon. Potassium tert-butylate (1.54 g, 13.8 mmol) was added. The reaction mixture was heated at 60° C. for 4 h and, after cooling, poured on to ice (40 g). After the addition of ether (150 ml) phase separation took place and the aqueous phase was extracted again with ether (2×50 ml). The combined organic phases were dried and concentrated. The methyl ester was obtained here as a yellow oil in a crude yield of 97% (2.42 g).

(4-Dimethylamino-4-phenylcyclohexylidene)acetic acid methyl ester hydrochloride (4-Dimethylamino-4-phenylcyclohexylidene)acetic acid methyl ester (2.4 g, 8.7 mmol) was dissolved in ethyl methyl ketone (70 ml), and chlorotrimethylsilane (1.66 ml, 13.17 mmol) was added, while cooling with ice. After a reaction time of 5 h, it was possible to obtain the hydrochloride of the ester as a colourless solid in a yield of 78% (1.95 g) with an m.p. of 204-208° C.

(4-Dimethylamino-4-phenylcyclohexylidene)acetic acid hydrochloride 1.7 M KOH (70.5 ml, 120 mmol) was added to a solution of (4-dimethylamino-4-phenylcyclohexylidene)acetic acid methyl ester hydrochloride (1.8 g, 5.8 mmol) in ethanol (200 ml) and the mixture was stirred at RT for 16 h. The reaction mixture was concentrated and the residue was taken up in water (40 ml). The aqueous phase was extracted by shaking with ether (2×40 ml), and 5.5 M hydrochloric acid (23.6 ml, 130 mmol) was added. After the aqueous phase had been concentrated, the residue was extracted with ethanol (2×40 ml), the potassium chloride which remained was separated off and the filtrate was concentrated. The hydrochloride of the acid was thereby obtained as a colourless solid in a yield of 98% (1.67 g).

2-(Dimethylamino-4-phenylcyclohexylidene)-N-[2-(1H-indol-3-yl)ethyl]acetamide 1-Hydroxybenzotriazole (182 mg, 1.35 mmol), tryptamine (108 mg, 0.676 mmol) and N-methylmorpholine (0.148 ml, 1.35 mmol) were added to a solution of (4-dimethylamino-4-phenylcyclohexylidene)acetic acid hydrochloride (200 mg, 0.676 mmol) in dry dimethylformamide (10 ml) under argon. The clear solution was cooled to 0° C. and dicyclohexylcarbodiimide (278 mg, 1.35 mmol) was added. The reaction mixture was stirred at RT for 3 d. Working up of the mixture was carried out by separating off the urea which had precipitated out and introducing the filtrate into a mixture of saturated NaCl solution (40 ml) and saturated $NaHCO_3$ solution (10 ml). Still further urea thereby precipitated out and was separated off. The filtrate obtained was extracted with ether. 5 M sodium hydroxide solution (2 ml, 10 mmol) was added to the aqueous phase and the mixture was diluted with water (150 ml). The product thereby precipitated out as a colourless solid in a yield of 31% (84 mg).

2-(Dimethylamino-4-phenylcyclohexylidene)-N-[2-(1H-indol-3-yl)ethyl]acetamide hydrochloride (Example 1)

Chlorotrimethylsilane (0.034 ml, 0.26 mmol) was added to the solution of 2-(dimethylamino-4-phenylcyclohexylidene)-N-[2-(1H-indol-3-yl)ethyl]acetamide (75 mg, 0.178 mmol) in ethyl methyl ketone (15 ml). After 2 h it was pos-

2-[2-(4-Dimethylamino-4-phenylcyclohexylidene)acetylamino]-3-(1H-indol-3-yl)propanoic acid methyl ester 1-Hydroxybenzotriazole (182 mg, 1.35 mmol), L-tryptophan methyl ester hydrochloride (172 mg, 0.676 mmol) and N-methyl-morpholine (0.148 ml, 1.35 mmol) were added to a solution of (4-dimethylamino-4-phenylcyclohexylidene)acetic acid hydrochloride (200 mg, 0.676 mmol) in dimethylformamide (10 ml) under argon. The solution was cooled to 0° C. and dicyclohexylcarbodiimide (278 mg, 1.35 mmol) was added. The reaction mixture was stirred at RT for 6 d. Working up of the mixture was carried out by separating off the urea which had precipitated out and introducing the filtrate into a mixture of saturated NaCl solution (40 ml) and saturated NaHCO$_3$ solution (10 ml). Still further urea thereby precipitated out and was separated off. The filtrate obtained was extracted with ether. The organic phase was concentrated, the crude product being obtained as a yellow oil (142 mg).

2-[2-(4-Dimethylamino-4-phenylcyclohexylidene)acetylamino]-3-(1H-indol-3-yl)propanoic acid methyl ester hydrochloride (less polar diastereoisomer; Example 2)

2-[2-(4-Dimethylamino-4-phenylcyclohexylidene)acetylamino]-3-(1H-indol-3-yl)propanoic acid methyl ester (142 mg, 0.3 mmol) was dissolved in ethyl methyl ketone (9 ml), and chlorotrimethylsilane (0.055 ml, 0.43 mmol) was added. After 2 h it was possible to obtain the product as a colourless compound in a yield of 50 mg (15%) with an m.p. of 164-168° C.

(4-Dimethylamino-4-phenylcyclohexylidene)acetic acid 2,5-dioxo-pyrrolidin-1-yl ester (4-Dimethylamino-4-phenylcyclohexylidene)acetic acid hydrochloride (200 mg, 0.676 mmol) was dissolved in methylene chloride (10 ml), and triethylamine (0.28 ml, 2.0 mmol) and N,N'-di(succinimidyl)carbonate (345 mg, 1.35 mmol) were added under argon. After a reaction time of 24 h, the reaction mixture was concentrated, the residue was taken up in ether (20 ml) and the mixture was extracted with saturated NaHCO$_3$ solution (2×5 ml). After the organic phase had been dried and concentrated, the product was obtained as a colourless oil in a yield of 52% (124 mg).

(2S)-2-[(RS)-2-(4-Dimethylamino-4-phenylcyclohexylidene)-acetylamino]-3-(1H-indol-3-yl)propanoic acid methyl ester First L-tryptophan methyl ester (3.74 mg, 0.29 mmol) and then triethylamine (0.071 ml, 0.5 mmol) were added to a solution of (4-dimethylamino-4-phenylcyclohexylidene)acetic acid 2,5-dioxo-pyrrolidin-1-yl ester (104 mg, 0.29 mmol) in acetonitrile (10 ml) under argon. The reaction mixture was stirred at RT for 2 d and then concentrated and the residue was taken up in ether (30 ml). The organic phase was extracted by shaking with saturated NaHCO$_3$ solution (2×10 ml) and, after drying, was concentrated. The crude product was thereby obtained as a colourless oil in a yield of 92 mg (69%). It was possible to isolate the hydrochloride as a beige-coloured solid in a yield of 75% (61 mg) with an m.p. of 203-207° C.

(2S)-2-[(RS)-2-(4-Dimethylamino-4-phenylcyclohexylidene)-acetylamino]-3-(1H-indol-3-yl)propanoic acid methyl ester hydrochloride (more polar diastereoisomer; Example 3)

Chlorotrimethylsilane (0.038 ml, 0.3 mmol) was added to a solution of (2S)-2-[(RS)-2-(4-dimethylamino-4-phenylcyclohexylidene)acetylamino]-3-(1H-indol-3-yl)propanoic acid methyl ester (92 mg, 0.2 mmol) in ethyl methyl ketone (3 ml) and the mixture was stirred at RT for 2 h. The product (43 mg, 43%) with an m.p. of 193-195° C. thereby precipitated out as a colourless solid. The substance proved to be the more polar of two possible diastereoisomers.

2-(4-Dimethylamino-4-phenylcyclohexylidene)-N-[2-(1H-indol-3-yl)-1-methylethyl]acetamide 1-Hydroxybenzotriazole (456 mg, 3.38 mmol), DL-α-methyltryptamine (0.142 ml, 1.69 mmol) and N-methylmorpholine (0.375 ml, 3.38 mmol) were added to a solution of (4-dimethylamino-4-phenylcyclohexylidene)acetic acid hydrochloride (500 mg, 1.69 mmol) in dry dimethylformamide (10 ml) under argon. The solution was cooled to 0° C. and dicyclohexylcarbodiimide (687 mg, 3.38 mmol) was added. The reaction mixture was stirred at RT for 6 d. Working up of the mixture was carried out by separating off the urea which had precipitated out and introducing the filtrate into a mixture of saturated NaCl solution (40 ml) and saturated NaHCO$_3$ solution (10 ml). Still further urea thereby precipitated out and was separated off. 5 M sodium hydroxide solution (2 ml, 10 mmol) was added to the filtrate and the mixture was diluted with water (200 ml). The product thereby precipitated out as a beige-coloured solid and was to be obtained in a yield of 83% (581 mg). Separation by chromatography on silica gel was carried out with EA/methanol (15:1), (10:1) and (5:1). The less polar diastereoisomer of 2-(4-dimethylamino-4-phenylcyclohexylidene)-N-[2-(1H-indol-3-yl)-1-methylethyl]acetamide were thereby obtained as a colourless solid with an m.p. of 184-187° C. in a yield of 24% (165 mg). It was possible to isolate the more polar diastereoisomer of 2-(4-dimethylamino-4-phenylcyclohexylidene)-N-[2-(1H-indol-3-yl)-1-methylethyl]acetamide as a colourless oil in a yield of 18% (126 mg).—Both amides were diastereoisomerically pure.

2-(4-Dimethylamino-4-phenylcyclohexylidene)-N-[2-(1H-indol-3-yl)-1-methylethyl]acetamide hydrochloride (Examples 4 and 5)

The less polar diastereoisomer of 2-(4-Dimethylamino-4-phenylcyclohexylidene)-N-[2-(1H-indol-3-yl)-1-methylethyl]acetamide (156 mg, 0.397 mmol) was dissolved in ethyl methyl ketone (11 ml) with gentle heating, and chlorotrimethylsilane (0.075 ml, 0.59 mmol) was added. After 1.5 h it was possible to isolate the hydrochloride (Example 4) as a colourless solid in a yield of 55% (96 mg) with an m.p. of 175-180° C.

Chlorotrimethylsilane (0.06 ml, 0.48 mmol) was added to a solution of the more polar diastereoisomer of 2-(4-dimethylamino-4-phenylcyclohexylidene)-N-[2-(1H-indol-3-yl)-1-methylethyl]acetamide (133 mg, 0.32 mmol) in ethyl methyl ketone (5 ml) and the mixture was stirred at RT for 1.5 h. The hydrochloride (Example 5) (66 mg, 46%) thereby precipitated out as a colourless solid with an m.p. of 182-186° C.

2-(4-Dimethylamino-4-phenylcyclohexylidene)-N-(3-phenyl-propyl)acetamide

1-Hydroxybenzotriazole (273 mg, 2.0 mmol), 3-phenyl-1-propylamine (0.142 ml, 1.0 mmol) and N-methylmorpholine (0.222 ml, 2.0 mmol) were added to a solution of (4-dimethylamino-4-phenylcyclohexylidene)acetic acid hydrochloride (300 mg, 1.0 mmol) in dry dimethylformamide (10 ml) under argon. The solution was cooled to 0° C. and dicyclohexylcarbodiimide (417 mg, 2.0 mmol) was added. The reaction mixture was stirred at RT for 3 d. Working up of the mixture was carried out by separating off the urea which had precipitated out and introducing the filtrate into a mixture of saturated NaCl solution (40 ml) and saturated NaHCO$_3$ solution (10 ml). Still further urea thereby precipitated out and was separated off. The filtrate obtained was extracted with ether. 5 M sodium hydroxide solution (2 ml, 10 mmol) was added to the aqueous phase and the mixture was diluted with water (200 ml). The product thereby precipitated out as a colourless solid and was to be obtained in a yield of 55% (209 mg) with an m.p. of 140-142° C.

2-(4-Dimethylamino-4-phenylcyclohexylidene)-N-(3-phenyl-propyl)acetamide hydrochloride (Example 6)

2-(4-Dimethylamino-4-phenylcyclohexylidene)-N-(3-phenyl-propyl)acetamide (203 mg, 0.536 mmol) was dissolved in ethyl methyl ketone (12 ml) with gentle heating and chlorotrimethylsilane (0.101 ml, 0.8 mmol) was added. After 2 h it was possible to isolate the product as a colourless solid in a yield of 95% (211 mg) with an m.p. of 225-230° C.

2-(4-Dimethylamino-4-phenylcyclohexylidene)-N-phenylethyl-acetamide

1-Hydroxybenzotriazole (273 mg, 2.0 mmol), 2-phenylethylamine (0.125 ml, 1.0 mmol) and N-methylmorpholine (0.222 ml, 2.0 mmol) were added to a solution of (4-dimethylamino-4-phenylcyclohexylidene)acetic acid hydrochloride (296 mg, 1.0 mmol) in dry dimethylformamide (10 ml) under argon. The solution was cooled to 0° C. and dicyclohexylcarbodiimide (417 mg, 2.0 mmol) was added. The reaction mixture was stirred at RT for 10 d. Working up of the mixture was carried out by separating off the urea which had precipitated out and introducing the filtrate into a mixture of saturated NaCl solution (40 ml) and saturated NaHCO$_3$ solution (10 ml). Still further urea thereby precipitated out and was separated off. 5 M sodium hydroxide solution (4 ml, 20 mmol) was added to the aqueous phase and the mixture was diluted with water (300 ml) and stored at 5° C. for 3 d. The product thereby precipitated out as a colourless solid in a yield of 62% (223 mg) and with an m.p. of 153-155° C.

2-(4-Dimethylamino-4-phenylcyclohexylidene)-N-phenylethyl-acetamide hydrochloride (Example 7)

2-(4-Dimethylamino-4-phenylcyclohexylidene)-N-phenylethylacetamide (225 mg, 0.62 mmol) was dissolved in ethyl methyl ketone (12 ml) with gentle heating and chlorotrimethylsilane (0.118 ml, 0.93 mmol) was added. After 2 h the product was isolated as a colourless solid in a yield of 86% (213 mg).

N-Benzyl-2-(4-dimethylamino-4-phenylcyclohexylidene)-acetamide

1-Hydroxybenzotriazole (273 mg, 2.0 mmol), benzylamine (0.109 ml, 1.0 mmol) and N-methylmorpholine (0.222 ml, 2.0 mmol) were added to a solution of (4-dimethylamino-4-phenylcyclohexylidene)acetic acid hydrochloride (296 mg, 1.0 mmol) in dry dimethylformamide (10 ml) under argon. The solution was cooled to 0° C. and dicyclohexylcarbodiimide (417 mg, 2.0 mmol) was added. The reaction mixture was stirred at RT for 12 d. Working up of the mixture was carried out by separating off the urea which had precipitated out and introducing the filtrate into a mixture of saturated NaCl solution (40 ml) and saturated NaHCO$_3$ solution (10 ml). Still further urea thereby precipitated out and was separated off. 5 M sodium hydroxide solution (4 ml, 20 mmol) was added to the aqueous phase and the mixture was diluted with water (300 ml) and stored at 5° C. for 3 d. The product thereby precipitated out as a colourless solid in a yield of 65% (227 mg) and with an m.p. of 145-148° C.

N-Benzyl-2-(4-dimethylamino-4-phenylcyclohexylidene)-acetamide hydrochloride (Example 8)

N-Benzyl-2-(4-dimethylamino-4-phenylcyclohexylidene)acetamide (206 mg, 0.59 mmol) was dissolved in ethyl methyl ketone (12 ml), and chlorotrimethylsilane (0.112 ml, 0.88 mmol) was added. After 2 h the hydrochloride (Example 8) was isolated as a colourless solid with an m.p. of 220-226° C. and a yield of 99% (225 mg).

2-(4-Dimethylamino-4-phenylcyclohexylidene)-N-(4-phenyl-butyl)acetamide

1-Hydroxybenzotriazole (273 mg, 2.0 mmol), 4-phenylbutylamine (0.158 ml, 1.0 mmol) and N-methylmorpholine (0.222 ml, 2.0 mmol) were added to a solution of (4-dimethylamino-4-phenylcyclohexylidene)acetic acid hydrochloride (296 mg, 1.0 mmol) in dry dimethylformamide (10 ml) under argon. The solution was cooled to 0° C. and dicyclohexylcarbodiimide (417 mg, 2.0 mmol) was added. The reaction mixture was stirred at RT for 5 d. Working up of the mixture was carried out by separating off the urea which had precipitated out and introducing the filtrate into a mixture of saturated NaCl solution (40 ml) and saturated NaHCO$_3$ solution (10 ml). Still further urea thereby precipitated out and was separated off 5 M sodium hydroxide solution (4 ml, 20 mmol) was added to the aqueous phase and the mixture was diluted with water (300 ml) and stored at 5° C. for 16 h. The product thereby precipitated out as a colourless oily compound in a yield of 75% (294 mg).

2-(4-Dimethylamino-4-phenylcyclohexylidene)-N-(4-phenyl-butyl)acetamide hydrochloride (Example 9)

2-(4-Dimethylamino-4-phenylcyclohexylidene)-N-(4-phenyl-butyl)acetamide (292 mg, 0.747 mmol) was dissolved in ethyl methyl ketone (5 ml), and chlorotrimethylsilane (0.14 ml, 1.12 mmol) was added. After 1.5 h the hydrochloride was isolated as a colourless solid in a yield of 69% (221 mg).

2-(4-Dimethylamino-4-phenylcyclohexylidene)-N-(4-fluoro-phenyl)acetamide

1-Hydroxybenzotriazole (273 mg, 2.0 mmol), 4-fluoroaniline (0.095 ml, 1.0 mmol) and N-methylmorpholine (0.222 ml, 2.0 mmol) were added to a solution of (4-dimethylamino-4-phenylcyclohexylidene)acetic acid hydrochloride (296 mg, 1.0 mmol) in dry dimethylformamide (10 ml) under argon. The solution was cooled to 0° C. and dicyclohexylcarbodiimide (417 mg, 2.0 mmol) was added. The reaction mixture was stirred at RT for 7 d. Working up of the mixture was carried out by separating off the urea which had precipitated out and introducing the filtrate into a mixture of saturated NaCl solution (40 ml) and saturated NaHCO$_3$ solution (10 ml). Still further urea thereby precipitated out and was separated off. 5 M sodium hydroxide solution (4 ml, 20 mmol) was added to the aqueous phase and the mixture was diluted with water (300 ml) and stored at 5° C. for 3 d. The product thereby precipitated out as a colourless solid in a yield of 82% (287 mg).

2-(4-Dimethylamino-4-phenylcyclohexylidene)-N-(4-fluoro-phenyl)acetamide hydrochloride (Example 10)

2-(4-Dimethylamino-4-phenylcyclohexylidene)-N-(4-fluoro-phenyl)acetamide (266 mg, 0.755 mmol) was dissolved in ethyl methyl ketone (5 ml), and chlorotrimethylsilane (0.139 ml, 1.1 mmol) was added. After 2.5 h the hydrochloride was isolated as a colourless solid in a yield of 52% (152 mg).

2-(4-Dimethylamino-4-phenylcyclohexylidene)-N-(4-fluoro-benzyl)acetamide

1-Hydroxybenzotriazole (273 mg, 2.0 mmol), 4-fluorobenzylamine (0.114 ml, 1.0 mmol) and N-methylmorpholine (0.222 ml, 2.0 mmol) were added to a solution of (4-dimethylamino-4-phenylcyclohexylidene) acetic acid hydrochloride (296 mg, 1.0 mmol) in dry dimethylformamide (10 ml) under argon. The solution was cooled to 0° C. and dicyclohexylcarbodiimide (417 mg, 2.0 mmol) was added. The reaction mixture was stirred at RT for 12 d. Working up of the mixture was carried out by separating off the urea which had precipitated out and introducing the filtrate into a mixture of saturated NaCl solution (40 ml) and saturated NaHCO$_3$ solution (10 ml). Still further urea thereby precipitated out and was separated off. 5 M sodium hydroxide solution (4 ml, 20 mmol) was added to the aqueous phase and the mixture was diluted with water (300 ml) and stored at 5° C. for 16 h. The product thereby precipitated out as a colourless solid in a yield of 75% (275 mg) and with an m.p. of 149-151° C.

2-(4-Dimethylamino-4-phenylcyclohexylidene)-N-(4-fluoro-benzyl)acetamide hydrochloride (Example 11)

2-(4-Dimethylamino-4-phenylcyclohexylidene)-N-(4-fluorobenzyl)acetamide (252 mg, 0.688 mmol) was dissolved in ethyl methyl ketone (10 ml) with gentle heating and chlorotrimethylsilane (0.126 ml, 1.0 mmol) was added. After 2.5 h the hydrochloride was isolated as a colourless solid with an m.p. of 214-218° C. and a yield of 71% (196 mg).

2-(4-Dimethylamino-4-phenylcyclohexylidene)-N-[2-(4-fluorophenyl)ethyl]acetamide 1-Hydroxybenzotriazole (273 mg, 2.0 mmol), 2-(4-fluorophenyl)ethylamine (0.131 ml, 1.0 mmol) and N-methylmorpholine (0.222 ml, 2.0 mmol) were added to a solution of (4-dimethylamino-4-phenylcyclohexylidene) acetic acid hydrochloride (296 mg, 1.0 mmol) in dry dimethylformamide (10 ml) under argon. The solution was cooled to 0° C. and dicyclohexylcarbodiimide (417 mg, 2.0 mmol) was added. The reaction mixture was stirred at RT for 6 d. Working up of the mixture was carried out by separating off the urea which had precipitated out and introducing the filtrate into a mixture of saturated NaCl solution (40 ml) and saturated NaHCO$_3$ solution (10 ml). Still further urea thereby precipitated out and was separated off. 5 M sodium hydroxide solution (4 ml, 20 mmol) was added to the aqueous phase and the mixture was diluted with water (300 ml) and stored at 5° C. for 16 h. The product thereby precipitated out as a colourless oily compound in a yield of 66% (252 mg).

2-(4-Dimethylamino-4-phenylcyclohexylidene)-N-[2-(4-fluorophenyl)ethyl]acetamide hydrochloride (Example 12)

2-(4-Dimethylamino-4-phenylcyclohexylidene)-N-[2-(4-fluorophenyl)ethyl]acetamide (252 mg, 0.66 mmol) was dissolved in ethyl methyl ketone (5 ml), and chlorotrimethylsilane (0.126 ml, 1.0 mmol) was added. After 2 h the hydrochloride was isolated as a colourless solid with an m.p. of 157-160° C. and a yield of 74% (203 mg).

2-(4-Dimethyl-4-phenylcyclohexylidene)-N-(2-trifluoro-methylbenzyl)acetamide

1-Hydroxybenzotriazole (432 mg, 3.2 mmol), 2-(trifluoromethyl)benzylamine (0.225 ml, 1.6 mmol) and N-methylmorpholine (0.355 ml, 3.2 mmol) were added to a solution of (4-dimethylamino-4-phenylcyclohexylidene) acetic acid hydrochloride (475 mg, 1.6 mmol) in dry dimethylformamide (10 ml) under argon. The solution was cooled to 0° C. and dicyclohexylcarbodiimide (660 mg, 3.2 mmol) was added. The reaction mixture was stirred at RT for 6 d. Working up of the mixture was carried out by separating off the urea which had precipitated out and introducing the filtrate into a mixture of saturated NaCl solution (40 ml) and saturated NaHCO$_3$ solution (10 ml). Still further urea thereby precipitated out and was separated off. 5 M sodium hydroxide solution (4 ml, 20 mmol) was added to the aqueous phase and the mixture was diluted with water (300 ml) and stored at 5° C. for 4 d. The product thereby precipitated out as a beige-coloured solid in a yield of 70% (465 mg).

2-(4-Dimethylamino-4-phenylcyclohexylidene)-N-(2-trifluoro-methylbenzyl)acetamide hydrochloride (Example 13)

2-(4-Dimethylamino-4-phenylcyclohexylidene)-N-(2-trifluoromethyl-benzyl)acetamide (432 mg, 1.03 mmol) was dissolved in ethyl methyl ketone (7 ml), and chlorotrimethylsilane (0.195 ml, 1.5 mmol) was added. After 2 h the hydrochloride was isolated as a colourless solid with an m.p. of 133-136° C. and a yield of 89% (415 mg).

2-(4-Dimethylamino-4-phenylcyclohexylidene)-N-(1H-indol-3-ylmethyl)acetamide

1-Hydroxybenzotriazole (459 mg, 3.4 mmol), C-(1H-indol-3-yl)methylamine (2.249 mg, 1.7 mmol) and N-methylmorpholine (0.377 ml, 3.4 mmol) were added to a solution of (4-dimethylamino-4-phenylcyclohexylidene)acetic acid hydrochloride (499 mg, 1.7 mmol) in dry dimethylformamide (10 ml) under argon. The solution was cooled to 0° C. and dicyclohexylcarbodiimide (708 mg, 3.4 mmol) was added. The reaction mixture was stirred at RT for 5 d. Working up of the mixture was carried out by separating off the urea which had precipitated out and introducing the filtrate into a mixture of saturated NaCl solution (40 ml) and saturated NaHCO$_3$ solution (10 ml). Still further urea thereby precipitated out and was separated off. 5 M sodium hydroxide solution (4 ml, 20 mmol) was added to the aqueous phase and the mixture was diluted with water (300 ml) and stored at 5° C. for 16 h.

The crude product thereby precipitated out (253 mg) and was purified by chromatography on silica gel with EA/methanol (4:1) and methanol. The product was obtained as an oily compound in a yield of 18% (120 mg).

2-(4-Dimethylamino-4-phenylcyclohexylidene)-N-(1H-indol-3-ylmethyl)acetamide hydrochloride (Example 14)

2-(4-Dimethylamino-4-phenylcyclohexylidene)-N-(1H-indol-3-ylmethyl)acetamide (120 mg, 0.309 mmol) was dissolved in ethyl methyl ketone (5 ml), and chlorotrimethylsilane (0.058 ml, 0.46 mmol) was added. After 1.5 h the hydrochloride was isolated with an m.p. of 173-185° C. in a yield of 63% (82 mg).

2-(4-Dimethylamino-4-phenylcyclohexylidene)-N-[4-(1H-indol-3-yl)butyl]acetamide 1-Hydroxybenzotriazole (546 mg, 4.0 mmol), 4-(1H-indol-3-yl)butylamine (2.376 mg, 2.0 mmol) and N-methylmorpholine (0.444 ml, 4.0 mmol) were added to a solution of (4-dimethylamino-4-phenylcyclohexylidene)acetic acid hydrochloride (592 mg, 2.0 mmol) in dry dimethylformamide (10 ml) under argon. The clear solution was cooled to 0° C. and dicyclohexylcarbodiimide (834 mg, 4.0 mmol) was added. The reaction mixture was stirred at RT for 4 d. Working up of the mixture was carried out by separating off the urea which had precipitated out and introducing the filtrate into a mixture of saturated NaCl solution (40 ml) and saturated $NaHCO_3$ solution (10 ml). Still further urea thereby precipitated out and was separated off. 5 M sodium hydroxide solution (5 ml, 25 mmol) was added to the aqueous phase and the mixture was diluted with water (300 ml) and stored at 5° C. for 16 h. The product thereby precipitated out as a colourless solid in a yield of 45% (387 mg) with an m.p. of 77-88° C.

2-(4-Dimethylamino-4-phenylcyclohexylidene)-N-[4-(1H-indol-3-yl)butyl]acetamide hydrochloride (Example 15)

2-(4-Dimethylamino-4-phenylcyclohexylidene)-N-[4-(1H-indol-3-yl)butyl]acetamide (184 mg, 0.428 mmol) was dissolved in ethyl methyl ketone (10 ml), and chlorotrimethylsilane (0.08 ml, 0.64 mmol) was added. After 1.5 h the hydrochloride was isolated as a colourless solid with an m.p. of 185-188° C. in a yield of 74% (147 mg).

2-(4-Dimethylamino-4-phenylcyclohexylidene)-N-[3-(1H-indol-3-yl)propyl]acetamide 1-Hydroxybenzotriazole (819 mg, 6.0 mmol), 3-(1H-indol-3-yl)propylamine (522 mg, 3.0 mmol) and N-methylmorpholine (0.666 ml, 6.0 mmol) were added to a solution of (4-dimethylamino-4-phenylcyclohexylidene)acetic acid hydrochloride (887 mg, 3.0 mmol) in dry dimethylformamide (10 ml) under argon. The solution was cooled to 0° C. and dicyclohexylcarbodiimide (1.25 g, 6.0 mmol) was added. The reaction mixture was stirred at RT for 6 d. Working up of the mixture was carried out by separating off the urea which had precipitated out and introducing the filtrate into a mixture of saturated NaCl solution (40 ml) and saturated $NaHCO_3$ solution (10 ml). Still further urea thereby precipitated out and was separated off. The aqueous phase was diluted with water (400 ml), 5 M sodium hydroxide solution (5 ml, 25 mmol) was added and the mixture was stored at 5° C. for 3 d. The product thereby precipitated out as a beige-coloured solid in a yield of 60% (742 mg) with an m.p. of 85-87° C.

2-(4-Dimethylamino-4-phenylcyclohexylidene)-N-[3-(1H-indol-3-yl)propyl]acetamide hydrochloride (Example 16)

2-(4-Dimethylamino-4-phenylcyclohexylidene)-N-[3-(1H-indol-3-yl)propyl]acetamide (742 mg, 1.78 mmol) was dissolved in ethyl methyl ketone (25 ml), and chlorotrimethylsilane (0.34 ml, 2.7 mmol) was added. After 2 h the hydrochloride was isolated as a beige-coloured solid with an m.p. of 165-173° C. in a yield of 75% (606 mg).

5-(1H-Indol-3-yl)pentanoic acid cyanomethyl ester 5-(1H-Indol-3-yl)pentanoic acid (5 g, 23 mmol) was dissolved in a mixture of acetone (25 ml) and dimethylformamide (25 ml), and caesium carbonate (3.75 g, 11.5 mmol), chloroacetonitrile (2.16 ml, 34.5 mmol) and potassium iodide (20 mg) were added in succession. After 6.5 h at 60° C. and 16 h at RT, the solid residues were filtered off and washed with acetone (2×30 ml) and the filtrate was concentrated. The crude product was purified by chromatography on silica gel (130 g) with EA/cyclohexane (1:3). The product was obtained as a colourless solid with an m.p. of 76° C. in a yield of 77% (4.53 g).

5-(1-H-Indol-3-yl)pentanoic acid amide

A solution of 5-(1H-indol-3-yl)pentanoic acid cyanomethyl ester (4.5 g, 17.5 mmol) in tetrahydrofuran (110 ml) was added to a 25 percent strength ammonia solution (80 ml) and the mixture was stirred at room temperature for 3 d. Working up of the mixture was carried out by phase separation and extraction of the aqueous phase with tetrahydrofuran (2×30 ml). The organic phases were combined, washed with saturated sodium chloride solution (50 ml), dried and concentrated. The residue was washed with water (2×10 ml) and ether (2×10 ml) and dried. The product remained as a colourless solid in a yield of 68% (2.56 g) with an m.p. of 134-139° C.

5-(1H-Indol-3-yl)pentylamine

Lithium aluminium hydride (0.87 g, 23.0 mmol) was added to abs. tetrahydrofuran (70 ml) under argon. A solution of 5-(1H-indol-3-yl)pentanoic acid amide (2.5 g, 11.5 mmol) in abs. tetrahydrofuran (60 ml) was added to the $LiAlH_4$ suspension at 60° C. After 12 h at 60° C., tetrahydrofuran (30 ml) was added to the mixture and hydrolysis was carried out, while cooling with ice. The aluminium compounds thereby obtained were separated off by filtration and washed with tetrahydrofuran (3×10 ml). The filtrate was concentrated. After addition of water (30 ml), the amine was extracted with EA (3×40 ml) and the extracts were combined and washed with water (40 ml). After drying and concentration of the organic phase, the product was obtained as a colourless solid in a yield of 95% (2.21 g) with an m.p. of 69-78° C.

2-(4-Dimethylamino-4-phenylcyclohexylidene)-N-[5-(1H-indol-3-yl)pentyl]acetamide 1-Hydroxybenzotriazole (819 mg, 6.0 mmol), 5-(1H-indol-3-yl)pentylamine (606 mg, 3.0 mmol) and N-methylmorpholine (0.666 ml, 6.0 mmol) were added to a solution of (4-dimethylamino-4-phenylcyclohexylidene)acetic acid hydrochloride (887 mg, 3.0 mmol) in dry dimethylformamide (10 ml) under argon. The solution was cooled to 0° C. and dicyclohexylcarbodiimide (1.25 g, 6.0 mmol) was added. The reaction mixture was stirred at RT for 4 d. Working up of the mixture was carried out by separating off the urea which had precipitated out and introducing the filtrate into a mixture of saturated NaCl solution (40 ml) and saturated NaHCO$_3$ solution (10 ml). Still further urea thereby precipitated out and was separated off. The aqueous phase was diluted with water (300 ml), 5 M sodium hydroxide solution (7 ml, 35 mmol) was added and the mixture was stored at 5° C. for 3 d. The crude product thereby precipitated out as a beige-coloured solid in a yield of 69% (915 mg). After chromatography on silica gel (50 mg) with EA/methanol (1:1) and methanol, the product was isolated as a colourless solid (333 mg) with an m.p. of 68-72° C. in a yield of 25%.

2-(4-Dimethylamino-4-phenylcyclohexylidene)-N-[5-(1H-indol-3-yl)pentyl]acetamide hydrochloride (Example 17)

2-(4-Dimethylamino-4-phenylcyclohexylidene)-N-[5-(1H-indol-3-yl)pentyl]acetamide (81 mg, 0.182 mmol) was dissolved in ethyl methyl ketone (3 ml), and chlorotrimethylsilane (0.035 ml, 0.27 mmol) was added. After 1.5 h the hydrochloride was isolated as a colourless solid with an m.p. of 174-183° C. in a yield of 71% (62 mg).

6-(1H-Indol-3-yl)hexanoic acid cyanomethyl ester 6-(1H-Indol-3-yl)-hexanoic acid (6.01 g, 26.0 mmol) was dissolved in acetone (30 ml) and DMF (30 ml), and caesium carbonate (4.23 g, 13.0 mmol), chloroacetonitrile (2.45 ml, 39.0 mmol) and potassium iodide (20 mg) were added in succession. After a reaction time of 9 h at 60° C. and 60 h at RT, the solid residues were separated off by filtration and washed with acetone (2×10 ml) and the filtrate was concentrated. The crude product was purified by chromatography on silica gel (150 g) with EA/cyclohexane (1:3). The cyanomethyl ester was obtained as a colourless solid with an m.p. of 74-76° C. in a yield of 82% (5.76 g).

6-(1H-Indol-3-yl)hexanoic acid amide

A solution of 6-(1H-Indol-3-yl)hexanoic acid cyanomethyl ester (5.72 g, 21.16 mmol) in tetrahydrofuran (160 ml) was added to a 25 percent strength ammonia solution (125 ml) and the mixture was stirred at RT for 40 h. Working up of the mixture was carried out by phase separation and extraction of the aqueous phase with THF (2×40 ml). The organic extracts were combined and washed with saturated NaCl solution (50 ml). After drying and concentration of the organic phase, the product was isolated as a colourless solid in a yield of 98% (4.75 g) with an m.p. of
140-142 C.

6-(1H-Indol-3-yl)hexylamine

Lithium aluminium hydride (1.7 g, 40.8 mmol) was added to abs. tetrahydrofuran (80 ml) under argon. A solution of 6-(1H-indol-3-yl)hexanoic acid amide (4.7 g, 20.4 mmol) in abs. tetrahydrofuran (100 ml) was added to the LiAlH$_4$ suspension at 60° C. in the course of 40 min, while stirring. After a reaction time of 13 h at 60° C. under argon, tetrahydrofuran (50 ml) was added to the mixture, and water (42 ml) was added, while cooling with ice. The aluminium compounds thereby obtained were separated off by filtration and washed with THF (3×30 ml) and the filtrate was concentrated. After addition of water (30 ml), the amine was extracted with EA (3×40 ml) and the organic extracts were combined, washed with water (40 ml), dried and concentrated. The product was obtained as a beige-coloured, oily solid in a yield of 99% (4.36 g).

2-(4-Dimethylamino-4-phenylcyclohexylidene)-N-[6-(1H-indol-3-yl)hexyl]acetamide

1-Hydroxybenzotriazole (737 mg, 5.46 mmol), 6-(1H-indol-3-yl)hexylamine (590 mg, 2.73 mmol) and N-methylmorpholine (0.606 ml, 5.46 mmol) were added to a solution of
(4-dimethylamino-4-phenylcyclohexylidene)acetic acid hydrochloride (810 mg, 2.73 mmol) in dry dimethylformamide (10 ml) under argon. The solution was cooled to 0° C. and dicyclohexylcarbodiimide (1.13 g, 5.46 mmol) was added. The reaction mixture was stirred at RT for 11 d. Working up of the mixture was carried out by separating off the urea which had precipitated out and introducing the filtrate into a mixture of saturated NaCl solution (40 ml) and saturated NaHCO$_3$ solution (10 ml). Still further urea thereby precipitated out and was separated off. The aqueous phase was diluted with water (300 ml), 5 M sodium hydroxide solution (7 ml, 35 mmol) was added and the mixture was stored at 5° C. for 16 h. The crude product thereby precipitated out as a beige-coloured solid in a yield of 16% (197 mg). After chromatography on silica gel (20 g) with EA/methanol (4:1), the product was isolated as an oily compound (92 mg) in a yield of 8%.

2-(4-Dimethylamino-4-phenylcyclohexylidene)-N-[6-(1H-indol-3-yl)hexyl]acetamide hydrochloride (Example 18)

2-(4-Dimethylamino-4-phenylcyclohexylidene)-N-[6-(1H-indol-3-yl)hexyl]acetamide (78 mg, 0.17 mmol) was dissolved in ethyl methyl ketone (5 ml), and chlorotrimethylsilane (0.033 mol, 0.26 mmol) was added. After 1 h ether (10 ml) was added, and after 10 min the hydrochloride was isolated as a colourless solid with an m.p. of 160-164° C. in a yield of 87% (73 mg).

2-[4-Dimethylamino-4-(4-fluorophenyl)cyclohexylidene]-N-(3-phenylpropyl)acetamide 1-Hydroxybenzotriazole (864 mg, 6.4 mmol),
3-phenylpropylamine (0.455 ml, 3.2 mmol) and
N-methylmorpholine (0.703 ml, 6.4 mmol) were added to a solution of (4-dimethylamino-4-(4-fluorophenyl)cyclohexylidene)acetic acid hydrochloride (840 mg, 3.2 mmol) in dry dimethylformamide (25 ml) under argon. The solution was cooled to 0° C. and dicyclohexylcarbodiimide (1.32 g, 6.4 mmol) was added. The reaction mixture was stirred at RT for 4 d. Working up of the mixture was carried out by separating off the urea which had precipitated out and introducing the filtrate into a mixture of saturated NaCl solution (40 ml) and saturated NaHCO$_3$ solution (10 ml). Still further urea thereby precipitated out and was separated off. The filtrate was diluted with water (400 ml), 5 M sodium hydroxide solution (5 ml, 25 mmol) was added and the mixture was stored at 5° C. for 3 d. The product was thereby obtained as a beige-coloured oily solid in a yield of 45% (570 mg).

2-[4-Dimethylamino-4-(4-fluorophenyl)cyclohexylidene]-N-(3-phenylpropyl)acetamide hydrochloride (Example 19)

2-[4-Dimethylamino-4-(4-fluorophenyl)cyclohexylidene]-N-(3-phenylpropyl)acetamide (180 mg, 0.45 mmol)

was dissolved in ethyl methyl ketone (10 ml), and chlorotrimethylsilane (0.087 ml, 0.68 mmol) was added. After 1.5 h the hydrochloride was isolated as a colourless solid with an m.p. of 209-212° C. in a yield of 65% (126 mg).

2-[4-Dimethylamino-4-(4-fluorophenyl)cyclohexylidene]-N-[2-(1H-indol-3-yl)ethyl]acetamide 1-Hydroxybenzotriazole (864 mg, 6.4 mmol), tryptamine (512 mg, 3.2 mmol) and N-methylmorpholine (0.703 ml, 6.4 mmol) were added to a solution of (4-dimethylamino-4-(4-fluorophenyl)cyclohexylidene)acetic acid hydrochloride (840 mg, 3.2 mmol) in abs. dimethylformamide (25 ml) under argon. The solution was cooled to 0° C., dicyclohexylcarbodiimide (1.32 g, 6.4 mmol) was added and the mixture was stirred at RT for 4 d. Working up of the mixture was carried out by separating off the urea which had precipitated out and introducing the filtrate into a mixture of saturated NaCl solution (40 ml) and saturated NaHCO$_3$ solution (10 ml). Still further urea thereby precipitated out and was separated off. The filtrate was diluted with water (400 ml), 5 M sodium hydroxide solution (5 ml, 25 mmol) was added and the mixture was stored at 5° C. for 4 d. The product thereby precipitated out as a beige-coloured oily solid in a yield of 95% (1.27 mg).

2-[4-Dimethylamino-4-(4-fluorophenyl)cyclohexylidene]-N-[2-(1H-indol-3-yl)ethyl]acetamide hydrochloride (Example 20)

2-[4-Dimethylamino-4-(4-fluorophenyl)cyclohexylidene)-N-[2-(1H-indol-3-yl)ethyl]acetamide (871 mg, 2.08 mmol) was dissolved in ethyl methyl ketone (35 ml), and chlorotrimethylsilane (0.39 ml, 3.11 mmol) was added. After 1.5 h the hydrochloride was isolated as a beige-coloured solid with an m.p. of 217-221° C. in a yield of 85% (810 mg).

2-[4-Dimethylamino-4-(4-fluorophenyl)cyclohexylidene]-N-[2-(1H-indol-3-yl)-1-methylethyl]acetamide 1-Hydroxybenzotriazole (2.03 g, 15 mmol), DL-α-methyltryptamine (1.3 g, 7.5 mmol) and N-methylmorpholine (1.65 ml, 15 mmol) were added to a solution of (4-dimethylamino-4-(4-fluorophenyl)cyclohexylidene)acetic acid hydrochloride (1.98 g, 7.5 mmol) in abs. dimethylformamide (50 ml) under argon. The solution was cooled to 0° C., dicyclohexylcarbodiimide (3.09 g, 15 mmol) was added and the mixture was stirred at RT for 6 d. Working up of the mixture was carried out by separating off the urea which had precipitated out and introducing the filtrate into a mixture of saturated NaCl solution (40 ml) and saturated NaHCO$_3$ solution (10 ml). Still further urea thereby precipitated out and was separated off. The aqueous phase was diluted with water (300 ml), 5 M sodium hydroxide solution (7 ml, 35 mmol) was added and the mixture was stored at 5° C. for 16 h. The crude product thereby precipitated out as a yellow solid (1.55 g, 55%). After chromatography on silica gel (120 g) with EA/methanol (10:1), the less polar diastereoisomer was obtained in a yield of 19% (550 mg) and the more polar diastereoisomer was obtained in a yield of 9% (250 mg), as colourless solids.

2-[4-Dimethylamino-4-(4-fluorophenyl)cyclohexylidene]-N-[2-(1H-indol-3-yl)-1-methylethyl]acetamide hydrochloride (Examples 21 and 22)

The less polar diastereoisomer of 2-[4-dimethylamino-4-(4-fluorophenyl)cyclohexylidene]-N-[2-(1H-indol-3-yl)-1-methylethyl]acetamide (150 mg, 0.39 mmol) was dissolved in ethyl methyl ketone (10 ml), and chlorotrimethylsilane (0.075 ml, 0.59 mmol) was added. After 1.5 h it was possible to isolate the hydrochloride as a colourless solid in a yield of 63% (115 mg) with an m.p. of 188-191° C. (Example 21).

Chlorotrimethylsilane (0.12 ml, 0.98 mmol) was added to a solution of the more polar diastereoisomer of 2-[4-dimethylamino-4-(4-fluorophenyl)cyclohexylidene]-N-[2-(1H-indol-3-yl)-1-methylethyl]acetamide (250 mg, 0.65 mmol) in ethyl methyl ketone (10 ml) and the mixture was stirred at RT for 1.5 h. The hydrochloride (173 mg, 57%) thereby precipitated out as a colourless solid with an m.p. of 201-203° C. (Example 22).

2-(4-Dimethylamino-4-pyridin-2-ylcyclohexylidene)-N-[2-(1H-indol-3-yl)ethyl]acetamide 1-Hydroxybenzotriazole (546 mg, 4.0 mmol), tryptamine (320 mg, 2.0 mmol) and N-methylmorpholine (0.444 ml, 4.0 mmol) were added to a solution of (4-dimethylamino-1-hydroxy-4-pyridin-2-yl-cyclohexyl)acetic acid (556 mg, 2.0 mmol) in abs. dimethylformamide (30 ml) under argon. The solution was cooled to 0° C., dicyclohexylcarbodiimide (825 mg, 4.0 mmol) was added and the mixture was stirred at RT for 7 d. Working up of the mixture was carried out by separating off the urea which had precipitated out and introducing the filtrate into a mixture of saturated NaCl solution (40 ml) and saturated NaHCO$_3$ solution (10 ml). Still further urea thereby precipitated out and was separated off. The aqueous phase was diluted with water (400 ml), 5 M sodium hydroxide solution (7 ml, 35 mmol) was added and the mixture was stored at 5° C. for 16 h. The crude product thereby precipitated out as a beige-coloured solid (313 mg, 37%). After chromatography on silica gel (45 g) with EA/methanol (4:1), the product was obtained as a beige-coloured solid in a yield of 25% (210 mg).

2-(4-Dimethylamino-4-pyridin-2-ylcyclohexylidene)-N-[2-(1H-indol-3-yl)ethyl]acetamide hydrochloride (Example 23)

2-(4-Dimethylamino-4-pyridin-2-ylcyclohexylidene)-N-[2-(1H-indol-3-yl)ethyl]acetamide (210 mg, 0.52 mmol) was dissolved in ethyl methyl ketone (5 ml), and chlorotrimethylsilane (0.19 ml, 1.5 mmol) was added. After 1.5 h the hydrochloride was isolated as a beige-coloured solid with an m.p. of 147-150° C. in a yield of 89% (203 mg).

2-(4-Dimethylamino-4-pyridin-2-ylcyclohexylidene)-N-(3-phenylpropyl)acetamide 1-Hydroxybenzotriazole (546 mg, 4.0 mmol), 3-phenylpropylamine (270 mg, 2.0 mmol) and N-methylmorpholine (0.444 ml, 4.0 mmol) were added to a solution of (4-dimethylamino-1-hydroxy-4-pyridin-2-yl-cyclohexyl)acetic acid (556 mg, 2.0 mmol) in abs. dimethylformamide (30 ml) under argon. The solution was cooled to 0° C., dicyclohexylcarbodiimide (825 mg, 4.0 mmol) was added and the mixture was stirred at RT for 5 d. Working up of the mixture was carried out by separating off the urea which had precipitated out and introducing the filtrate into a mixture of saturated NaCl solution (40 ml) and saturated NaHCO$_3$ solution (10 ml). Still further urea thereby precipitated out and was separated off. The aqueous phase was diluted with water (300 ml), 5 M sodium hydroxide solution (7 ml, 35 mmol) was added and the mixture was stored at 5° C. for 16 h. The crude product thereby precipitated out as a beige-coloured oily compound (22.8 mg, 30%). After chromatography on silica gel (40 g) with EA/methanol (4:1), the amide was obtained as a beige-coloured oil in a yield of 27% (203 mg).

2-(4-Dimethylamino-4-pyridin-2-ylcyclohexy-lidene)-N-(3-phenylpropyl)acetamide hydrochloride (Example 24)

2-(4-Dimethylamino-4-pyridin-2-ylcyclohexylidene)-N-(3-phenylpropyl)acetamide (203 mg, 0.537 mmol was dissolved in ethyl methyl ketone (5 ml), and chlorotrimethylsilane (0.2 ml, 1.6 mmol) was added. After 1.5 h the hydrochloride was isolated as a colourless solid with an m.p. of 173-176° C. in a yield of 86% (190 mg).

2-(4-Dimethylamino-4-(3-fluorophenyl)cyclohexy-lidene]-N-[2-(1H-indol-3-yl)ethyl]acetamide 1-Hydroxybenzotriazole (1.08 g, 8.0 mmol), tryptamine (640 mg, 4.0 mmol) and N-methylmorpholine (0.888 ml, 8.0 mmol) were added to a solution of [4-dimethylamino-4-(3-fluoro-phenyl)-cyclohexylidene]acetic acid (1.55 g, 4.0 mmol) in dry dimethylformamide (15 ml) under argon. The solution was cooled to 0° C., dicyclohexylcarbodiimide (1.64 g, 8.0 mmol) was added and the mixture was stirred at RT for 4 d. Working up of the mixture was carried out by separating off the urea which had precipitated out and introducing the filtrate into a mixture of saturated NaCl solution (40 ml) and saturated $NaHCO_3$ solution (10 ml). Still further urea thereby precipitated out and was separated off. The aqueous phase was diluted with water (300 ml), 5 M sodium hydroxide solution (7 ml, 35 mmol) was added and the mixture was stored at 5° C. for 16 h. The crude product thereby precipitated out as a beige-coloured solid (1.3 g). After chromatography on silica gel (60 g) with EA/methanol (6:1), the product was obtained in a yield of 62% (1.03 g) with an m.p. of 172-176° C.

2-[4-Dimethylamino-4-(3-fluorophenyl)cyclohexy-lidene]-N-[2-(1H-indol-3-yl)ethyl]acetamide hydrochloride (Example 25)

2-[4-Dimethylamino-4-(3-fluorophenyl)cyclohexylidene]-N-[2-(1H-indol-3-yl)ethyl]acetamide (350 mg, 0.82 mmol) was dissolved in ethyl methyl ketone (25 ml), and chlorotrimethylsilane (0.164 ml, 1.3 mmol) was added. After 1.5 h it was possible to isolate the hydrochloride as a colourless solid in a yield of 89% (336 mg) with an m.p. of 196-200° C.

2-[4-Dimethylamino-4-(3-fluorophenyl)cyclohexy-lidene]-N-[2-(1H-indol-3-yl)-1-methylethyl]aceta-mide 1-Hydroxybenzotriazole (1.43 g, 10.6 mmol), DL-α-methyltryptamine (923.3 mg, 5.3 mmol), N-methylmorpholine (1.07 g, 10.6 mmol) and dicyclohexylcarbodiimide (2.19 g, 10.6 mmol) were added to a solution of [4-dimethylamino-4-(3-fluoro-phenyl)-cyclohexylidene]acetic acid (1.4 g, 5.3 mmol) in dry dimethylformamide (50 ml) under argon and the mixture was stirred at RT for 6 d. Working up of the mixture was carried out by separating off the urea which had precipitated out and introducing the filtrate into a mixture of saturated NaCl solution (40 ml) and saturated $NaHCO_3$ solution (10 ml). Still further urea thereby precipitated out and was separated off. The aqueous phase was diluted with water (300 ml), 5 M sodium hydroxide solution (7 ml, 35 mmol) was added and the mixture was stored at 5° C. for 20 h. The crude product thereby precipitated out as a yellow solid (1.2 g). The product was a mixture of the two diastereoisomer amides, which were separated by chromatography on silica gel G [100 g; EtOAc/MeOH (10:1)]. The less polar diastereoisomer was obtained in a yield of 410.6 mg (18%) with an m.p. of 163-166° C. and the more polar diastereoisomer was obtained in a yield of 249.3 mg (11%), as a colourless oil.

2-[4-Dimethylamino-4-(3-fluorophenyl)cyclohexy-lidene]-N-[2-(1H-indol-3-yl)-1-methylethyl]aceta-mide hydrochloride (Examples 26 and 27)

The less polar diastereoisomer of 2-[4-dimethylamino-4-(3-fluorophenyl)cyclohexylidene]-N-[2-(1H-indol-3-yl)-1-methylethyl]acetamide (150 mg, 0.35 mmol) was dissolved in ethyl methyl ketone (5 ml), and trimethylchlorosilane (0.066 ml, 0.52 mmol) was added. After stirring at RT for 2 h, the hydrochloride was filtered off with suction and isolated as a colourless solid with an m.p. of 165-188° C. in a yield of 77% (126.6 mg) (Example 26).

Trimethylchlorosilane (0.109 ml, 0.86 mmol) was added to a solution of the more polar diastereoisomer of 2-[4-dimethylamino-4-(3-fluorophenyl)cyclohexylidene]-N-[2-(1H-indol-3-yl)-1-methylethyl]acetamide (249 mg, 0.57 mmol) in ethyl methyl ketone (10 ml) and the mixture was stirred at RT for 1.5 h. The hydrochloride which had precipitated out was filtered off with suction and isolated as a colourless solid with an m.p. of 171-174° C. in a yield of 81% (218 mg) (Example 27).

2-[4-Dimethylamino-4-(3-fluorophenyl)cyclohexy-lidene]-N-(3-phenylpropyl)acetamide 1-Hydroxybenzotriazole (1.53 g, 11.36 mmol), 3-phenylpropylamine (768 mg, 5.68 mmol), N-methylmorpholine (1.15 g, 11.36 mmol) and dicyclohexylcarbodiimide (2.34 g, 11.36 mmol) were added to a solution of [4-dimethylamino-4-(3-fluoro-phenyl)-cyclohexylidene]acetic acid (1.5 g, 5.68 mmol) in dry dimethylformamide (35 ml) under argon and the mixture was stirred at RT for 3 d. The urea which had precipitated out was separated off and the filtrate was introduced into a mixture of saturated NaCl solution (40 ml) and saturated $NaHCO_3$ solution (10 ml). Still further urea thereby precipitated out and was separated off. The aqueous phase was diluted with water (300 ml), 5 M sodium hydroxide solution (7 ml, 35 mmol) was added and the mixture was stored at 5° C. for 20 h. The crude product thereby precipitated out as a beige-coloured solid (2.16 g). After chromatography on silica gel G [100 g; EtOAc/MeOH (10:1)], the amide was obtained in a yield of 29% (648.5 mg) with an m.p. of 129-131° C.

2-[4-Dimethylamino-4-(3-fluorophenyl)cyclohexy-lidene]-N-(3-phenylpropyl)acetamide hydrochloride (Example 28)

2-[4-Dimethylamino-4-(3-fluorophenyl)cyclohexylidene]-N-(3-phenylpropyl)acetamide (150 mg, 0.35 mmol) was dissolved in ethyl methyl ketone (10 ml) with gentle heating and trimethylchlorosilane (0.082 ml, 0.65 mmol) was added. After stirring at RT for 2 h, the reaction mixture was concentrated to dryness. The residue was stirred briefly with ether (10 ml) and the hydrochloride was isolated as a colourless solid with an m.p. of 230-233° C. in a yield of 98% (184 mg).

2-(4-Dimethylamino-4-phenylcyclohexyl)-N-(2-trifluoro-methylbenzyl)acetamide hydrochloride (Example 29)

Palladium-on-charcoal (5%, 12 mg) was added to a solution of 2-(4-dimethylamino-4-phenylcyclohexylidene)-N-(2-trifluoromethyl-benzyl)acetamide hydrochloride (Example 13; 236 mg, 0.52 mmol) in methanol. The reaction mixture was hydrogenated at RT under a pressure of 2 bar for 4 h. The catalyst was separated off over Celite and the filtrate was concentrated. The product was thereby isolated as a colourless, hygroscopic solid in a yield of 58% (138 mg).

(4-Dimethylamino-4-phenylcyclohexyl)acetic acid methyl ester hydrochloride

Palladium-on-charcoal (5%, 90 mg) was added to a solution of (4-dimethylamino-4-phenylcyclohexylidene)acetic acid methyl ester hydrochloride (1.79 g, 5.77 mmol) in methanol. The reaction mixture was hydrogenated at RT under a pressure of 3 bar for 5 h. The catalyst was separated off over Celite and the filtrate was concentrated. The product was thereby isolated as a colourless, oily compound in a quantitative yield (1.79 g).

(4-Dimethylamino-4-phenylcyclohexyl)acetic acid hydrochloride 1.7 M KOH (70.5 ml, 120 mmol) was added to a solution of (4-dimethylamino-4-phenylcyclohexyl)acetic acid methyl ester hydrochloride (1.79 g, 5.77 mmol) in ethanol (80 ml). The mixture was stirred at RT for 16 h. The reaction mixture was concentrated and the residue was taken up in water. The aqueous phase was extracted with ether, and 5.5 M hydrochloric acid (23.6 ml, 130 mmol) was added. After concentration of the aqueous phase, the residue was extracted with ethanol, the potassium chloride which remained was separated off and the filtrate was concentrated. The product was thereby obtained as a colourless, oily compound in a yield of 95% (1.62 g).

2-(4-Dimethylamino-4-phenylcyclohexyl)-N-[2-(1H-indol-3-yl)ethyl]acetamide

1-Hydroxybenzotriazole (273 mg, 2.0 mmol), tryptamine hydrochloride (196 mg, 1.0 mmol) and N-methylmorpholine (0.333 ml, 3.0 mmol) were added to a solution of
(4-dimethylamino-4-phenylcyclohexyl)acetic acid hydrochloride (298 mg, 1.0 mmol) in dry dimethylformamide under argon. The clear solution was cooled in an ice-bath and dicyclohexylcarbodiimide (417 mg, 2.0 mmol) was added. The reaction mixture was stirred at RT for 3 d and worked up by separating off the urea which had precipitated out and introducing the filtrate into a mixture of saturated NaCl solution (40 ml) and saturated NaHCO$_3$ solution (10 ml). The mixture was diluted with water, 5 M sodium hydroxide solution (4 ml, 20 mmol) was added and the mixture was stored at 5° C. for 16 h. The crude product thereby precipitated out as a beige-coloured substance (400 mg). After purification by chromatography on silica gel with methanol, the product was obtained as a beige-coloured solid in a yield of 35% (144 mg) and with an m.p.
of 194-197° C.

2-(4-Dimethylamino-4-phenylcyclohexyl)-N-[2-(1H-indol-3-yl)ethyl]acetamide hydrochloride (Example 30)

2-(4-Dimethylamino-4-phenylcyclohexyl)-N-[2-(1H-indol-3-yl)ethyl]acetamide (141 mg, 0.35 mmol) was warmed gently in ethyl methyl ketone, and chlorotrimethylsilane (0.066 ml, 0.52 mmol) was added. After 1.5 h it was possible to filter off a beige-coloured, hygroscopic product with suction. The filtrate was reduced to a volume of 5 ml and ether was added. The hydrochloride thereby precipitated out as a colourless solid in a yield of 47% (72 mg). M.p.: 135-140° C.

2-(4-Dimethylamino-4-phenylcyclohexyl)-N-(3-phenylpropyl)-acetamide

1-Hydroxybenzotriazole (273 mg, 2.0 mmol), 3-phenylpropylamine (0.142 ml, 1.0 mmol) and N-methylmorpholine (0.222 ml, 2.0 mmol) were added to a solution of (4-dimethylamino-4-phenylcyclohexyl)acetic acid hydrochloride (298 mg, 1.0 mmol) in dry dimethylformamide under argon. Dicyclohexylcarbodiimide (417 mg, 2.0 mmol) was added to the clear solution at 0° C. The reaction mixture was stirred at RT for 3 d, the urea which had precipitated out was filtered off with suction and the filtrate was introduced into a mixture of saturated NaCl solution (40 ml) and saturated NaHCO$_3$ solution (10 ml). 5 M sodium hydroxide solution (12 ml, 60 mmol) was added to the aqueous phase and the mixture was diluted with water (300 ml) and stored at 5° C. for 3 d. The product was thereby produced as a colourless compound and was to be obtained in a yield of 58% (220 mg) by filtration, taking up of the residue in ethanol and concentration.

2-(4-Dimethylamino-4-phenylcyclohexyl)-N-(3-phenylpropyl)-acetamide) hydrochloride (Example 31)

2-(4-Dimethylamino-4-phenylcyclohexyl)-N-(3-phenylpropyl)acetamide) (209 mg, 0.55 mmol) was dissolved in ethyl methyl ketone (5 ml), and chlorotrimethylsilane (0.104 ml, 1.0 mmol) was added. After 1.5 h the hydrochloride was isolated as a colourless solid with an m.p. of 212-215° C. and in a yield of 68% (153 mg).

2-(4-Dimethylamino-4-phenylcyclohexyl)-N-phenethylacetamide

1-Hydroxybenzotriazole (273 mg, 2.0 mmol), 2-phenylethylamine (0.125 ml, 1.0 mmol) and N-methylmorpholine (0.222 ml, 2.0 mmol) were added to a solution of (4-dimethylamino-4-phenylcyclohexyl)acetic acid hydrochloride (298 mg, 1.0 mmol) in dry dimethylformamide under argon. Dicyclohexylcarbodiimide (417 mg, 2.0 mmol) was added at 0° C. and the mixture was stirred at RT for 5 d. The urea which had precipitated out was filtered off with suction and the filtrate was introduced into a mixture of saturated NaCl solution (40 ml) and saturated NaHCO$_3$ solution (10 ml). Still further urea thereby precipitated out as a mixture with the product (349 mg) and was separated off. The filtrate obtained was diluted with water (300 ml), 5 M sodium hydroxide solution (8 ml, 40 mmol) was added and the mixture was stored at 5° C. for 16 h. Further product thereby precipitated out as a colourless solid (172 mg). After purification of the fraction contaminated with dicyclohexylurea by chromatography on silica gel with methanol, further product (49 mg) was obtained. The product was isolated in a total yield of 61% (221 mg) with an m.p. of 182-186° C.

2-(4-Dimethylamino-4-phenylcyclohexyl)-N-phenethylacetamide hydrochloride (Example 32)

2-(4-Dimethylamino-4-phenylcyclohexyl)-N-phenethylacetamide (220 mg, 0.6 mmol) was dissolved in ethyl methyl ketone with gentle heating and chlorotrimethylsilane (0.113 ml, 0.9 mmol) was added. After 1.5 h it was possible to isolate a colourless, hygroscopic solid in a yield of 80% (191 mg).

2-(4-Dimethylamino-4-phenylcyclohexyl)-N-(4-phenylbutyl)acetamide

1-Hydroxybenzotriazole (273 mg, 2.0 mmol), 4-phenylbutylamine (0.158 ml, 1.0 mmol) and N-methylmorpholine (0.222 ml, 2.0 mmol) were added to a solution of (4-dimethylamino-4-phenylcyclohexyl)acetic acid hydrochloride (298 mg, 1.0 mmol) in dry dimethylformamide under argon. Dicyclohexylcarbodiimide (417 mg, 2.0 mmol) was added at 0° C. and the mixture was stirred at RT for 5 d. Working up of the mixture was carried out by separating off the urea which had precipitated out and introducing the filtrate into a mixture of saturated NaCl solution (40 ml) and saturated NaHCO$_3$ solution (10 ml). The filtrate was diluted with water (300 ml), 5 M sodium hydroxide solution (8 ml, 40 mmol) was added and the mixture was stored at 5° C. for 16 h. The crude product thereby precipitated out as a beige-coloured substance, which was separated off by filtration (222 mg). The product was taken up in ethyl methyl ketone (7 ml) and separated from an insoluble residue by filtration. The filtrate was concentrated and the pure product was obtained in a yield of 194 mg (49%).

2-(4-Dimethylamino-4-phenylcyclohexyl)-N-(4-phenylbutyl)-acetamide hydrochloride (Example 33)

2-(4-Dimethylamino-4-phenylcyclohexyl)-N-(4-phenylbutyl)acetamide (194 mg, 0.49 mmol) was dissolved in ethyl methyl ketone, and chlorotrimethylsilane (0.093 ml, 0.74 mmol) was added. After 1.5 h it was possible to filter off the product with suction as a colourless, hygroscopic solid in a yield of 30% (63 mg).

(2S)-2-[2-(4-Dimethylamino-4-phenylcyclohexyl) acetylamino]-3-(1H-indol-3-yl)propanoic acid methyl ester 1-Hydroxybenzotriazole (546 mg, 4.0 mmol), L-tryptophan methyl ester hydrochloride (509 mg, 2.0 mmol) and N-methylmorpholine (0.666 ml, 6.0 mmol) were added to a solution of (4-dimethylamino-4-phenylcyclohexyl)acetic acid hydrochloride (596 mg, 2.0 mmol) in dry dimethylformamide under argon. Dicyclohexylcarbodiimide (834 mg, 4.0 mmol) was added at 0° C. and the mixture was stirred at RT for 4 d. Working up of the mixture was carried out by separating off the solid which had precipitated out (1.1 g), which comprised a mixture of dicyclohexylurea and the hydrochloride of the amide. The filtrate was added to a mixture of saturated NaCl solution (40 ml) and saturated NaHCO$_3$ solution (10 ml). The filtrate of the mixture was extracted by shaking with methylene chloride (3×50 ml) and, after drying, the organic phase was concentrated. An oily crude product was thereby obtained (660 mg), from which it was possible to obtain the product (188 mg) after purification by chromatography on silica gel with EA/methanol (4:1). The substance mixture which had precipitated out at the start of the working up was taken up in methylene chloride and saturated sodium bicarbonate solution. The aqueous phase was extracted with methylene chloride. The organic phase was concentrated (517 mg) and separated by chromatography with EA/methanol (4:1), it being possible for a further fraction of the amide (357 mg) to be isolated. The total yield of the product was 59% (545 mg).

(2S)-2-[2-(4-Dimethylamino-4-phenylcyclohexyl) acetylamino]-3-(1H-indol-3-yl)propanoic acid methyl ester hydrochloride (Example 34)

(2S)-2-[2-(4-Dimethylamino-4-phenylcyclohexyl)acetylamino]-3-(1H-indol-3-yl)propanoic acid methyl ester (271 mg, 0.587 mmol) was dissolved in ethyl methyl ketone, and chlorotrimethylsilane (0.111 ml, 0.88 mmol) was added. After 1 h ether (30 ml) was added to the mixture and the mixture was stirred for a further 10 min. The hydrochloride was filtered off and obtained as a colourless solid in a yield of 96% (278 mg) with an m.p. of 239-241° C.

(2S)-2-[2-(4-Dimethylamino-4-phenylcyclohexyl) acetylamino]-3-(1H-indol-3-yl)propanoic acid methyl ester potassium salt (Example 35)

(2S)-2-[2-(4-Dimethylamino-4-phenylcyclohexyl)acetylamino]-3-(1H-indol-3-yl)propanoic acid methyl ester (249 mg, 0.54 mmol) was dissolved in ethanol, and 1.7 M KOH (6.3 ml, 10.8 mmol) was added. After a reaction time of 16 h at RT, working up of the mixture was carried out by concentration, addition of EA and stirring at RT for 2 h. The potassium salt thereby precipitated out as a colourless solid and was isolated in a yield of 80% (207 mg) with an m.p. of 184-186° C.

2-(4-Dimethylamino-4-phenylcyclohexyl)-N-(1H-indol-3-ylmethyl)acetamide

1-Hydroxybenzotriazole (546 mg, 4.0 mmol), C-(1H-indol-3-yl)methylamine (292 mg, 2.0 mmol) and N-methylmorpholine (0.444 ml, 4.0 mmol) were added to a solution of (4-dimethylamino-4-phenylcyclohexyl)acetic acid hydrochloride (596 mg, 2.0 mmol) in dry dimethylformamide under argon. Dicyclohexylcarbodiimide (834 mg, 4.0 mmol) was added at 0° C. and the mixture was stirred at RT for 7 d. Working up of the mixture was carried out by separating off the urea which had precipitated out and introducing the filtrate into a mixture of saturated NaCl solution (40 ml) and saturated NaHCO$_3$ solution (10 ml). A mixture of urea and product thereby precipitated out (482 mg) and was separated off. The filtrate obtained was diluted with water (300 ml), 5 M sodium hydroxide solution (4 ml, 20 mmol) was added and the mixture was stored at 5° C. for 16 h. A crude product thereby precipitated out as a beige-coloured substance (234 mg), which was separated off by filtration. After purification of the two product fractions by chromatography on silica gel with EA/methanol (4:1) and methanol, the product was isolated as a beige-coloured solid in a yield of 30% (230 mg).

2-(4-Dimethylamino-4-phenylcyclohexyl)-N-(1H-indol-3-ylmethyl)acetamide hydrochloride (Example 36)

2-(4-Dimethylamino-4-phenylcyclohexyl)-N-(1H-indol-3-ylmethyl)acetamide (213 mg, 0.54 mmol) was dissolved in ethyl methyl ketone with gentle heating and chlorotrimethylsilane (0.103 ml, 0.82 mmol) was added. After 1.5 h it was possible to obtain the hydrochloride as a colourless solid in a yield of 93% (214 mg) with an m.p. of 233-235° C.

2-(4-Dimethylamino-4-phenylcyclohexyl)-N-[4-(1H-indol-3-yl)butyl]acetamide

Palladium-on-charcoal (5%, 10 mg) was added to a solution of (O)-2-(4-dimethylamino-4-phenylcyclohexylidene)-

N-[4-(1H-indol-3-yl)butyl]-acetamide (196 mg, 0.456 mmol) in methanol. The reaction mixture was hydrogenated at RT under a pressure of 2 bar for 21 h. The catalyst was separated off over Celite and the filtrate was concentrated. A colourless solid (186 mg) was thereby isolated. The crude product was purified by chromatography on silica gel with methanol. 2-(4-Dimethylamino-4-phenylcyclohexyl)-N-[4-(1H-indol-3-yl)butyl]acetamide was isolated as a colourless product with an m.p. of 186° C. in a yield of 30% (58 mg).

2-(4-Dimethylamino-4-phenylcyclohexyl)-N-[4-(1H-indol-3-yl)butyl]acetamide hydrochloride (Example 37)

2-(4-Dimethylamino-4-phenylcyclohexyl)-N-[4-(1H-indol-3-yl)butyl]acetamide (58 mg, 0.142 mmol) was dissolved in ethyl methyl ketone with gentle heating and chlorotrimethylsilane (0.027 ml, 0.213 mmol) was added. After 1.5 h it was possible to obtain the hydrochloride as a colourless solid in a yield of 65% (43 mg) with an m.p. of 165-174° C.

2-(4-Dimethylamino-4-phenylcyclohexyl)-N-[3-(1H-indol-3-yl)propyl]-acetamide

Palladium-on-charcoal (5%, 20 mg) was added to a solution of 2-(4-dimethylamino-4-phenyl-cyclohexylidene)-N-[3-(1H-indol-3-yl)propyl]-acetamide (base of Example 16; 305 mg, 0.734 mmol) in abs. methanol (30 ml). The reaction mixture was hydrogenated at RT under a pressure of 3 bar for 6 h. The catalyst was separated off over Celite and the filtrate was concentrated. After separation of the residue (289 mg) by chromatography on silica gel (20 g) with EA/methanol (2:1), the product was isolated as a beige-coloured oil in a yield of 29% (95 mg).

2-(4-Dimethylamino-4-phenylcyclohexyl)-N-[3-(1H-indol-3-yl)propyl]-acetamide hydrochloride (Example 38)

2-(4-Dimethylamino-4-phenylcyclohexyl)-N-[3-(1H-indol-3-yl)propyl]-acetamide (68 mg, 0.162 mmol) was dissolved in ethyl methyl ketone (5 ml), and chlorotrimethylsilane (0.033 ml, 0.245 mmol) was added. After 3 h it was possible to isolate the product as a colourless solid in a yield of 65% (54 mg) with an m.p. of 162-170° C.

2-(4-Dimethylamino-4-phenylcyclohexyl)-N-[5-(1H-indol-3-yl)pentyl]-acetamide

Palladium-on-charcoal (5%, 15 mg) was added to a solution of 2-(4-dimethylamino-4-phenylcyclohexylidene)-N-[5-(1H-indol-3-yl)pentyl]acetamide (base of Example 17; 246 mg, 0.55 mmol) in abs. methanol (30 ml). The reaction mixture was hydrogenated at RT under a pressure of 2 bar for 6 h. The catalyst was separated off over Celite and the filtrate was concentrated. After separation of the residue (234 mg) by chromatography on silica gel (30 g) with EA/methanol (1:1), the product was isolated as a beige-coloured oil in a yield of 46% (112 mg).

2-(4-Dimethylamino-4-phenylcyclohexyl)-N-[5-(1H-indol-3-yl)pentyl]-acetamide hydrochloride (Example 39)

2-(4-Dimethylamino-4-phenylcyclohexyl)-N-[5-(1H-indol-3-yl)pentyl]-acetamide (112 mg, 0.25 mmol) was dissolved in ethyl methyl ketone (5 ml), and chlorotrimethylsilane (0.048 ml, 0.38 mmol) was added. After 1 h ether (15 ml) was added to the reaction mixture. The product was obtained as a pink-coloured solid in a yield of 90% (108 mg).

2-(4-Dimethylamino-4-phenylcyclohexyl)-N-[6-(1H-indol-3-yl)hexyl]acetamide

1-Hydroxybenzotriazole (540 mg, 4.0 mmol), 6-(1H-indol-3-yl)hexylamine (432 mg, 2.0 mmol) and N-methylmorpholine (0.444 ml, 4.0 mmol) were added to a solution of 4-dimethylamino-4-phenylcyclohexyl-acetic acid hydrochloride (595 mg, 2.0 mmol) in dry dimethylformamide (10 ml) under argon. The clear solution was cooled in an ice-bath, dicyclohexylcarbodiimide (825 mg, 4.0 mmol) was added and the mixture was stirred at RT for 5 d, during which dicyclohexylurea precipitated out. Working up of the mixture was carried out by separating off the urea which had precipitated out and introducing the filtrate into a mixture of saturated NaCl solution (40 ml) and saturated NaHCO$_3$ solution (10 ml). Still further urea thereby precipitated out and was separated off. After 10 min the crude product precipitated out of the filtrate and was filtered off. The aqueous phase was diluted with water (300 ml), 5 M sodium hydroxide solution (7 ml, 35 mmol) was added and the mixture was stored at 5° C. for 3 d. Further product thereby precipitated out as a beige-coloured solid in a yield of 9% (82 mg) with an m.p. of 152-156° C. The crude product was purified by chromatography on silica gel (40 g) with EA/methanol (4:1) and (1:1). The product was thereby isolated as a beige-coloured compound (534 mg) in a yield of 58%.

2-(4-Dimethylamino-4-phenylcyclohexyl)-N-[6-(1H-indol-3-yl)hexyl]acetamide hydrochloride (Example 40)

2-(4-Dimethylamino-4-phenylcyclohexyl)-N-[6-(1H-indol-3-yl)hexyl]acetamide (516 mg, 1.12 mmol) was dissolved in a mixture of ethyl methyl ketone (25 ml) and ethanol (5 ml), and 5 M isopropanolic hydrochloric acid (0.44 ml, 2.2 mmol) was added. After 3 h the reaction mixture was concentrated, ether (15 ml) was added and the mixture was concentrated again. The residue was digested with ether (30 ml). After filtration, the product was obtained as a beige-coloured solid in a yield of 62% (342 mg).

2-(4-Dimethylamino-4-phenylcyclohexyl)-N-[2-(1H-indol-3-yl)-1-methylethyl]acetamide 1-Hydroxybenzotriazole (675 mg, 5.0 mmol), α-methyltryptamine (435 mg, 2.5 mmol) and N-methylmorpholine (0.555 ml, 5.0 mmol) were added to a solution of 4-dimethylamino-4-phenylcyclohexyl-acetic acid hydrochloride (744 mg, 2.5 mmol) in dry dimethylformamide (10 ml) under argon. The clear solution was cooled in an ice-bath, dicyclohexylcarbodiimide (1.03 g, 5.0 mmol) was added and the mixture was stirred at RT for 5 d, during which dicyclohexylurea precipitated out. Working up of the mixture was carried out by separating off the urea which had precipitated out and introducing the filtrate into a mixture of saturated NaCl solution (40 ml) and saturated NaHCO$_3$ solution (10 ml). Still further urea thereby precipitated out and was separated off. The aqueous phase was diluted with water (300 ml), 5 M sodium hydroxide solution (7 ml, 35 mmol) was added and the mixture was stored at 5° C. for 16 h. The product thereby precipitated out as a mixture with dicyclohexylurea as a beige-coloured solid in a yield of 93% (968 mg).

2-(4-Dimethylamino-4-phenylcyclohexyl)-N-[2-(1H-indol-3-yl)-1-methylethyl]acetamide hydrochloride (Example 41)

Ethyl methyl ketone (55 ml) was added to a mixture of 2-(4-dimethylamino-4-phenylcyclohexyl)-N-[2-(1H-indol-3-yl)-1-methylethyl]acetamide with dicyclohexylurea (939 mg) and the mixture was heated to 40° C. and filtered. The acetamide thereby remained as a colourless solid (327 mg, 0.78 mmol) with an m.p. of 198-200° C. It was dissolved in ethanol (20 ml), and 5 M propanolic hydrochloric acid (0.22 ml, 1.11 mmol) was added. After 2 h the reaction mixture was concentrated to 2 ml, ether (50 ml) was added and the mixture was stirred at RT for 1 h. It was possible to isolate the product as a colourless solid with an m.p. of 150-155° C. in a yield of 33% (338 mg).

2-[4-Dimethylamino-4-(4-fluorophenyl)cyclohexyl]-N-(3-phenylpropyl)acetamide

Palladium-on-charcoal (5%, 24 mg) was added to a solution of 2-[4-dimethylamino-4-(4-fluorophenyl)-cyclohexylidene]-N-(3-phenylpropyl)-acetamide (base of Example 19; 390 mg, 0.99 mmol) in abs. methanol (25 ml). The reaction mixture was hydrogenated at RT under a pressure of 2 bar for 17 h. The catalyst was separated off over Celite and the filtrate was concentrated. After separation of the residue (402 mg) by chromatography on silica gel (80 g) with EA/methanol (2:1), the less polar diastereoisomer of 2-[4-dimethylamino-4-(4-fluorophenyl)cyclohexyl]-N-(3-phenylpropyl)acetamide was isolated as a beige-coloured oil in a yield of 24% (78 mg) and the more polar diastereoisomer of 2-[4-dimethylamino-4-(4-fluorophenyl)cyclohexyl]-N-(3-phenylpropyl)acetamide was isolated as a colourless oily solid in a yield of 76% (297 mg).

2-[4-Dimethylamino-4-(4-fluorophenyl)cyclohexyl]-N-(3-phenylpropyl)acetamide hydrochloride (Examples 42 and 43)

The less polar diastereoisomer of 2-[4-dimethylamino-4-(4-fluorophenyl)cyclohexyl]-N-(3-phenylpropyl)acetamide (78 mg, 0.2 mmol) was dissolved in ethyl methyl ketone (10 ml), and chlorotrimethylsilane (0.038 ml, 0.3 mmol) was added. After 1.5 h ether (15 ml) was added and the mixture was stirred for 30 min. The product (Example 42) was obtained as a colourless solid in a yield of 71% (62 mg) with an m.p. of 109-111° C.

The more polar diastereoisomer of 2-[4-dimethylamino-4-(4-fluorophenyl)cyclohexyl]-N-(3-phenylpropyl)acetamide (295 mg, 0.74 mmol) was dissolved in a mixture of ethyl methyl ketone (10 ml) and ethanol (10 ml), 5 M propanolic hydrochloric acid (0.22 ml, 1.1 mmol) was added and the mixture was stirred at RT for 1.5 h. After addition of ether (50 ml), the mixture was stirred for 2 h and the hydrochloride which had precipitated out was separated off. The product was obtained in a yield of 67% (213 mg) (Example 43).

2-[4-Dimethylamino-4-(4-fluorophenyl)cyclohexyl]-N-[2-(1H-indol-3-yl)ethyl]acetamide Palladium-on-charcoal (5%, 40 mg) was added to a solution of 2-[4-dimethylamino-4-(4-fluorophenyl)-cyclohexylidene]-N-[2-(1H-indol-3-yl)ethyl]-acetamide (base of Example 20; 442 mg, 1.05 mmol) in abs. methanol (80 ml). The reaction mixture was hydrogenated at RT under a pressure of 2 bar for 17 h. The catalyst was separated off over Celite and the filtrate was concentrated. After separation of the residue by chromatography on silica gel (80 g) with EA/methanol (2:1), the less polar diastereoisomer of 2-[4-dimethylamino-4-(4-fluorophenyl)cyclohexyl]-N-[2-(1H-indol-3-yl)ethyl]acetamide was isolated as a colourless oil (90 mg) as a mixture with a second non-identifiable product and the pure more polar diastereoisomer of 2-[4-dimethylamino-4-(4-fluorophenyl)cyclohexyl]-N-[2-(1H-indol-3-yl)ethyl]acetamide was isolated as a colourless solid with an m.p. of 210-213° C. in a yield of 50%.

2-[4-Dimethylamino-4-(4-fluorophenyl)cyclohexyl]-N-[2-(1H-indol-3-yl)ethyl]acetamide hydrochloride (Example 44)

The more polar diastereoisomer of 2-[4-dimethylamino-4-(4-fluorophenyl)cyclohexyl]-N-[2-(1H-indol-3-yl)ethyl]acetamide (224 mg, 0.74 mmol) was dissolved in a mixture of ethyl methyl ketone (15 ml) and ethanol (15 ml), 5 M isopropanolic hydrochloric acid (0.16 ml, 0.795 mmol) was added and the mixture was stirred at RT for 2.5 h. The product was filtered off with suction and obtained in a yield of 75% (181 mg) with an m.p. of 252-255° C.

2-[4-(Dimethylamino-4-(4-fluorophenyl)cyclohexyl]-N-[2-(1H-indol-3-yl)-1-methylethyl]acetamide Palladium-on-charcoal (5%, 40 mg) was added to a solution of 2-[4-(dimethylamino-4-(4-fluoro-phenyl)-cyclohexylidene]-N-[2-(1H-indol-3-yl)-1-methyl-ethyl]-acetamide (370 mg, 0.97 mmol) in abs. methanol (40 ml). The reaction mixture was hydrogenated at RT under a pressure of 3 bar for 23 h. The catalyst was separated off over Celite and the filtrate was concentrated. After separation of the residue (339 mg) by chromatography on silica gel (50 mg) with EA/methanol (2:1), the less polar diastereoisomer of 2-[4-(dimethylamino-4-(4-fluorophenyl)cyclohexyl]-N-[2-(1H-indol-3-yl)-1-methylethyl]acetamide was isolated as a colourless oil in a yield of 11% (45 mg) and the more polar diastereoisomer of 2-[4-(dimethylamino-4-(4-fluorophenyl)cyclohexyl]-N-[2-(1H-indol-3-yl)-1-methylethyl]acetamide was isolated as a colourless solid with an m.p. of 220-222° C. in a yield of 57% (240 mg).

2-[4-Dimethylamino-4-(4-fluorophenyl)cyclohexyl]-N-[2-(1H-indol-3-yl)-1-methylethyl]acetamide hydrochloride (Examples 45 and 46)

The less polar diastereoisomer of 2-[4-(dimethylamino-4-(4-fluorophenyl)cyclohexyl]-N-[2-(1H-indol-3-yl)-1-methylethyl]acetamide (44 mg, 0.1 mmol) was dissolved in ethyl methyl ketone (5 ml), and chlorotrimethylsilane (0.019 ml, 0.15 mmol) was added. After 1.5 h ether (5 ml) was added and the mixture was stirred for 30 min. The product was obtained as a colourless oily compound in a yield of 38% (18 mg) (Example 45).

The more polar diastereoisomer of 2-[4-(dimethylamino-4-(4-fluorophenyl)cyclohexyl]-N-[2-(1H-indol-3-yl)-1-methylethyl]acetamide (223 mg, 0.5 mmol) was dissolved in ethanol (20 ml), 5 M isopropanolic hydrochloric acid (0.154 ml, 0.75 mmol) was added and the mixture was stirred at RT for 1 h. The reaction mixture was concentrated and the residue was stirred with ether (10 ml) for 16 h. The colourless hydrochloride which had precipitated out was separated off and obtained in a yield of 88% (207 mg) with an m.p. of 188-191° C. (Example 46).

2-(4-Dimethylamino-4-pyridin-2-ylcyclohexyl)-N-[2-(1H-indol-3-yl)-ethyl]acetamide 1-Hydroxybenzotriazole (546 mg, 4.0 mmol), tryptamine (320 mg, 2.0 mmol) and N-methylmorpholine (0.444 ml, 4.0 mmol) were added to a solution of the less polar diastereoisomer of (4-dimethylamino-4-pyridin-2-yl-cyclohexyl)-acetic acid (598 mg, 2.0 mmol) in abs. dimethylformamide (20 ml) under argon. The solution was cooled in an ice-bath, dicyclohexylcarbodiimide (825 mg, 4.0 mmol) was added and the mixture was stirred at RT for 6 d, during which dicyclohexylurea precipitated out. Working up of the mixture was carried out by separating off the urea which had precipitated out and introducing the filtrate into a mixture of saturated NaCl solution (40 ml) and saturated NaHCO₃ solution (10 ml). Still further urea thereby precipitated out and was separated off. The aqueous phase was diluted with water (300 ml), 5 M sodium hydroxide solution (7 ml, 35 mmol) was added and the mixture was stored at 5° C. for 16 h. The crude product was thereby obtained as a beige-coloured oily compound (303 mg, 37%). After purification by chromatography on silica gel (45 g) with EA/methanol (2:1) the product was obtained as a beige-coloured oil in a yield of 17% (141 mg).

1-Hydroxybenzotriazole (432 mg, 3.2 mmol), tryptamine (256 mg, 1.6 mmol) and N-methylmorpholine (0.352 ml, 3.2 mmol) were added to a solution of the more polar diastereoisomer of (4-dimethylamino-4-pyridin-2-yl-cyclohexyl)-acetic acid (476 mg, 1.6 mmol) in abs. dimethylformamide (20 ml) under argon. The solution was cooled in an ice-bath, dicyclohexylcarbodiimide (660 mg, 3.2 mmol) was added and the mixture was stirred at RT for 13 d, during which dicyclohexylurea precipitated out. Working up of the mixture was carried out by separating off the urea which had precipitated out and introducing the filtrate into a mixture of saturated NaCl solution (40 ml) and saturated NaHCO₃ solution (10 ml). Still further urea thereby precipitated out and was separated off. The aqueous phase was diluted with water (300 ml), 5 M sodium hydroxide solution (7 ml, 35 mmol) was added and the mixture was stored at 5° C. for 16 h. The crude product thereby precipitated out as a beige-coloured oily compound (319 mg, 49%). After purification by chromatography on silica gel (45 g) with methanol and methanol/30 percent strength aqueous ammonia (100:1), the product was obtained as a beige-coloured oil in a yield of 12% (80 mg).

2-(4-Dimethylamino-4-pyridin-2-ylcyclohexyl)-N-[2-(1H-indol-3-yl)ethyl]acetamide hydrochloride (Examples 47 and 48)

The less polar diastereoisomer of 2-(4-dimethylamino-4-pyridin-2-ylcyclohexyl)-N-[2-(1H-indol-3-yl)ethyl]acetamide (141 mg, 0.348 mmol) was dissolved in ethyl methyl ketone (6 ml), and chlorotrimethylsilane (0.126 ml, 1.0 mmol) was added. After a reaction time of 1 h, the hydrochloride was obtained as a beige-coloured solid in a yield of 84% (130 mg) with an m.p. of 150-153° C. (Example 47).

The more polar diastereoisomer of 2-(4-dimethylamino-4-pyridin-2-ylcyclohexyl)-N-[2-(1H-indol-3-yl)-ethyl]acetamide (80 mg, 0.20 mmol) was dissolved in ethyl methyl ketone (5 ml), trimethylchlorosilane (0.038 ml, 0.3 mmol) was added and the mixture was stirred at RT for 1.5 h. The hydrochloride which had precipitated out was obtained in a yield of 95% (84 mg) (Example 48).

2-(4-Dimethylamino-4-pyridin-2-ylcyclohexyl)-N-(3-phenylpropyl)acetamide

1-Hydroxybenzotriazole (689 mg, 5.1 mmol), 3-phenylpropylamine (345 mg, 2.55 mmol) and N-methylmorpholine (0.560 ml, 5.1 mmol) were added to a solution of the less polar diastereoisomer of (4-dimethylamino-4-pyridin-2-yl-cyclohexyl)-acetic acid (760 mg, 2.55 mmol) in abs. dimethylformamide (30 ml) under argon. The solution was cooled in an ice-bath, dicyclohexylcarbodiimide (1.05 g, 5.1 mmol) was added and the mixture was stirred at RT for 5 d, during which dicyclohexylurea precipitated out. Working up of the mixture was carried out by separating off the urea which had precipitated out and introducing the filtrate into a mixture of saturated NaCl solution (40 ml) and saturated NaHCO₃ solution (10 ml). Still further urea thereby precipitated out and was separated off. The aqueous phase was diluted with water (300 ml), 5 M sodium hydroxide solution (7 ml, 35 mmol) was added and the mixture was stored at 5° C. for 16 h. The crude product was thereby obtained as a beige-coloured oily compound (890 mg, 92%). After purification by chromatography on silica gel (50 g) with EA/methanol (10:1), the less polar diastereoisomer of 2-(4-dimethylamino-4-pyridin-2-ylcyclohexyl)-N-(3-phenylpropyl)acetamide was obtained as a colourless oil in a yield of 42% (403 mg).

2-(4-Dimethylamino-4-pyridin-2-ylcyclohexyl)-N-(3-phenylpropyl)acetamide hydrochloride (Example 49)

The less polar diastereoisomer of 2-(4-dimethylamino-4-pyridin-2-ylcyclohexyl)-N-(3-phenylpropyl)acetamide (400 mg, 1.05 mmol) was dissolved in ethyl methyl ketone (10 ml), and chlorotrimethylsilane (0.2 ml, 1.58 mmol) was added. After a reaction time of 2 h, the hydrochloride was obtained as a beige-coloured solid in a yield of 94% (411 mg) with an m.p. of 218-220° C.

2-[4-Dimethylamino-4-(3-fluorophenyl)cyclohexyl]-N-[2-(1H-indol-3-yl)ethyl]acetamide Palladium-on-charcoal (5%, 120 mg) was added to a solution of 2-[4-dimethylamino-4-(3-fluorophenyl)-cyclohexylidene]-N-[2-(1H-indol-3-yl)-ethyl]-acetamide (base of Example 25; 660 mg; 1.55 mmol) in abs. methanol (100 ml). The reaction mixture was hydrogenated at 40° C. under a pressure of 3 bar for 20 h. The catalyst was separated off over Celite and the filtrate was concentrated. After separation of the residue by chromatography on silica gel (45 g) with EA/methanol (5:1) and methanol, the less polar diastereoisomer of 2-[4-dimethylamino-4-(3-fluorophenyl)cyclohexyl]-N-[2-(1H-indol-3-yl)ethyl]acetamide was isolated in a yield of 13% (86 mg) and the more polar diastereoisomer of 2-[4-dimethylamino-4-(3-fluorophenyl)cyclohexyl]-N-[2-(1H-indol-3-yl)ethyl]acetamide was isolated in a yield of 59% (391 mg). Both amides were colourless oils and diastereomerically pure.

2-[4-Dimethylamino-4-(3-fluorophenyl)cyclohexyl]-N-[2-(1H-indol-3-yl)ethyl]acetamide hydrochloride (Examples 50 and 51)

The less polar diastereoisomer of 2-[4-dimethylamino-4-(3-fluorophenyl)cyclohexyl]-N-[2-(1H-indol-3-yl)ethyl]acetamide (86 mg, 0.204 mmol) was dissolved in ethyl methyl ketone (5 ml), and chlorotrimethylsilane (0.038 ml, 0.3 mmol) was added. After 1 h ether (30 ml) was added to the reaction mixture and the mixture was stirred at RT for 30 min. The hydrochloride was isolated as a colourless solid in a yield of 94% (87 mg) with m.p. of 135-140° C. (Example 50).

Chlorotrimethylsilane (0.164 ml, 1.3 mmol) was added to a solution of the more polar diastereoisomer of 2-[4-dimethylamino-4-(3-fluorophenyl)cyclohexyl]-N-[2-(1H-indol-3-yl)ethyl]acetamide (372 mg, 0.776 mmol) in ethyl methyl ketone (30 ml) and the mixture was stirred at RT for 1.5 h. The reaction mixture was concentrated to 10 ml, ether (60 ml) was added and the mixture was stirred at RT for 20 min. The hydrochloride was obtained as a colourless solid in a yield of 87% (348 mg) (Example 51).

2-[4-Dimethylamino-4-(3-fluorophenyl)cyclohexyl]-N-[2-(1H-indol-3-yl)-1-methylethyl]acetamide Palladium-on-charcoal (5%, 40 mg) was added to a solution of 2-[4-dimethylamino-4-(3-fluorophenyl)-cyclohexylidene]-N-[2-(1H-indol-3-yl)-1-methylethyl]-acetamide (417 mg, 0.96 mmol) in abs. methanol (40 ml). The reaction mixture was hydrogenated at RT under a pressure of 3 bar for 15 h. The catalyst was separated off over Celite and the filtrate was concentrated. After separation of the residue by chromatography on silica gel G [50 g; EA/MeOH (10:1)-(5:1)], the less polar diastereoisomer of 2-[4-dimethylamino-4-(3-fluorophenyl)cyclohexyl]-N-[2-(1H-indol-3-yl)-1-methylethyl]acetamide was isolated in a yield of 4% (15 mg) and the more polar diastereoisomer of 2-[4-dimethylamino-4-(3-fluorophenyl)cyclohexyl]-N-[2-(1H-indol-3-yl)-1-methylethyl]acetamide was isolated in a yield of 41% (170.2 mg). Both products were colourless oils and diastereoisomerically pure.

2-[4-Dimethylamino-4-(3-fluorophenyl)cyclohexyl]-N-[2-(1H-indol-3-yl)-1-methylethyl]acetamide hydrochloride (Example 52)

The more polar diastereoisomer of 2-[4-dimethylamino-4-(3-fluorophenyl)cyclohexyl]-N-[2-(1H-indol-3-yl)-1-methylethyl]acetamide (139 mg, 0.32 mmol) was dissolved in ethanol (10 ml) with gentle heating, 5 M isopropanolic hydrochloric acid (0.096 ml, 0.48 mmol) was added and the mixture was stirred at RT for 2 h. The clear solution was concentrated to approx. 1 ml and the residue was stirred with ether (10 ml) for 20 h. The solid thereby formed was filtered off with suction. The more polar diastereoisomer of 2-[4-dimethylamino-4-(3-fluorophenyl)cyclohexyl]-N-[2-(1H-indol-3-yl)-1-methylethyl]acetamide hydrochloride was obtained in this way as a pink-coloured solid in a yield of 93.5 mg (62%).

2-[4-Dimethylamino-4-(3-fluorophenyl)cyclohexyl]-N-(3-phenyl-propyl)acetamide

Palladium-on-charcoal (5%, 22 mg) was added to a solution of 2-[4-dimethylamino-4-(3-fluorophenyl)-cyclohexylidene]-N-(3-phenylpropyl)-acetamide (440 mg, 1.1 mmol) in abs. methanol (40 ml). The reaction mixture was hydrogenated at RT under a pressure of 3 bar for 16 h. The catalyst was separated off over Celite and the filtrate was concentrated. After separation of the residue by chromatography on silica gel G [(80 g; EA/MeOH (2:1)], the less polar diastereoisomer of 2-[4-dimethylamino-4-(3-fluorophenyl)cyclohexyl]-N-(3-phenylpropyl)acetamide was isolated as a colourless oil in a yield of 15% (64.3 mg) and the more polar diastereoisomer of 2-[4-dimethylamino-4-(3-fluorophenyl)cyclohexyl]-N-(3-phenylpropyl)acetamide was isolated as a colourless solid with an m.p. of 119-122° C. in a yield of 72% (314 mg).

2-[4-Dimethylamino-4-(3-fluorophenyl)cyclohexyl]-N-(3-phenylpropyl)-acetamide hydrochloride (Examples 53 and 54)

The less polar diastereoisomer of 2-[4-dimethylamino-4-(3-fluorophenyl)cyclohexyl]-N-(3-phenylpropyl)-acetamide (64.3 mg, 0.16 mmol) was dissolved in ethyl methyl ketone (10 ml), and chlorotrimethylsilane (0.03 ml, 0.24 mmol) was added. After 2 h ether (10 ml) was added to the reaction mixture and the mixture was stirred at RT for 30 min. The hydrochloride was isolated as a colourless, hygroscopic solid in a yield of 78% (54 mg) (Example 53).

Chlorotrimethylsilane (0.132 ml, 1.04 mmol) was added to a solution of the more polar diastereoisomer of 2-[4-dimethylamino-4-(3-fluorophenyl)cyclohexyl]-N-(3-phenylpropyl)-acetamide (274 mg, 0.69 mmol) in ethyl methyl ketone (20 ml) and the mixture was stirred at RT for 1 h. Ether (20 ml) was added to the reaction mixture and the mixture was stirred at RT for 1 h. The hydrochloride was obtained as a colourless solid in a yield of 82% (245.5 mg) with an m.p. of 205-207° C. (Example 54).

2-(4-Dimethylamino-4-phenyl-cyclohexyl)-N-phenyl-acetamide n-Butyllithium (1.6 M solution in hexane; 7.1 ml; 11.4 mmol) was added dropwise at 0° C. to a solution of aniline (0.53 g; 5.7 mmol) in 10 ml THF. The mixture was allowed to come to RT and was subsequently stirred for 1 h. A solution of (4-dimethylamino-4-phenyl-cyclohexyl)-acetic acid ethyl ester (1.5 g; 5.2 mmol) in 15 ml THF was added dropwise at −78° C. The mixture was subsequently stirred for 1 h and then allowed to come to RT. It was hydrolysed with ammonium chloride solution and extracted with MC. After concentration, the crude product was chromatographed on silica gel (eluent: ether). 308 mg (18%) of the less polar and 620 mg (36%) of the more polar diastereoisomer were obtained.

2-(4-Dimethylamino-4-phenyl-cyclohexyl)-N-phenyl-acetamide hydrochloride (Examples 55 and 56)

Chlorotrimethylsilane (0.124 ml) and water (9 µl) were added to a solution of the less polar diastereoisomer of 2-(4-dimethylamino-4-phenyl-cyclohexyl)-N-phenyl-acetamide (300 mg, 0.9 mmol) in ethyl methyl ketone (2 ml). After 18 h it was possible to isolate the hydrochloride as a colourless solid in a yield of 64% (210 mg) (Example 55).

An analogous procedure was followed with the more polar diastereoisomer (600 mg; 1.8 mmol). Since no precipitate precipitated out, the product was extracted as an oil with hexane. 670 mg (1.797 mmol; 99%) of the product were obtained (Example 56).

2-(4-Dimethylamino-4-phenyl-cyclohexyl)-N-(4-fluoro-phenyl)-acetamide n-Butyllithium (1.6 M solution in hexane; 11.9 ml; 19 mmol) was added dropwise at 0° C. to a solution of 4-fluoroaniline (1.06 g; 9.5 mmol) in 10 ml THF. The mixture was allowed to come to RT and was subsequently stirred for 1 h. A solution of (4-dimethylamino-4-phenyl-cyclohexyl)-acetic acid ethyl ester (2.5 g; 8.6 mmol) in 15 ml THF was added dropwise at −78° C. The mixture was subsequently stirred for 1 h and then allowed to come to RT. It was hydrolysed with ammonium chloride solution and extracted with MC. After concentration, the crude product was taken up in ether. A solid then remained (less polar diastereoisomer; 1.37 g; 45%); the supernatant was chromatographed on silica gel (eluent: ether). 315 mg (10%) of the more polar diastereoisomer were obtained.

2-(4-Dimethylamino-4-phenyl-cyclohexyl)-N-(4-fluoro-phenyl)-acetamide hydrochloride (Examples 57 and 58)

Chlorotrimethylsilane (0.118 ml) and water (8 μl) were added to a solution of the less polar diastereoisomer of 2-(4-dimethylamino-4-phenyl-cyclohexyl)-N-(4-fluoro-phenyl)-acetamide (300 mg, 0.8 mmol) in ethyl methyl ketone (2 ml) and a little methanol. After concentration it was possible to isolate the hydrochloride in a yield of 397 mg (quantitative) (Example 57).

Chlorotrimethylsilane (0.122 ml) and water (9 μl) were added to a solution of the more polar diastereoisomer of 2-(4-dimethylamino-4-phenyl-cyclohexyl)-N-(4-fluoro-phenyl)-acetamide (310 mg, 0.9 mmol) in ethyl methyl ketone (2 ml). After 18 h it was possible to isolate the hydrochloride as a solid in a yield of 64% (220 mg; 0.6 mmol) (Example 58).

2-(4-Dimethylamino-4-phenyl-cyclohexyl)-N-p-tolyl-acetamide n-Butyllithium (1.6 M solution in hexane; 11.9 ml; 19 mmol) was added dropwise at 0° C. to a solution of p-tolylamine (1.02 g; 9.5 mmol) in 10 ml THF. The mixture was allowed to come to RT and was subsequently stirred for 1 h. A solution of (4-dimethylamino-4-phenyl-cyclohexyl)-acetic acid ethyl ester (2.5 g; 8.6 mmol) in 15 ml THF was added dropwise at −78° C. The mixture was subsequently stirred for 1 h and then allowed to come to RT. It was hydrolysed with ammonium chloride solution and extracted with MC. After concentration, the crude product was taken up in ether. A solid then remained (less polar diastereoisomer; 1.518 g; 50%); the supernatant was chromatographed on silica gel (eluent:ether, then ether/methanol 4:1). 142 mg (4.7%) of the less polar and 1.20 g (40%) of the more polar diastereoisomer were obtained.

2-(4-Dimethylamino-4-phenyl-cyclohexyl)-N-p-tolyl-acetamide hydrochloride (Examples 59 and 60)

Chlorotrimethylsilane (0.056 ml) and water (4 μl) were added to a solution of the less polar diastereoisomer of 2-(4-dimethylamino-4-phenyl-cyclohexyl)-N-p-tolyl-acetamide (142 mg, 0.4 mmol) in ethyl methyl ketone (1 ml). After a short time a colourless solid precipitated out, which it was possible to isolate in a yield of 100 mg (63%) (Example 59).

Chlorotrimethylsilane (0.477 ml) and water (34 μl) were added to a solution of the more polar diastereoisomer of 2-(4-dimethylamino-4-phenyl-cyclohexyl)-N-p-tolyl-acetamide (1.2 g, 3.4 mmol) in ethyl methyl ketone (10 ml). The hydrochloride was extracted as an oil with hexane and isolated in a yield of 78% (1.04 g; 2.7 mmol) (Example 60).

2-(4-Dimethylamino-4-phenyl-cyclohexyl)-N-(4-methoxy-phenyl)-acetamide n-Butyllithium (1.6 M solution in hexane; 4.3 ml; 7.0 mmol) was added dropwise at 0° C. to a solution of 4-methoxy-phenylamine (430 mg; 3.5 mmol) in 5 ml THF. The mixture was allowed to come to RT and was subsequently stirred for 1 h. A solution of trans-(4-dimethylamino-4-phenyl-cyclohexyl)-acetic acid ethyl ester (0.92 g; 3.2 mmol) in 5 ml THF was added dropwise at −78° C. The mixture was subsequently stirred for 1 h and then allowed to come to RT. It was hydrolysed with ammonium chloride solution and extracted with MC. After concentration, the product was chromatographed on silica gel (eluent:ether, then ether/methanol 4:1). 255 mg (22%) of the less polar diastereoisomer were obtained.

2-(4-Dimethylamino-4-phenyl-cyclohexyl)-N-(4-methoxy-phenyl)-acetamide hydrochloride (Example 61)

Chlorotrimethylsilane (0.097 ml) and water (7 μl) were added to a solution of the less polar diastereoisomer of 2-(4-dimethylamino-4-phenyl-cyclohexyl)-N-(4-methoxy-phenyl)-acetamide (255 mg, 0.7 mmol) in ethyl methyl ketone (2 ml). The hydrochloride was extracted as an oil with hexane and isolated in a quantitative yield.

Investigations of the activity of the compounds according to the invention:

Measurement of the ORL1 Binding

The cyclohexane derivatives of the general formula I were investigated in a receptor binding assay with $^3$H-nociceptin/orphanin FQ with membranes from recombinant CHO—ORL1 cells. This test system was conducted in accordance with the method described by Ardati et al. (Mol. Pharmacol., 51, 1997, p. 816-824). The concentration of $^3$H-nociceptin/orphanin FQ in these experiments was 0.5 nM. The binding assays were carried out with in each case 20 μg of membrane protein per 200 μl batch in 50 mM hepes, pH 7.4, 10 mM $MgCl_2$ and 1 mM EDTA. The binding to the ORL1 receptor was determined using in each case 1 mg WGA-SPA beads (Amersham-Pharmacia, Freiburg) by incubation of the batch for one hour at RT and subsequent measurement in a Trilux scintillation counter (Wallac, Finland). The affinity is stated in Table 1 as the nanomolar $K_i$ value in or % inhibition at c=1 μM.

Measurement of the μ Binding

The receptor affinity for the human μ-opiate receptor was determined in a homogeneous batch in microtitre plates. For this, dilution series of the particular substituted cyclohexylacetic acid derivative to be tested were incubated in a total volume of 250 μl for 90 minutes at room temperature with a receptor membrane preparation (15-40 μg protein per 250 μl incubation batch) of CHO-K1 cells, which express the human μ-opiate receptor (RB-HOM receptor membrane preparation of NEN, Zaventem, Belgium), in the presence of 1 nmol/l of the radioactive ligand [$^3$H]-naloxone (NET719, NEN, Zaventem, Belgium) and of 1 mg WGA-SPA beads (wheat germ agglutinin SPA beads from Amersham/Pharmacia, Freiburg, Germany). 50 mmol/l Tris-HCl supplemented with 0.05 wt. % sodium azide and with 0.06 wt. % bovine serum albumin was used as the incubation buffer. 25 μmol/l naloxone was additionally added for determination of the non-specific binding. When the ninety minutes of incubation time had ended, the microtitre plates were centrifuged off at 1,000 g for 20 minutes and the radioactivity was measured in a β-counter (Microbeta-Trilux, PerkinElmer Wallac, Freiburg, Germany). The percentage displacement of the radioactive ligand from its binding to the human μ-opiate receptor at a concentration of the test substances of 1 μmol/l was determined and was stated as the percentage inhibition (% inhibition) of the specific binding. In some cases, on the basis of the percentage displacement by different concentrations of the compounds of the general formula I to be tested, $IC_{50}$ inhibitory concentrations which cause 50 percent displacement of the radioactive ligand were calculated. By conversion by means of the Cheng-Prusoff relationship, Ki values were obtained for the test substances.

Measurement of the Serotonin Reuptake

In order to be able to carry out these in vitro studies, synaptosomes are freshly isolated from rat brain areas. In each case a so-called "$P_2$" fraction, which is prepared in accordance with the instructions of Gray and Whittaker (E. G. Gray and V. P. Whittaker (1962) J. Anat. 76, 79-88), is used. For the 5HT uptake, these vesicular particles are isolated from the medulla+pons region of male rat brains.

A detailed description of the method can be found in the literature (M. Ch. Frink, H.-H. Hennies, W. Englberger, M. Haurand and B. Wilffert (1996) Arzneim.-Forsch./Drug Res. 46 (III), 11, 1029-1036).

Measurement of the Noradrenaline Reuptake

In order to be able to carry out these in vitro studies, synaptosomes are freshly isolated from rat brain areas. In each case a so-called "$P_2$" fraction, which is prepared in accordance with the instructions of Gray and Whittaker (E. G. Gray and V. P. Whittaker (1962) J. Anat. 76, 79-88), is used. For the NA uptake, these vesicular particles are isolated from the hypothalamus of male rat brains.

A detailed description of the method can be found in the literature (M. Ch. Frink, H.-H. Hennies, W. Englberger, M. Haurand and B. Wilffert (1996) Arzneim.-Forsch./Drug Res. 46 (III), 11, 1029-1036).

Testing of Analgesia in the Tail Flick Test in Mice

The mice were in each case placed individually in a test cage and the base of the tail was exposed to the focused heat ray of an electric lamp (Tail-flick type 50/08/1.bc, Labtec, Dr Hess). The intensity of the lamp was adjusted such that in the case of untreated mice the time between switching on of the lamp to sudden pulling away of the tail (pain latency) was 3 to 5 seconds. Before administration of the solutions containing the compound according to the invention or the particular comparison solutions, the mice were pretested twice in the course of five minutes and the mean of these measurements was calculated as the pretest mean.

The solutions of the compound of the general formula I according to the invention and the comparison solutions were then administered intravenously. The pain was measured in each case 10, 20, 40 and 60 minutes after the intravenous administration. The analgesic action was determined as the increase in pain latency (% of the maximum possible antinociceptive effect) according to the following formula:

$$[(T_1-T_0)/(T_2-T_0)]\times 100$$

In this formula, the time $T_0$ is the latency period before the administration and the time $T_1$ the latency period after the administration of the active compound combination and the time $T_2$ is the maximum duration of exposure (12 seconds).

The following data were determined by way of example:

| Example number | ORL1% 1 µM | ORL1 Ki | ORµNal % 1 µm | ORµNal Ki |
|---|---|---|---|---|
| 1 | 98.00 | 0.0016 | 100.5 | 0.0005 |
| 2 | 97.00 | 0.0046 | 100.5 | 0.0012 |
| 3 | 94.00 | 0.0032 | 101.00 | 0.0014 |
| 4 | 98.5 | 0.0025 | 97.5 | 0.0014 |
| 6 | 90.00 | 0.0130 | 101.00 | 0.0031 |
| 7 | 84.00 | 0.0500 | 100.00 | 0.0082 |
| 8 | 85.00 | 0.0210 | 103.00 | 0.0011 |
| 9 | 93.00 | 0.0110 | 96.00 | 0.0014 |
| 10 | 37.00 | — | 9.15 | 0.021 |
| 11 | 88.00 | 0.0360 | 99.00 | 0.0043 |
| 12 | 93.00 | 0.0170 | 105.00 | 0.0057 |
| 13 | 84.00 | 0.0530 | 104.00 | 0.0028 |
| 14 | 85 | 0.0270 | 96.5 | 0.0089 |
| 15 | 92 | 0.0057 | 101 | 0.0052 |
| 16 | 88 | 0.0360 | 98 | 0.0041 |

-continued

| Example number | ORL1% 1 µM | ORL1 Ki | ORµNal % 1 µm | ORµNal Ki |
|---|---|---|---|---|
| 17 | 94 | 0.0170 | 100 | 0.008 |
| 18 | 90 | 0.0490 | 102 | 0.037 |
| 19 | 49 | — | 93 | 0.0075 |
| 20 | 81 | 0.0780 | 81 | 0.0052 |
| 21 | 88 | 0.0430 | 92 | 0.0013 |
| 22 | 83 | 0.0800 | 107 | 0.0021 |
| 23 | 92 | 0.0280 | 106 | 0.0027 |
| 24 | 46 | — | 83 | 0.0091 |
| 25 | 98 | 0.0029 | 97 | 0.0016 |
| 26 | 98 | 0.0023 | 90 | 0.0007 |
| 27 | 98 | 0.0026 | 96 | 0.0016 |
| 28 | 96 | 0.0110 | 102 | 0.0012 |
| 29 | 63.00 | — | 91.5 | 0.0059 |
| 30 | 98.00 | 0.001 | 91.5 | 0.0003 |
| 31 | 97.00 | 0.0026 | 96 | 0.0024 |
| 32 | 91.00 | 0.018 | 97 | 0.0026 |
| 33 | 95.00 | 0.0079 | 101 | 0.0009 |
| 34 | 94 | 0.0021 | 97 | 0.0028 |
| 35 | 72.00 | 0.059 | 95 | 0.017 |
| 36 | 66.00 | — | 93.5 | 0.0086 |
| 37 | 99.00 | 0.004 | 99 | 0.0013 |
| 38 | 88.00 | 0.021 | 97 | 0.0057 |
| 39 | 98.00 | 0.0033 | 104 | 0.0018 |
| 40 | 91.00 | 0.028 | 104 | 0.0098 |
| 41 | 98.00 | 0.0024 | 103 | 0.0009 |
| 42 | 56.00 | — | 107 | 0.0052 |
| 43 | 71.00 | 0.012 | 98 | 0.021 |
| 44 | 89.00 | 0.039 | 106 | 0.0012 |
| 45 | 65.00 | — | 114 | 0.0076 |
| 46 | 84.00 | 0.093 | 66 | 0.0009 |
| 50 | 97.00 | 0.0058 | 102 | 0.002 |
| 51 | 98.00 | 0.0058 | 96 | 0.011 |
| 52 | 99.00 | 0.0024 | 99 | 0.0013 |
| 53 | 97.00 | 0.0067 | 106 | 0.0014 |
| 54 | 99.00 | 0.0021 | 107 | 0.0017 |

| Example number | 5HT uptake % (10) | NA uptake % (10) |
|---|---|---|
| 1 | 96 | 102 |
| 2 | 90 | 78.5 |
| 3 | 94 | 72 |
| 4 | 92 | 101 |
| 6 | 101 | 102 |
| 7 | 89 | 64 |
| 8 | 97 | 93 |
| 9 | 93 | 94 |
| 10 | 92.5 | 84.5 |
| 11 | 92 | 90 |
| 12 | 90 | 85 |
| 13 | 95 | 98 |
| 14 | 95 | 79.5 |
| 15 | 93 | 96 |
| 16 | 91 | 95 |
| 17 | 91 | 94 |
| 18 | 91 | 91 |
| 19 | 88 | 101 |
| 20 | 92 | 101 |
| 21 | 84 | 99 |
| 22 | 84 | 95 |
| 23 | 89 | 92 |
| 24 | 82 | 87 |
| 25 | 91 | 96 |
| 26 | 95 | 81 |
| 27 | 96 | 88 |
| 28 | 96 | 94 |
| 29 | 90 | 52.5 |
| 30 | 85 | 78.5 |
| 31 | 83 | 95 |
| 32 | 76 | 44 |
| 33 | 81 | 86 |

-continued

| Example number | 5HT uptake % (10) | NA uptake % (10) |
|---|---|---|
| 34 | 77 | 57 |
| 36 | 94.5 | 50.5 |
| 37 | 99 | 83 |
| 38 | 92 | 92 |
| 39 | 96 | 89 |
| 40 | 93 | 84 |
| 41 | 83 | 55 |
| 42 | 90 | 97 |
| 43 | 76 | 100 |
| 44 | 92 | 69 |
| 45 | 87 | 90 |
| 46 | 87 | 62 |
| 47 | 46 | 63 |
| 48 | 85 | 74 |
| 49 | 32 | 94 |
| 50 | 86 | 94 |
| 51 | 72 | 67 |
| 52 | 96 | 57 |
| 53 | 94 | 96 |
| 54 | 92 | 90 |

| Example number | TFMiv % [1 mg/kg] |
|---|---|
| 2 | 62 |
| 4 | 69 |
| 8 | 93 |
| 9 | 74 |
| 10 | 100 (10 mg/kg) |
| 11 | 81 |
| 13 | 99 |
| 25 | 42 |
| 30 | 90 (10 mg/kg) |
| 32 | 93 (10 mg/kg) |
| 34 | 89 (10 mg/kg) |

Parenteral solution of a substituted cyclohexylacetic acid derivative according to the invention 38 g of one of the substituted cyclohexylacetic acid derivatives according to the invention, here Example 1, are dissolved in 1 l of water for injection purposes at room temperature and the solution is then adjusted to isotonic conditions by addition of anhydrous glucose for injection purposes.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A cyclohexyl acetamide compound of formula I

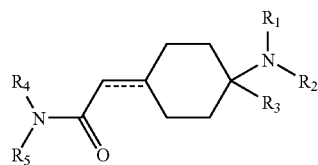

wherein
------represents a C—C single bond or double bond,
$R^1$ and $R^2$ independently of one another represent H; CHO; $C_{1-5}$-lkyl, in each case saturated or unsaturated, branched or unbranched, unsubstituted or mono- or polysubstituted by F, Cl, Br, I, —CN, $NH_2$, NH-alkyl, NH-aryl, NH-heteroaryl, NH-cycloalkyl, NH-alkyl-aryl, NH-alkyl-heteroaryl, NH-alkyl-OH, $N(alkyl)_2$, $N(alkyl-aryl)_2$, $N(alkyl-heteroaryl)_2$, $N(cycloalkyl)_2$, $N(alkyl-OH)_2$, $NO_2$, SH, S-alkyl, S-aryl, S-heteroaryl, S-alkyl-aryl, S-alkyl-heteroaryl, S-cycloalkyl, S-alkyl-OH, S-alkyl-SH, OH, O-aryl, O-heteroaryl, O-alkyl-aryl, O-alkyl-heteroaryl, O-cycloalkyl, O-alkyl-OH, CHO, $C(=O)C_{1-6}$-alkyl, $C(=S)C_{1-6}$-alkyl, $C(=O)$aryl, $C(=S)$aryl, $C(=O)C_{1-6}$-alkyl-aryl, $C(=S)C_{1-6}$-alkyl-aryl, $C(=O)$-heteroaryl, $C(=S)$-heteroaryl, $C(=O)$-cycloalkyl, $C(=S)$-cycloalkyl, $CO_2H$, $CO_2$-alkyl, $CO_2$-alkyl-aryl, $C(=O)NH_2$, $C(=O)NH$-alkyl, $C(=O)NH$aryl, $C(=O)NH$-cycloalkyl, $C(=O)N(alkyl)_2$, $C(=O)N(alkyl-aryl)_2$, $C(=O)N(alkyl-heteroaryl)_2$, $C(=O)N(cycloalkyl)_2$, SO-alkyl, $SO_2$-alkyl, $SO_2NH_2$, $SO_3H$, $PO(O-C_{1-6}$-alkyl$)_2$, $Si(C_{1-6}$-alkyl$)_3$, $Si(C_{3-8}$-cycloalkyl$)_3$, $Si(CH_2-C_{3-8}$-cycloalkyl$)_3$, $Si(phenyl)_3$, cycloalkyl, aryl or heteroaryl; $C_{3-8}$-cycloalkyl, in each case saturated or unsaturated, mono- or polysubstituted or unsubstituted; or aryl, $C_{3-8}$-cycloalkyl or heteroaryl bonded via $C_{1-3}$-alkyl and in each case mono- or polysubstituted or unsubstituted; or $R^1$ and $R^2$ together form a ring and represent $CH_2CH_2OCH_2CH_2$, $CH_2CH_2NR^{10}CH_2CH_2$ or $(CH_2)_{3-6}$, wherein $R^{10}$ denotes H; $C_{1-5}$-alkyl, in each case saturated or unsaturated, branched or unbranched, mono- or polysubstituted or unsubstituted; $C_{3-8}$-cycloalkyl, in each case saturated or unsaturated, mono- or polysubstituted or unsubstituted; aryl or heteroaryl, in each case mono- or polysubstituted or unsubstituted; or aryl, $C_{3-8}$-cycloalkyl or heteroaryl bonded via $C_{1-3}$-alkyl and in each case mono- or polysubstituted or unsubstituted;

$R^3$ represents:

$C_{3-8}$-cycloalkyl, in each case saturated or unsaturated, mono- or polysubstituted or unsubstituted;

aryl, heteroaryl or $C_{3-8}$-cycloalkyl bonded via $C_{1-3}$-alkyl and in each case unsubstituted or mono- or polysubstituted;

naphthyl, anthracenyl, thiophenyl, benzothiophenyl, furyl, benzofuranyl, benzodioxolanyl, indolyl, indanyl, benzodioxanyl, pyrrolyl, pyridyl, pyrimidyl or pyrazinyl, in each case unsubstituted or mono- or polysubstituted;

phenyl, 2-fluorophenyl, 3-fluorophenyl, 4-fluorophenyl, 2-chlorophenyl, 4-chlorophenyl, 3-chlorophenyl, 2-bromophenyl, 3-bromophenyl, 4-bromophenyl, 2-cyanophenyl, 3-cyanophenyl, 4-cyanophenyl, 2-methylphenyl, 3-methylphenyl, 4-methylphenyl, 2-methoxyphenyl, 3-methoxyphenyl, 4-methoxyphenyl, 2-trifluoromethylphenyl, 3-trifluoromethylphenyl, 4-trifluoromethylphenyl, 2-ethylphenyl, 3-ethylphenyl, 4-ethylphenyl, 2-ethoxyphenyl, 3-ethoxyphenyl, 4-ethoxyphenyl, 2-hydroxyphenyl, 3-hydroxyphenyl, 4-hydroxyphenyl, 2,3-dichlorophenyl, 3,4-dichlorophenyl, 3,5-dichlorophenyl, 2,4-dichlorophenyl, 2,3-difluorophenyl, 3,4-difluorophenyl, 3,5-difluorophenyl, 2,4-difluorophenyl, 2-fluoro-3-chlorophenyl, 2-chloro-3-fluorophenyl, 2-chloro-4-fluorophenyl, 2-fluoro-4-chlorophenyl, 4-fluoro-3-chlorophenyl, 4-fluoro-3-methylphenyl, 4-tert-butylphenyl, 4-fluoro-3-chlorophenyl, 4-bromo-3-fluorophenyl, 3,5-bis(trifluoromethyl) phenyl, 4-chloro-2-trifluoromethylphenyl, 2-methoxy-5-methylphenyl, 5-chloro-2-methoxyphenyl, 4-phenoxyphenyl, 2-methylthiophenyl, 3-methylthiophenyl, 4-methylthiophenyl, 5-fluoro-2-methoxyphenyl, 4-chloro-3-trifluoromethyl or 4-bromo-2-methylphenyl;

$R^4$ represents —$(CR^6R^7)_nR^8$, wherein n denotes 0, 1, 2, 3, 4, 5 or 6, $R^6$ denotes H or $C_{1-5}$-alkyl, branched or unbranched, saturated or unsaturated, unsubstituted or mono- or polysubstituted, $R^7$ denotes H, $C_{1-5}$-alkyl, branched or unbranched, saturated or unsaturated, unsubstituted or mono- or polysubstituted, or $COOR^9$, or $R^6$ and $R^7$ form a $(CH_2)_kCHR^8(CH_2)_m$ ring, where k=1, 2 or 3 and m=1 or 2, $R^8$ denotes $C_{3-8}$-cycloalkyl, aryl or heteroaryl, in each case unsubstituted or mono- or polysubstituted by F, Cl, Br, I, CN, $NH_2$, NH-alkyl, NH-aryl, NH-heteroaryl, NH-alkyl-aryl, NH-alkyl-heteroaryl, NH-cycloalkyl, NH-alkyl-OH, N(alkyl)$_2$, N(alkyl-aryl)$_2$, N(alkyl-heteroaryl)$_2$, N(cycloalkyl)$_2$, N(alkyl-OH)$_2$, $NO_2$, SH, S-alkyl, S-cycloalkyl, S-aryl, S-heteroaryl, S-alkyl-aryl, S-alkyl-heteroaryl, S-cycloalkyl, S-alkyl-OH, S-alkyl-SH, OH, O-alkyl, β-cycloalkyl, O-aryl, O-heteroaryl, O-alkyl-aryl, O-alkyl-heteroaryl, O-cycloalkyl, O-alkyl-OH, CHO, C(=O)$C_{1-6}$-alkyl, C(=S)$C_{1-6}$-alkyl, C(=O)aryl, C(=S)aryl, C(=O)—$C_{1-6}$-alkyl-aryl, C(=S)$C_{1-6}$-alkyl-aryl, C(=O)-heteroaryl, C(=S)-heteroaryl, C(=O)-cycloalkyl, C(=S)-cycloalkyl, $CO_2$H, $CO_2$-alkyl, $CO_2$-alkyl-aryl, C(=O)$NH_2$, C(=O)NH-alkyl, C(=O)NHaryl, C(=O)NH-cycloalkyl, C(=O)N(alkyl)$_2$, C(=O)N(alkyl-aryl)$_2$, C(=O)N(alkyl-heteroaryl)$_2$, C(=O)N(cycloalkyl)$_2$, S(O)-alkyl, S(O)-aryl, $SO_2$-alkyl, $SO_2$-aryl, $SO_2NH_2$, $SO_3$H, $CF_3$, =O, =S; alkyl, cycloalkyl, aryl or heteroaryl, and $R^9$ denotes H or $C_{1-5}$-alkyl, branched or unbranched, saturated or unsaturated, unsubstituted or mono- or polysubstituted;

$R^5$ represents H or —$(CH_2)_lR^8$, wherein l represents 1, 2 or 3, or $R^5$ and $R^4$ together form a ring and represent $CH_2CH_2OCH_2CH_2$ or $CH_2CH_2NR^{11}CH_2CH_2$, wherein $R^{11}$ denotes H; $C_{1-5}$-alkyl, in each case saturated or unsaturated, branched or unbranched, mono- or polysubstituted or unsubstituted; $C_{3-8}$-cycloalkyl, in each case saturated or unsaturated, mono- or polysubstituted or unsubstituted; aryl or heteroaryl, in each case mono- or polysubstituted or unsubstituted; or aryl, $C_{3-8}$-cycloalkyl or heteroaryl bonded via $C_{1-3}$-alkyl and in each case mono- or polysubstituted or unsubstituted;

or a physiologically acceptable salt thereof;

said compound exhibiting opioid receptor activity at the μ and ORL1 receptors.

2. The compound of claim 1, wherein said compound is present in the form of an isolated enantiomer or isolated diastereoisomer.

3. The compound of claim 1, wherein said compound is present in the form of a mixture of stereoisomers.

4. The compound of claim 1, wherein said compound is present in the form of a racemic mixture.

5. The compound according to claim 1, wherein $R^1$ and $R^2$ independently of one another represent H; $C_{1-5}$-alkyl, saturated or unsaturated, branched or unbranched, unsubstituted or mono- or polysubstituted by F, Cl, Br, I, —CN, $NH_2$, NH-alkyl, NH-aryl, NH-heteroaryl, NH-cycloalkyl, NH-alkyl-aryl, NH-alkyl-heteroaryl, NH-alkyl-OH, N(alkyl)$_2$, N(alkyl-aryl)$_2$, N(alkyl-heteroaryl)$_2$, N(cycloalkyl)$_2$, N(alkyl-OH)$_2$, $NO_2$, SH, S-alkyl, S-aryl, S-heteroaryl, S-alkyl-aryl, S-alkyl-heteroaryl, S-cycloalkyl, S-alkyl-OH, S-alkyl-SH, OH, O-aryl, O-heteroaryl, O-alkyl-aryl, O-alkyl-heteroaryl, O-cycloalkyl, O-alkyl-OH, CHO, C(=O)$C_{1-6}$-alkyl, C(=S)$C_{1-6}$-alkyl, C(=O)aryl, C(=S)aryl, C(=O)$C_{1-6}$-alkyl-aryl, C(=S)$C_{1-6}$-alkyl-aryl, C(=O)-heteroaryl, C(=S)-heteroaryl, C(=O)-cycloalkyl, C(=S)-cycloalkyl, $CO_2$H, $CO_2$-alkyl, $CO_2$-alkyl-aryl, C(=O)$NH_2$, C(=O)NH-alkyl, C(=O)NHaryl, C(=O)NH-cycloalkyl, C(=O)N(alkyl)$_2$, C(=O)N(alkyl-aryl)$_2$, C(=O)N(alkyl-heteroaryl)$_2$, C(=O)N(cycloalkyl)$_2$, SO-alkyl, $SO_2$-alkyl, $SO_2NH_2$, $SO_3$H, PO(O—$C_{1-6}$-alkyl)$_2$, Si($C_{1-6}$-alkyl)$_3$, Si($C_{3-8}$-cycloalkyl)$_3$, Si($CH_2$—$C_{3-8}$-cycloalkyl)$_3$, Si(phenyl)$_3$, cycloalkyl, aryl or heteroaryl; or $R^1$ and $R^2$ together form a ring and represent $CH_2CH_2OCH_2CH_2$, $CH_2CH_2NR^{10}CH_2CH_2$ or $(CH_2)_{3-6}$, wherein $R^{10}$ denotes H; $C_{1-5}$-alkyl, saturated or unsaturated, branched or unbranched, mono- or polysubstituted or unsubstituted.

6. A cyclohexyl acetamide compound of formula I

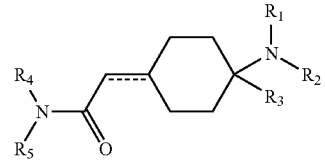

wherein

-----represents a C—C single bond or double bond, $R^1$ and $R^2$ each represent $CH_3$ or H, and wherein $R^1$ and $R^2$ do not simultaneously represent H;

$R^3$ represents $C_{1-5}$-alkyl, in each case saturated or unsaturated, branched or unbranched, mono- or polysubstituted or unsubstituted; $C_{3-8}$-cycloalkyl, in each case saturated or unsaturated, mono- or polysubstituted or unsubstituted; aryl, heteroaryl or $C_{3-8}$-cycloalkyl bonded via $C_{1-3}$-alkyl and in each case unsubstituted or mono- or polysubstituted; naphthyl, anthracenyl, thiophenyl, benzothiophenyl, furyl, benzofuranyl, benzodioxolanyl, indolyl, indanyl, benzodioxanyl, pyrrolyl, pyridyl, pyrimidyl or pyrazinyl, in each case unsubstituted or mono- or polysubstituted; phenyl, 2-fluorophenyl, 3-fluorophenyl, 4-fluorophenyl, 2-chlorophenyl, 4-chlorophenyl, 3-chlorophenyl, 2-bromophenyl, 3-bromophenyl, 4-bromophenyl, 2-cyanophenyl, 3-cyanophenyl, 4-cyanophenyl, 2-methylphenyl, 3-methylphenyl, 4-methylphenyl, 2-methoxyphenyl, 3-methoxyphenyl, 4-methoxyphenyl, 2-trifluoromethylphenyl, 3-trifluoromethylphenyl, 4-trifluoromethylphenyl, 2-ethylphenyl, 3-ethylphenyl, 4-ethylphenyl, 2-ethoxyphenyl, 3-ethoxyphenyl, 4-ethoxyphenyl, 2-hydroxyphenyl, 3-hydroxyphenyl, 4-hydroxyphenyl, 2,3-dichlorophenyl, 3,4-dichlorophenyl, 3,5-dichlorophenyl, 2,4-dichlorophenyl, 2,3-difluorophenyl, 3,4-difluorophenyl, 3,5-difluorophenyl, 2,4-difluorophenyl, 2-fluoro-3-chlorophenyl, 2-chloro- 3-fluorophenyl, 2-chloro-4-fluorophenyl, 2-fluoro-4-chlorophenyl, 4-fluoro-3-chlorophenyl, 4-fluoro-3-methylphenyl, 4-tert-butylphenyl, 4-fluoro-3-chlorophenyl, 4-bromo-3-fluorophenyl, 3,5-bis(trifluoromethyl)phenyl, 4-chloro-2-trifluoromethylphenyl, 2-methoxy-5-methylphenyl, 5-chloro-2-methoxyphenyl, 4-phenoxyphenyl, 2-methylthiophenyl, 3-methylthiophenyl, 4-methylthiophenyl, 5-fluoro-2-methoxyphenyl, 4-chloro-3-trifluoromethyl or 4-bromo-2-methylphenyl;

$R^4$ represents —$(CR^6R^7)_n R^8$, wherein n denotes 0, 1, 2, 3, 4, 5 or 6, $R^6$ denotes H or $C_{1-5}$-alkyl, branched or unbranched, saturated or unsaturated, unsubstituted or mono- or polysubstituted, $R^7$ denotes H, $C_{1-5}$-alkyl, branched or unbranched, saturated or unsaturated, unsubstituted or mono- or polysubstituted, or $COOR^9$, or $R^6$ and $R^7$ form a $(CH_2)_k CHR^8(CH_2)_m$ ring, where k=1, 2 or 3 and m=1 or 2, $R^8$ denotes $C_{3-8}$-cycloalkyl, aryl or heteroaryl, in each case unsubstituted or mono- or polysubstituted by F, Cl, Br, I, CN, $NH_2$, NH-alkyl, NH-aryl, NH-heteroaryl, NH-alkyl-aryl, NH-alkyl-heteroaryl, NH-cycloalkyl, NH-alkyl-OH, N(alkyl), N(alkyl-aryl)$_2$, N(alkyl-heteroaryl)$_2$, N(cycloalkyl)$_2$, N(alkyl-OH)$_2$, $NO_2$, SH, S-alkyl, S-cycloalkyl, S-aryl, S-heteroaryl, S-alkyl-aryl, S-alkyl-heteroaryl, S-cycloalkyl, S-alkyl-OH, S-alkyl-SH, OH, O-alkyl, O-cycloalkyl, O-aryl, O-heteroaryl, O-alkyl-aryl, O-alkyl-heteroaryl, O-cycloalkyl, O-alkyl-OH, CHO, C(=O)$C_{1-6}$-alkyl, C(=S)$C_{1-6}$-alkyl, C(=O)aryl, C(=S)aryl, C(=O)—$C_{1-6}$-alkyl-aryl, C(=S)$C_{1-6}$-alkyl-aryl, C(=O)-heteroaryl, C(=S)-heteroaryl, C(=O)-cycloalkyl, C(=S)-cycloalkyl, $CO_2H$, $CO_2$-alkyl, $CO_2$-alkyl-aryl, C(=O)$NH_2$, C(=O)NH-alkyl, C(=O)NHaryl, C(=O)NH-cycloalkyl, C(=O)N(alkyl)$_2$, C(=O)N(alkyl-aryl)$_2$, C(=O)N(alkyl-heteroaryl)$_2$, C(=O)N(cycloalkyl)$_2$, S(O)-alkyl, S(O)-aryl, $SO_4$-alkyl, $SO_4$-aryl, $SO_2NH_2$, $SO_3H$, $CF_3$, =O, =S; alkyl, cycloalkyl, aryl or heteroaryl, and $R^9$ denotes H or $C_{1-5}$-alkyl, branched or unbranched, saturated or unsaturated, unsubstituted or mono- or polysubstituted;

$R^5$ represents H or —$(CH_2)_l R^8$, wherein l represents 1, 2 or 3, or $R^5$ and $R^4$ together form a ring and represent $CH_2CH_2OCH_2CH_2$ or $CH_2CH_2NR^{11}CH_2CH_2$, wherein $R^{11}$ denotes H; $C_{1-5}$-alkyl, in each case saturated or unsaturated, branched or unbranched, mono- or polysubstituted or unsubstituted; $C_{3-8}$-cycloalkyl, in each case saturated or unsaturated, mono- or polysubstituted or unsubstituted; aryl or heteroaryl, in each case mono- or polysubstituted or unsubstituted; or aryl, $C_{3-8}$-cycloalkyl or heteroaryl bonded via $C_{1-3}$-alkyl and in each case mono- or polysubstituted or unsubstituted;

or a physiologically acceptable salt thereof;

said compound exhibiting opioid receptor activity at the μ and ORL1 receptors.

7. The compound according to claim 1, wherein $R^3$ represents cyclopentyl, cyclohexyl, naphthyl, thiophenyl, benzothiophenyl, furyl, benzofuranyl, benzodioxolanyl, indolyl, indanyl, benzodioxanyl or pyridyl, in each case unsubstituted or mono- or polysubstituted; $C_{5-6}$-cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl bonded via a saturated, unbranched $C_{1-2}$-alkyl group and in each case unsubstituted or mono- or polysubstituted; phenyl, 2-fluorophenyl, 3-fluorophenyl, 4-fluorophenyl, 2-chlorophenyl, 4-chlorophenyl, 3-chlorophenyl, 2-bromophenyl, 3-bromophenyl, 4-bromophenyl, 2-cyanophenyl, 3-cyanophenyl, 4-cyanophenyl, 2-methylphenyl, 3-methylphenyl, 4-methylphenyl, 2-methoxyphenyl, 3-methoxyphenyl, 4-methoxyphenyl, 2-trifluoromethylphenyl, 3-trifluoromethylphenyl, 4-trifluoromethylphenyl, 2-ethylphenyl, 3-ethylphenyl, 4-ethylphenyl, 2-ethoxyphenyl, 3-ethoxyphenyl, 4-ethoxyphenyl, 2-hydroxyphenyl, 3-hydroxyphenyl, 4-hydroxyphenyl, 2,3-dichlorophenyl, 3,4-dichlorophenyl, 3,5-dichlorophenyl, 2,4-dichlorophenyl, 2,3-difluorophenyl, 3,4-difluorophenyl, 3,5-difluorophenyl, 2,4-difluorophenyl, 2-fluoro-3-chlorophenyl, 2-chloro-3-fluorophenyl, 2-chloro-4-fluorophenyl, 2-fluoro-4-chlorophenyl, 4-fluoro-3-chlorophenyl, 4-fluoro-3-methylphenyl, 4-tert-butylphenyl, 4-fluoro-3-chlorophenyl, 4-bromo-3-fluorophenyl, 3,5-bis(trifluoromethyl)phenyl, 4-chloro-2-trifluoromethylphenyl, 2-methoxy-5-methylphenyl, 5-chloro-2-methoxyphenyl, 4-phenoxyphenyl, 2-methylthiophenyl, 3-methylthiophenyl, 4-methylthiophenyl, 5-fluoro-2-methoxyphenyl, 4-chloro-3-trifluoromethyl or 4-bromo-2-methylphenyl.

8. The compound according to claim 1, wherein $R^3$ represents naphthyl, thiophenyl or pyridyl, in each case unsubstituted or mono- or polysubstituted; $C_{5-6}$-cycloalkyl, phenyl, naphthyl, thiophenyl or pyridyl bonded via a saturated, unbranched $C_{1-2}$-alkyl group and in each case unsubstituted or mono- or polysubstituted; phenyl, 2-fluorophenyl, 3-fluorophenyl, 4-fluorophenyl, 2-chlorophenyl, 4-chlorophenyl, 3-chlorophenyl, 2-cyanophenyl, 3-cyanophenyl, 4-cyanophenyl, 2-methylphenyl, 3-methylphenyl, 4-methylphenyl, 2-methoxyphenyl, 3-methoxyphenyl, 4-methoxyphenyl, 2-trifluoromethylphenyl, 3-trifluoromethylphenyl, 4-trifluoromethylphenyl, 2-ethylphenyl, 3-ethylphenyl, 4-ethylphenyl, 2-ethoxyphenyl, 3-ethoxyphenyl, 4-ethoxyphenyl, 2,3-dichlorophenyl, 3,4-dichlorophenyl, 3,5-dichlorophenyl, 2,4-dichlorophenyl, 2,3-difluorophenyl, 3,4-difluorophenyl, 3,5-difluorophenyl, 2,4-difluorophenyl, 2-fluoro-3-chlorophenyl, 2-chloro-3-fluorophenyl, 2-chloro-4-fluorophenyl, 2-fluoro-4-chlorophenyl, 4-fluoro-3-chlorophenyl, 4-fluoro-3-methylphenyl, 4-tert-butylphenyl, 4-fluoro-3-chlorophenyl, 3,5-bis(trifluoromethyl)phenyl, 4-chloro-2-trifluoromethylphenyl, 2-methoxy-5-methylphenyl, 5-chloro-2-methoxyphenyl, 4-phenoxyphenyl, 2-methylthiophenyl, 3-methylthiophenyl, 4-methylthiophenyl or 4-chloro-3-trifluoromethyl.

9. The compound according to claim 1, wherein $R^3$ represents pyridyl, phenyl, 3-fluorophenyl or 4-fluorophenyl.

10. The compound according to claim 1, wherein $R^6$ represents H, and $R^7$ represents H, $CH_3$ or $COOR^9$; or $R^6$ and $R^7$ together form a $(CH_2)_k CHR^8(CH_2)_m$ ring, where k=1, 2 or 3, and m=1 or 2.

11. The compound according to claim 1, wherein $R^5$ represents H.

12. The compound according to claim 1, wherein $R^8$ represents cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl, pyrimidyl, fluorenyl, fluoranthenyl, benzothiazolyl, benzotriazolyl, benzo[1,2,5]thiazolyl, 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl, in each case unsubstituted or mono- or polysubstituted.

13. The compound according to claim 1, wherein $R^8$ represents cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, in each case unsubstituted or mono- or polysubstituted.

14. The compound according to claim 1, wherein $R^8$ represents phenyl or indolyl, in each case mono- or polysubstituted.

15. A compound selected from the group consisting of:
2-(4-dimethylamino-4-phenyl-cyclohexylidene)-N-[2-(1H-indol-3-yl)-ethyl]-acetamide;
2-[2-(4-dimethylamino-4-phenyl-cyclohexylidene)-acetylamino]-3-(1H-indol-3-yl)-propanoic acid methyl ester;
2-(4-dimethylamino-4-phenyl-cyclohexylidene)-N-(3-phenyl-propyl)-acetamide;
N-benzyl-2-(4-dimethylamino-4-phenyl-cyclohexylidene)-acetamide;
2-[2-(4-dimethylamino-4-phenyl-cyclohexylidene)-acetylamino]-3-(1H-indol-3-yl)-propanoic acid methyl ester;
2-(4-dimethylamino-4-phenyl-cyclohexylidene)-N-phenethyl-acetamide;
2-(4-dimethylamino-4-phenyl-cyclohexylidene)-N-[2-(4-fluoro-phenyl)-ethyl]-acetamide;
2-(4-dimethylamino-4-phenyl-cyclohexylidene)-N-(4-fluoro-benzyl)-acetamide;
2-(4-dimethylamino-4-phenyl-cyclohexylidene)-N-(2-trifluoromethyl-benzyl)-acetamide;
2-(4-dimethylamino-4-phenyl-cyclohexylidene)-N-(4-fluoro-phenyl)-acetamide;
2-(4-dimethylamino-4-phenyl-cyclohexylidene)-N-[2-(1H-indol-3-yl)-1-methyl-ethyl]-acetamide;
2-(4-Dimethylamino-4-phenyl-cyclohexylidene)-N-(4-phenyl-butyl)-acetamide;
2-(4-dimethylamino-4-phenyl-cyclohexylidene)-N-(1H-indol-3-ylmethyl)-acetamide;
2-(4-dimethylamino-4-phenyl-cyclohexylidene)-N-[4-(1H-indol-3-yl)-butyl]-acetamide;
2-(4-dimethylamino-4-phenyl-cyclohexylidene)-N-[3-(1H-indol-3-yl)-propyl]-acetamide;
2-(4-dimethylamino-4-phenyl-cyclohexylidene)-N-[5-(1H-indol-3-yl)-pentyl]-acetamide;
2-(4-dimethylamino-4-phenyl-cyclohexylidene)-N-[6-(1H-indol-3-yl)-hexyl]-acetamide;
2-[4-dimethylamino-4-(4-fluoro-phenyl)-cyclohexylidene]-N-(3-phenyl-propyl)-acetamide;
2-[4-dimethylamino-4-(4-fluoro-phenyl)-cyclohexylidene]-N-[2-(1H-indol-3-yl)-ethyl]-acetamide;
2-[4-dimethylamino-4-(4-fluoro-phenyl)-cyclohexylidene]-N[2-(1H-indol-3-yl)-1-methyl-ethyl]-acetamide;
2-(4-dimethylamino-4-pyridin-2-yl-cyclohexylidene)-N-[2-(1H-indol-3-yl)-ethyl]-acetamide;
2-(4-dimethylamino-4-pyridin-2-yl-cyclohexylidene)-N-(3-phenyl-propyl)-acetamide;
2-[4-dimethylamino-4-(3-fluoro-phenyl)-cyclohexylidene]-N-[2-(1H-indol-3-yl)-ethyl]-acetamide;
2-[4-dimethylamino-4-(3-fluoro-phenyl)-cyclohexylidene]-N-(3-phenyl-propyl)-acetamide;
2-[4-dimethylamino-4-(3-fluoro-phenyl)-cyclohexylidene]-N-[2-(1H-indol-3-yl)-1-methyl-ethyl]-acetamide;
2-(4-dimethylamino-4-phenylcyclohexyl)-N-(2-trifluoromethyl-benzyl)-acetamide;
2-(4-dimethylamino-4-phenylcyclohexyl)-N-[2-(1H-indol-3-yl)-ethyl]-acetamide;
2-(4-dimethylamino-4-phenylcyclohexyl)-N-(3-phenyl-propyl)-acetamide;
2-(4-dimethylamino-4-phenylcyclohexyl)-N-phenethylacetamide;
2-(4-dimethylamino-4-phenylcyclohexyl)-N-(4-phenyl-butyl)-acetamide;
2-[2-(4-dimethylamino-4-phenylcyclohexyl)-acetylamino]-3-(1H-indol-3-yl)-propanoic acid methyl ester;
2-(4-dimethylamino-4-phenylcyclohexyl)-N-(1H-indol-3-ylmethyl)-acetamide;
2-(4-dimethylamino-4-phenylcyclohexyl)-N-[4-(1H-indol-3-yl)-butyl]-acetamide;
2-(4-dimethylamino-4-phenylcyclohexyl)-N-[3-(1H-indol-3-yl)-propyl]-acetamide;
2-(4-dimethylamino-4-phenylcyclohexyl)-N-[5-(1H-indol-3-yl)-pentyl]-acetamide;
2-(4-dimethylamino-4-phenylcyclohexyl)-N-[2-(1H-indol-3-yl)-1-methylethyl]-acetamide;
2-[4-dimethylamino-4-(4-fluorophenyl)-cyclohexyl]-N-(3-phenylpropyl)-acetamide;
2-(4-dimethylamino-4-phenylcyclohexyl)-N-[6-(1H-indol-3-yl)-hexyl]-acetamide;
2-[4-dimethylamino-4-(4-fluorophenyl)-cyclohexyl]-N-[2-(1H-indol-3-yl)-ethyl]-acetamide;
2-[4-dimethylamino-4-(4-fluorophenyl)-cyclohexyl]-N-[2-(1H-indol-3-yl)-1-methylethyl]-acetamide;
2-(4-dimethylamino-4-pyridin-2-yl-cyclohexyl)-N-(3-phenylpropyl)-acetamide;
2-(4-dimethylamino-4-pyridin-2-yl-cyclohexyl)-N-[2-(1H-indol-3-yl)-ethyl]-acetamide;
2-[4-dimethylamino-4-(3-fluorophenyl)-cyclohexyl]-N-[2-(1H-indol-3-yl)-ethyl]-acetamide;
2-[4-dimethylamino-4-(3-fluorophenyl)-cyclohexyl]-N-(3-phenylpropyl)-acetamide;
2-[4-dimethylamino-4-(3-fluorophenyl)-cyclohexyl]-N-[2-(1H-indol-3-yl)-1-methylethyl]-acetamide;
a hydrochloride of any of the foregoing;
2-(4-Dimethylamino-4-phenyl-cyclohexyl)-N-phenyl-acetamide hydrochloride;
2-(4-Dimethylamino-4-phenyl-cyclohexyl)-N-(4-fluoro-phenyl)-acetamide hydrochloride;
2-(4-Dimethylamino-4-phenyl-cyclohexyl)-N-p-tolyl-acetamide hydrochloride;
2-(4-Dimethylamino-4-phenyl-cyclohexyl)-N-(4-methoxy-phenyl)-acetamide hydrochloride; and
potassium 2-[2-(4-dimethylamino-4-phenylcyclohexyl)-acetylamino]-3-(1H-indol-3-yl)-propanoate.

16. A pharmaceutical formulation comprising at least one compound according to claim 1 and one or more physiologically acceptable auxiliary substances.

* * * * *